United States Patent [19]

Murata et al.

[11] Patent Number: 5,102,877

[45] Date of Patent: Apr. 7, 1992

[54] 1-AZABICYCLO[3.2.0]HEPT-2-ENE-2-CARBOXYLIC ACID COMPOUNDS

[75] Inventors: Masayoshi Murata; Toshiyuki Chiba, both of Osaka; Hideo Tsutsumi, Toyonaka; Kohji Hattori, Sakai; Satoru Kuroda, Ikeda; Hiroaki Ohtake, Suita; Fumiyuki Shirai, Osaka, all of Japan

[73] Assignee: Fujisawa Pharmaceutical Co., Ltd., Osaka, Japan

[21] Appl. No.: 508,167

[22] Filed: Apr. 12, 1990

[30] Foreign Application Priority Data

Apr. 28, 1989 [GB] United Kingdom ............... 8909797
Jul. 17, 1989 [GB] United Kingdom ............... 8916316
Sep. 22, 1989 [GB] United Kingdom ............... 8921463

[51] Int. Cl.$^5$ .................... C07D 487/04; A61K 31/40
[52] U.S. Cl. ...................................... 514/210; 540/302
[58] Field of Search ...................... 540/302; 514/710

[56] References Cited

U.S. PATENT DOCUMENTS

| | | | |
|---|---|---|---|
| 4,260,627 | 4/1981 | Christensen et al. | 540/302 |
| 4,267,188 | 5/1981 | Cama et al. | 540/302 |
| 4,348,320 | 9/1982 | Bouffard et al. | 540/302 |
| 4,465,632 | 8/1984 | Christensen et al. | 540/302 |
| 4,517,127 | 5/1985 | Yoshioka | 540/302 |
| 4,543,257 | 9/1985 | Cama et al. | 540/302 |
| 4,740,507 | 8/1988 | Sujimura et al. | 540/302 |

FOREIGN PATENT DOCUMENTS

| | | |
|---|---|---|
| 10317 | 4/1980 | European Pat. Off. . |
| 72710 | 2/1983 | European Pat. Off. . |
| 289801 | 11/1988 | European Pat. Off. . |

*Primary Examiner*—Robert Gerstl
*Attorney, Agent, or Firm*—Oblon, Spivak, McClelland, Maier & Neustadt

[57] ABSTRACT

1-Azabicyclo[3.2.0]hept-2-ene-2-carboxyic acids having antimicrobial activity have been prepared.

9 Claims, No Drawings

1-AZABICYCLO[3.2.0]HEPT-2-ENE-2-CARBOXYLIC ACID COMPOUNDS

The present invention relates to novel 1-azabicyclo[3.2.0]hept-2-ene-2-carboxylic acid compounds and pharmaceutically acceptable salts thereof.

More particularly, it relates to novel 1-azabicyclo[3.2.0]hept-2-ene-2-carboxylic acid compounds and pharmaceutically acceptable salts thereof, which have antimicrobial activity.

Accordingly, the object of the present invention is to provide novel 1-azabicyclo[3.2.0]hept-2-ene-2-carboxylic acid compounds and pharmaceutically acceptable salts thereof, which are highly active against a number of pathogenic microorganisms and are useful as antimicrobial agents.

The object 1-azabicyclo[3.2.0]hept-2-ene-2-carboxylic acid compounds are novel and can be represented by the following general formula:

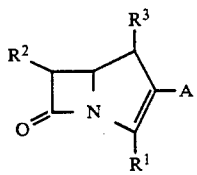

in which
$R^1$ is carboxy, protected carboxy or carboxylato,
$R^2$ is hydroxy(lower)alkyl or protected hydroxy(lower)alkyl,
$R^3$ is hydrogen or lower alkyl,
A is a group of the formula:

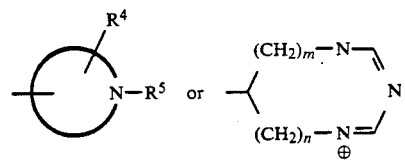

wherein

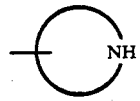

is N-containing a aliphatic heterocyclic group optionally containing additional hetero atom(s),
$R^4$ is hydrogen, hydroxy, protected hydroxy, hydroxy(lower)alkyl, protected hydroxy(lower)alkyl, lower alkyl, lower alkoxy(lower)alkyl, halogen, carbamoyl, mono- or di(lower)alkylcarbamoyl or imino-protective group,
$R^5$ is hydrogen, lower alkenyl, carbamoyl mono-or di(lower)alkylcarbamoyl, imino-protective group, or a group of the formula:

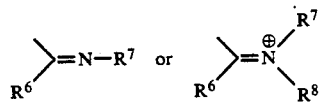

wherein
$R^6$ is hydrogen or lower alkyl optionally substituted by suitable substituent(s),
$R^7$ is hydrogen, lower alkyl, cyano, hydroxy(lower)alkoxy(lower)alkyl or heterocyclic group,
$R^8$ is lower alkyl, or
$R^7$ is combined with $R^6$ or $R^8$ to form lower alkylene, and
m and n are each an integer of 0 to 3,
or pharmaceutically acceptable salts thereof.

Suitable pharmaceutically acceptable salts of the object compound (I) are conventional non-toxic salts and may include a salt with a base such as an inorganic base salt, for example, an alkali metal salt (e.g. sodium salt, potassium salt, etc.), an alkaline earth metal salt (e.g. calcium salt, magnesium salt, etc.), an ammonium salt, an organic base salt, for example, an organic amine salt (e.g. triethylamine salt, pyridine salt, picoline salt, ethanolamine salt, triethanolamine salt, dicyclohexylamine salt, N,N'-dibenzylethylenediamine salt, etc.); a salt with an acid such as inorganic acid addition salt (e.g. hydrochloride, hydrobromide, sulfate, phosphate, etc.), an organic acid addition salt (e.g. formate, acetate, trifluoroacetate, maleate, tartrate, methanesulfonate, benzenesulfonate, etc.); a salt with a basic or acidic amino acid (e.g. arginine, aspartic acid, glutamic acid, etc.); intramolecular quaternary salt and the like.

Said intramolecular salt can be formed when $R^5$ is lower alkenyl and the nitrogen atom in a group of the formula:

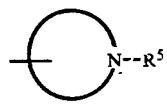

has an additional substituent such as lower alkyl, and $R^2$ is carboxylato, or $R^5$ is a group of the formula:

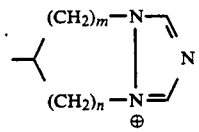

and $R^2$ is carboxylato, and suitable example of the former intramolecular quaternary salt may include 1-(lower)alkenyl-1-(lower)alkylpyrrolidinio carboxylate (e.g. 1-allyl-1-methyl-3-pyrrolidinio carboxylate, etc.), and the like.

In the object compound (I) and the intermediary compounds mentioned below, it is to be understood that there may be one or more stereo-isomeric pair(s) such as optical isomers due to asymmetric carbon atom(s), and such isomers are also included within the scope of the present invention.

According to the present invention, the object compound (I) or pharmaceutically acceptable salts thereof can be prepared by the processes as illustrated by the following reaction schemes.

Process 1:

-continued

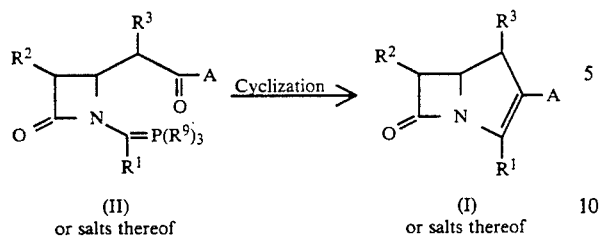

(II) or salts thereof → Cyclization → (I) or salts thereof

Process 2:

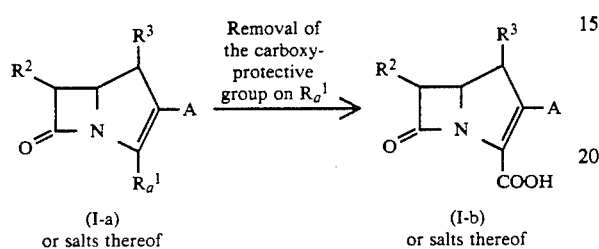

(I-a) or salts thereof → Removal of the carboxy-protective group on $R_a^1$ → (I-b) or salts thereof Process 3:

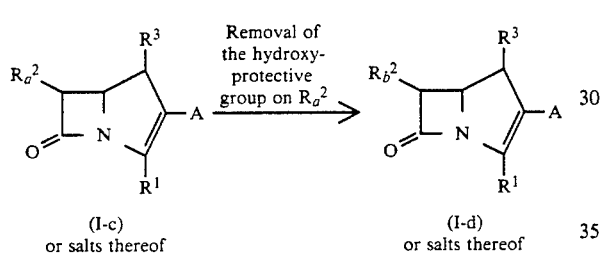

(I-c) or salts thereof → Removal of the hydroxy-protective group on $R_a^2$ → (I-d) or salts thereof Process 4:

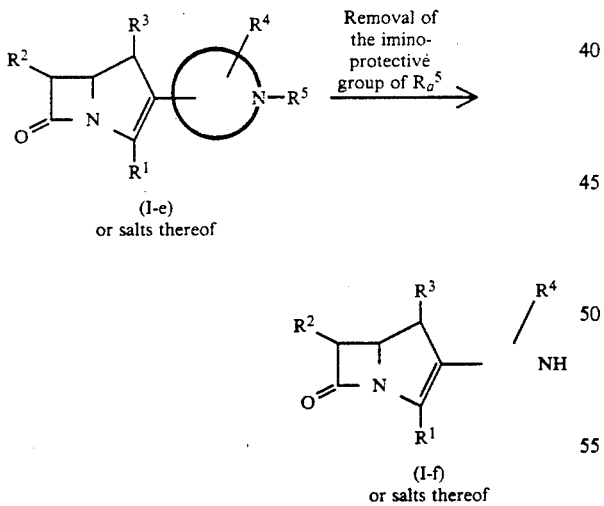

(I-e) or salts thereof → Removal of the imino-protective group of $R_a^5$ →

(I-f) or salts thereof

Process 5:

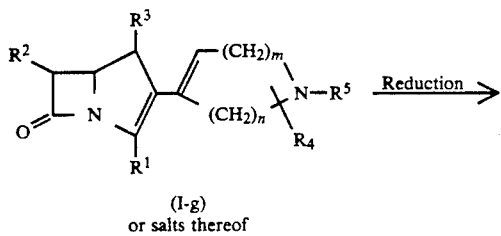

(I-g) or salts thereof → Reduction →

-continued

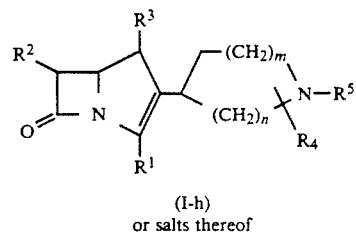

(I-h) or salts thereof

Process 6:

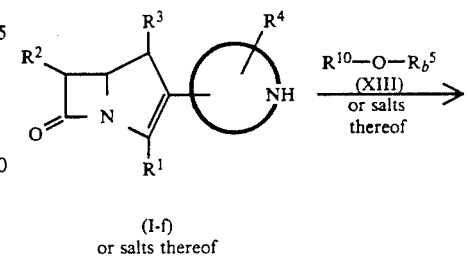

(I-f) or salts thereof → $R^{10}-O-R_b^5$ (XIII) or salts thereof →

(I-i) or salts thereof

Process 7:

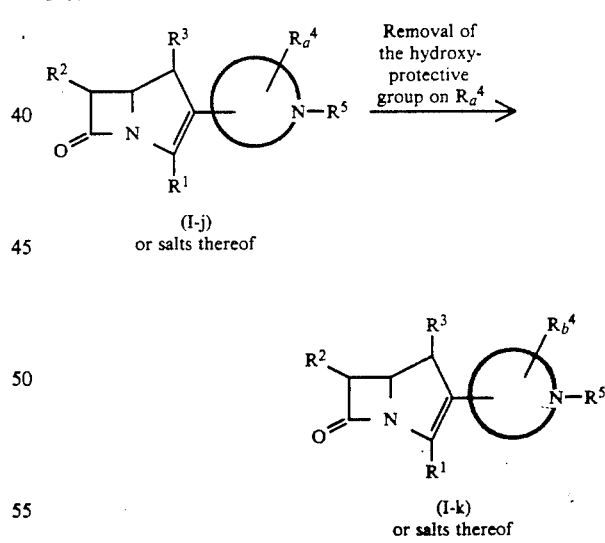

(I-j) or salts thereof → Removal of the hydroxy-protective group on $R_a^4$ →

(I-k) or salts thereof

Process 8:

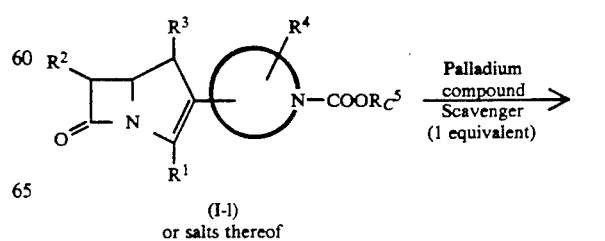

(I-l) or salts thereof → Palladium compound Scavenger (1 equivalent) →

-continued

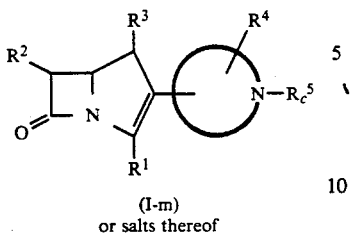

(I-m)
or salts thereof

Process 9:

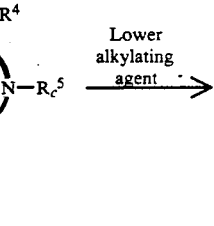 → Lower alkylating agent →

(I-m)
or salts thereof

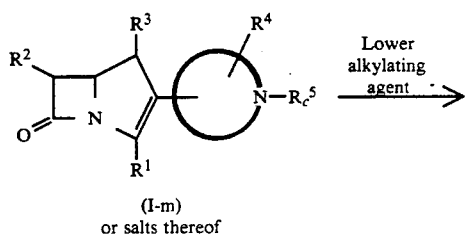

(I-n)
or salts thereof

Process 10:

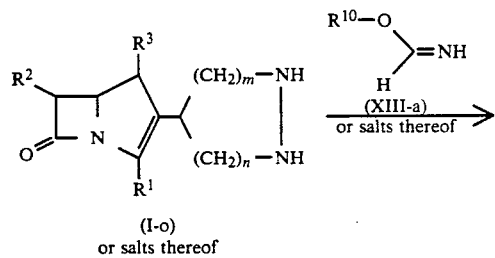

(I-o)
or salts thereof

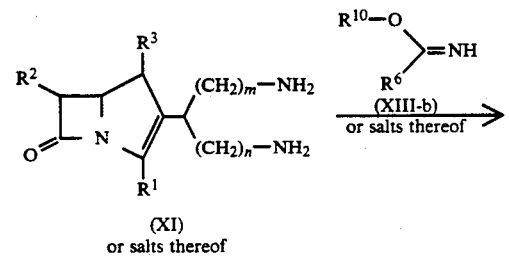

(I-p)

Process 11:

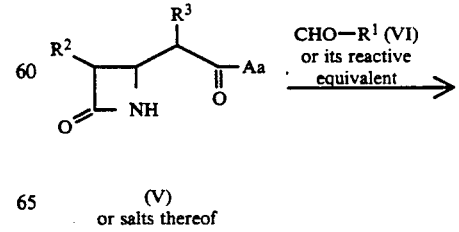

(XI)
or salts thereof

-continued

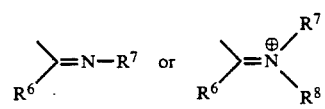

(I-q)
or salts thereof in which $R^1$, $R^2$, $R^3$, $R^4$, $R^5$ m, n, A and the formula:

are each as defined above,
$R_a{}^1$ is protected carboxy,
$R_a{}^2$ is protected hydroxy(lower)alkyl,
$R_b{}^2$ is hydroxy(lower)alkyl,
$R_a{}^4$ is protected hydroxy or protected hydroxy(lower)alkyl,
$R_b{}^4$ is hydroxy or hydroxy(lower)alkyl,
$R_a{}^5$ is imino-protective group,
$R_b{}^5$ is a group of the formula:

wherein
$R^6$, $R^7$ and $R^8$ are each as defined above,
$R_c{}^5$ is lower alkenyl,
$R^9$ is lower alkoxy or aryl,
$R^{10}$ is lower alkyl or ar(lower)alkyl, and
$R^{11}$ is lower alkyl.

The starting compounds (II) and (XI) used in the Processes 1 and 11 are new and can be prepared, for example, by the methods as shown in the following.

Method A:

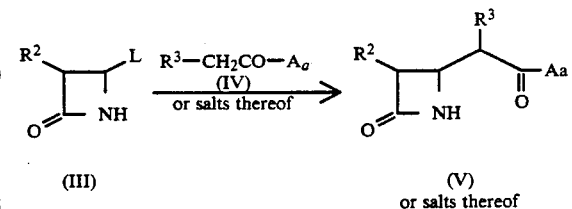

Method B:

(V)
or salts thereof

-continued

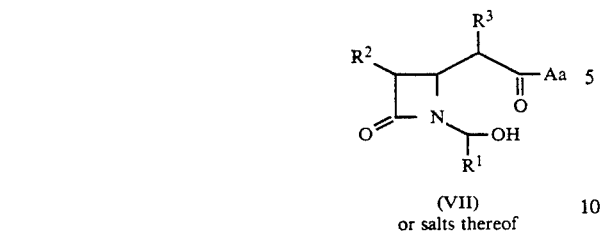

(VII) or salts thereof

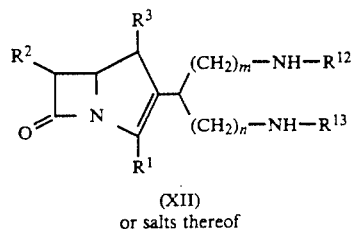

(XII) or salts thereof

Method C:

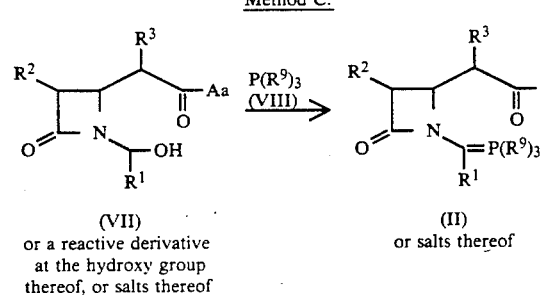

(VII) or a reactive derivative at the hydroxy group thereof, or salts thereof (II) or salts thereof Method G:

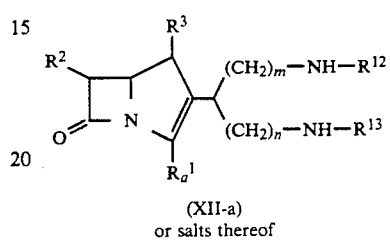

Removal of the carboxy-protective group on $R_a^1$ →

(XII-a) or salts thereof

Method D:

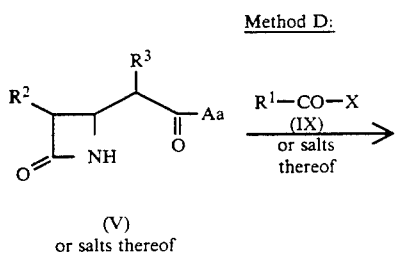

(V) or salts thereof

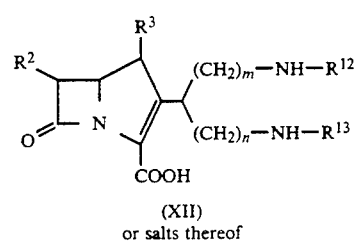

(XII) or salts thereof

Method H:

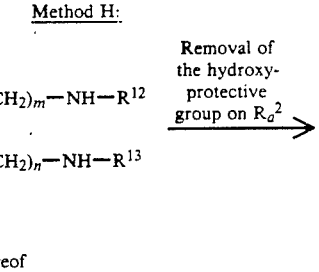

Removal of the hydroxy-protective group on $R_a^2$ →

(XII-c) or salts thereof

Method E:

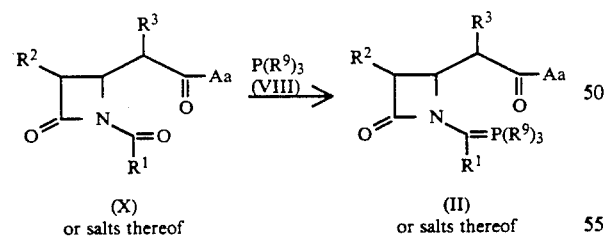

(X) or salts thereof (II) or salts thereof

Method F:

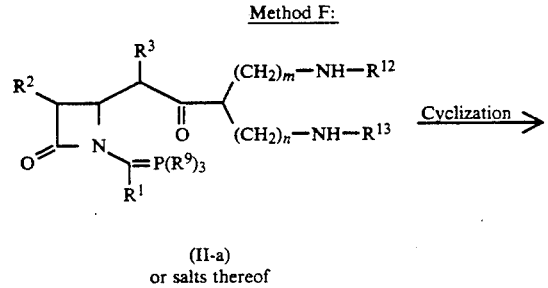

(II-a) or salts thereof

Method I:

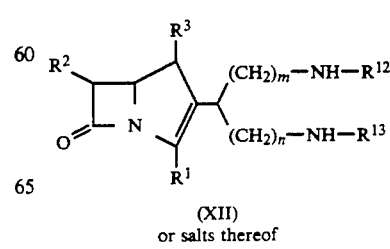

Removal of the imino-protective group(s) on $R^{12}$ and/or $R^{13}$ →

(XII) or salts thereof

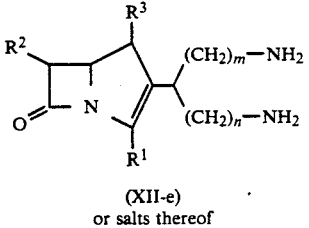

(XII-e)
or salts thereof in which
R$^1$, R$_a^1$, R$^2$, R$_a^2$, R$_b^2$, R$^3$, R$^9$, m and n are each as defined above,
A$_a$ is a group of the formula:

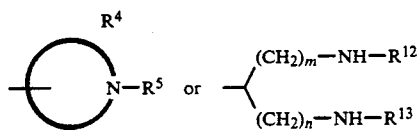

wherein
R$^4$, R$^5$, m, n and the formula:

are each as defined above, and
R$^{12}$ and R$^{13}$ are each hydrogen or imino-protective group,
L is a leaving group, and
X is halogen.

In the above and subsequent descriptions of the present specification, suitable examples and illustrations of the various definitions which the present invention includes within the scope thereof are explained in detail as follows.

The term "lower" is intended to mean 1 to 6 carbon atom(s), unless otherwise indicated.

Suitable "protected carboxy" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester t-butyl ester, pentyl ester, hexyl ester, etc.) which may have at least one suitable substituent, for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester; mono(or di or tri)halo(lower)alkyl ester (e.g. 2-iodoethyl ester, 2,2,2-trichloroethyl ester, etc.); lower alkenyl ester (e.g. vinyl ester, allyl ester, etc.); ar(lower)alkyl ester which may have at least one suitable substituent (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-t-butylbenzyl ester, etc.); and the like.

More preferable example of the protected carboxy thus defined may be C$_2$-C$_4$ alkenyloxycarbonyl and phenyl(or nitrophenyl)(C$_1$-C$_4$)alkoxycarbonyl and the most preferable one may be allyloxycarbonyl and 4-nitrobenzyloxycarbonyl.

Suitable "hydroxy(lower)alkyl" may include straight or branched lower alkyl having hydroxy group such as hydroxymethyl, hydroxyethyl, hydroxypropyl, 1-(hydroxymethyl)ethyl, 1-hydroxy-1-methylethyl, hydroxybutyl, hydroxypentyl, hydroxyhexyl, and the like, in which more preferable example may be hydroxy(C$_1$-C$_4$)-alkyl and the most preferable one may be 1-hydroxyethyl for R$^2$ and hydroxymethyl for R$^4$.

Suitable "protected hydroxy(lower)alkyl" means aforementioned hydroxy(lower)alkyl, in which the hydroxy group is protected by a conventional hydroxy-protective group such as those mentioned in the explanation of imino-protective group as mentioned below; and further ar(lower)alkyl such as mono- or di- or triphenyl(lower)alkyl (e.g. benzyl, benzhydryl, trityl, etc.); trisubstituted silyl such as tri(lower)alkylsilyl (e.g. trimethylsilyl, triethylsilyl, isopropyldimethylsilyl, t-butyldimethylsilyl, diisopropylmethylsilyl, etc.), triarylsilyl (e.g. triphenylsilyl, etc.), triar(lower)alkylsilyl (e.g. tribenzylsilyl, etc.), etc.; and the like.

More preferable example of "protected hydroxy(lower)alkyl thus defined may be {phenyl(or nitrophenyl)(C$_1$-C$_4$)alkoxy}carbonyloxy(C$_1$-C$_4$)alkyl and {tri(C$_1$-C$_4$)alkylsilyl}oxy(C$_1$-C$_4$)alkyl, and the most preferable one may be 1-trimethylsilyloxyethyl and 1-t-butyldimethylsilyloxyethyl for R$^2$, and t-butyldimethylsilyloxymethyl for R$^4$.

Suitable "protected hydroxy" means conventional one, in which the hydroxy group is protected by a conventional hydroxy-protective group such as those mentioned in the explanation of protected hydroxy(lower)alkyl as mentioned above, in which more preferable example may be {phenyl(or nitrophenyl)(C$_1$-C$_4$)alkoxy}carbonyloxy and {tri(C$_1$-C$_4$)alkylsilyl}oxy, and the most preferable one may be t-butyldimethylsilyloxymethyl.

Suitable "lower alkyl" may include straight or branched one such as methyl, ethyl, propyl, isopropyl, butyl, t-butyl, pentyl, hexyl, and the like, in which more preferable example may be C$_1$-C$_4$ alkyl, and the most preferable one may be methyl for R$^3$, R$^6$ and R$^8$, and methyl, ethyl and isopropyl for R$^7$.

Suitable "lower alkoxy(lower)alkyl" may include straight or branched hydroxy(lower)alkyl as mentioned above, in which the hydroxy group is substituted by lower alkyl group as mentioned above, in which preferable example may be C$_1$-C$_4$ alkoxy(C$_1$-C$_4$)alkyl and the most preferable one may be methoxymethyl.

Suitable "imino-protective group" may include acyl such as carbamoyl, aliphatic acyl, aromatic acyl, heterocyclic acyl and aliphatic acyl substituted with aromatic or heterocyclic group(s) derived from carboxylic, carbonic, sulfonic and carbamic acids.

The aliphatic acyl may include saturated or unsaturated, acyclic or cyclic ones, for example, alkanoyl such as lower alkanoyl (e.g. formyl, acetyl, propionyl, butyryl, isobutyryl, valeryl, isovaleryl, pivaloyl, hexanoyl, etc.), alkylsulfonyl such as lower alkylsulfonyl (e.g. mesyl, ethylsulfonyl, propylsulfonyl, isopropylsulfonyl, butylsulfonyl isobutylsulfonyl, pentylsulfonyl, hexylsulfonyl, etc.), carbamoyl, N-alkylcarbamoyl (e.g. methylcarbamoyl, ethylcarbamoyl, etc.), alkoxycarbonyl such as lower alkoxycarbonyl (e.g. methoxycarbonyl, ethoxycarbonyl, propoxycarbonyl, butoxycarbonyl, t-butoxycarbonyl, etc.), alkenyloxycarbonyl such as lower alkenyloxycarbonyl (e.g. vinyloxycarbonyl, allyloxycarbonyl, etc.), alkenoyl such as lower alkenoyl (e.g. acryloyl, methacryloyl, crotonoyl, etc.), cycloalkanecarbonyl such as cyclo(lower)alkanecarbonyl (e.g. cyclopropanecarbonyl, cyclopentanecarbonyl, cyclohexanecarbonyl, etc.), and the like.

The aliphatic acyl substituted with aromatic group(s) may include aralkoxycarbonyl such as phenyl(lower)alkoxycarbonyl (e.g. benzyloxycarbonyl, phenethyloxycarbonyl, etc.), and the like.

These acyl groups may be further substituted with one or more suitable substituent(s) such as nitro, and the like, and preferable acyl having such substituent(s) may be nitroaralkoxycarbonyl (e.g. nitrobenzyloxycarbonyl, etc.), and the like.

More preferable example of "imino-protective group" thus defined may be $C_2$-$C_4$ alkenyloxycarbonyl and phenyl(or nitrophenyl)($C_1$-$C_4$)alkoxycarbonyl and the most preferable one may be allyloxycarbonyl for $R^4$, and allyloxycarbonyl and benzyloxycarbonyl for $R^5$.

Suitable "lower alkoxy" may include straight or branched one such as methoxy, ethoxy, propoxy, isopropoxy, butoxy, isobutoxy, pentyloxy, isopentyloxy, hexyloxy, etc., in which more preferable example may be $C_1$-$C_4$ alkoxy and the most preferable one may be ethoxy.

Suitable "aryl" may include $C_6$-$C_{10}$ aryl such as phenyl, tolyl, xylyl, cumenyl, mesithyl, naphthyl, and the like, in which more preferable example may be phenyl.

Suitable "leaving group" may include an inorganic acid residue such as azido, halogen (e.g. chlorine, bromine, fluorine or iodine), and the like, an organic acid residue such as acyloxy, for example, lower alkanoyloxy (e.g. acetoxy, etc.), sulfonyloxy (e.g. benzenesulfonyloxy, tosyloxy, methanesulfonyloxy, etc.), and the like, in which more preferable example may be $C_1$-$C_4$ alkanoyloxy and the most preferable one may be acetoxy.

Suitable "halogen" may include chlorine, bromine, iodine and fluorine, in which more preferable example may be fluorine for $R^4$ and chlorine for X.

Suitable "mono- or di(lower)alkylcarbamoyl" means carbamoyl substituted by straight or branched lower alkyl as mentioned above, such as methylcarbamoyl, dimethylcarbamoyl, ethylcarbamoyl, diethylcarbamoyl, N-methyl-N-ethylcarbamoyl, propylcarbamoyl, dipropylcarbamoyl, isopropylcarbamoyl, butylcarbamoyl, pentylcarbamoyl, hexylcarbamoyl, and the like, in which more preferable example may be mono- or di($C_1$-$C_4$)alkylcarbamoyl and the most preferable one may be dimethylcarbamoyl.

Suitable "lower alkenyl" may include straight or branched one such as vinyl, allyl, and the like, in which more preferable example may be $C_2$-$C_4$ alkenyl and the most preferable one may be allyl.

Suitable "hydroxy(lower)alkoxy(lower)alkyl" may include aforementioned lower alkyl substituted by hydroxy(lower)alkyl as mentioned above, in which more preferable example may be hydroxy($C_1$-$C_4$)alkoxy($C_1$-$C_4$)alkyl and the most preferable one may be 2-(2-hydroxyethoxy)ethyl.

Suitable "lower alkyl optionally substituted by suitable substituent(s)" may include aforementioned lower alkyl group, which is substituted or unsubstituted by one or more, preferably one to three suitable substituent(s) selected from a group consisting of hydroxy, carbamoyl and halogen as mentioned above, in which more preferable example may be $C_1$-$C_4$ alkyl, hydroxy($C_1$-$C_4$)alkyl, halo($C_1$-$C_4$)alkyl and carbamoyl($C_1$-$C_4$)alkyl, and the most preferable one may be methyl, hydroxymethyl, fluoromethyl and carbamoylmethyl.

Suitable "heterocyclic group" means saturated or unsaturated, monocyclic or polycyclic heterocyclic group containing at least one hetero-atom such as an oxygen, sulfur, nitrogen atom and the like.

Preferable heterocyclic group may be heterocyclic group such as:

unsaturated 3 to 8-membered, preferably 5 or 6-membered heteromonocyclic group containing 1 to 4 nitrogen atom(s), for example, pyrrolyl, pyrrolinyl, imidazolyl, pyrazolyl, pyridyl, and its N-oxide, pyrimidyl, pyrazinyl, pyridazinyl, triazolyl (e.g., 4H-1,2,4-triazolyl, 1H-1,2,3-triazolyl, 2H-1,2,3-triazolyl, etc.), tetrazolyl (e.g., 1H-tetrazolyl, 2H-tetrazolyl, etc.), dihydrotriazinyl (e.g., 4,5-dihydro-1,2,4-triazinyl, 2,5-dihydro-1,2,4-triazinyl, etc.), etc.;

saturated 3 to 8-membered, preferably 5 or 6-membered heteromonocyclic group containing 1 to 4 nitrogen atom(s), for example, azetidinyl, pyrrolidinyl, imidazolidinyl, piperidinyl, pyrazolidinyl, piperazinyl, etc;

unsaturated condensed, preferably 5 or 6-membered heterocyclic group containing 1 to 5 nitrogen atom(s), for example, indolyl, isoindolyl, indolizinyl, benzimidazolyl, quinolyl, isoquinolyl, indazolyl, benzotriazolyl, tetrazolopyridyl, tetrazolopyridazinyl (e.g., tetrazolo[1,5-b]pyridazinyl, etc.), dihydrotriazolopyridazinyl, etc.;

unsaturated 3 to 8-membered, preferably 5 or 6-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.), etc.;

saturated 3 to 8-membered, preferably 5 or 6-membered heteromonocyclic group containing 1 to 2 oxygen atom(s) and 1 to 3 nitrogen atom(s), for example, morpholinyl, etc.;

unsaturated condensed, preferably 5 or 6-membered heterocyclic group containing 1 to 2 oxygen atom(s) and 1 to 3 nitrogen atom(s), for example, benzoxazolyl, benzoxadiazolyl, etc.;

unsaturated 3 to 8-membered, preferably 5 or 6-membered heteromonocyclic group containing 1 to 2 sulfur atom(s) and 1 to 3 nitrogen atom(s), for example, thiazolyl, thiazolinyl, thiadiazolyl (e.g., 1,2,4-thiadiazolyl, 1,3,4-thiadiazolyl, 1,2,5-thiadiazolyl, 1,2,3-thiadiazolyl), etc.;

saturated 3 to 8-membered, preferably 5 or 6-membered heteromonocyclic group containing 1 to 2 sulfur atom(s) and 1 to 3 nitrogen atom(s), for example, thiazolidinyl, isothiazolidinyl, thiadiazolidinyl, etc.;

unsaturated 3 to 8-membered, preferably 5 or 6-membered heteromonocyclic group containing a sulfur atom, for example, thienyl, etc.;

unsaturated condensed, preferably 5 or 6-membered heterocyclic group containing 1 to 2 sulfur atom(s) and 1 to 3 nitrogen atom(s), for example, benzothiazolyl, benzothiadiazolyl, etc. and the like;

in which more preferable example may be saturated or unsaturated 5 or 6-membered heteromonocyclic group containing 1 to 2 sulfur atom(s) and 1 to 3 nitrogen atom(s), and the most preferable one may be thiazolyl (e.g. thiazol-2-yl, etc.).

More preferable example of $R^5$ thus defined may be hydrogen, $C_2$-$C_4$ alkenyl, $C_2$-$C_4$ alkenyloxycarbonyl, phenyl(or nitrophenyl)(C₁-C₄)alkoxycarbonyl, di(C₁-C₄)alkylcarbamoyl, (C₁-C₄) alkanimidoyl, N-(C₁-C₆)alkyl(C₁-C₄)alkanimidoyl, N-[hydroxy(C₁-C₄)alkoxy(C₁-C₄)alkyl](C₁-C₄)alkanimidoyl, N-cyano(C₁-C₄)alkanimidoyl, N-thiazolyl(or thiazolinyl or thiadiazolyl or thiazolidinyl or isothiazolidinyl or thiadiazolidinyl)(C₁-C₄)alkanimidoyl, C-hydroxy(or halo or carbamoyl)(C₁-C₄)alkanimidoyl, N,N-di(C₁-C₄)alkyliminio(C₁-C₄)alkyl, and a compound of the formula:

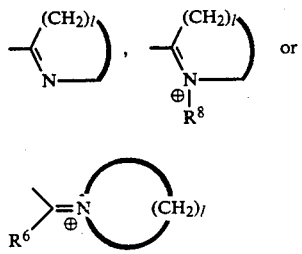

(wherein R⁶ is hydrogen or C₁-C₄ alkyl, R⁸ is C₁-C₄ alkyl, and l is an integer of 3 to 5 to form 5 or 6-membered N-containing heterocyclic ring, respectively), and the most preferable examples may be hydrogen, allyl, allyloxycarbonyl, bezyloxycarbonyl, dimethylcarbamoyl, formimidoyl, acetimidoyl, N-methyl(or ethyl or isopropyl)formimidoyl, N-methylacetimidoyl, N-[2-(2-hydroxyethoxy)ethyl]formimidoyl, N-cyanoformimidoyl, N-(thiazol-2-yl)formimidoyl, N-(1,3,4-thiadiazol-2-yl)formimidoyl, 2-hydroxy(or fluoro or carbamoyl)acetimidoyl, N,N-dimethyliminiomethyl, 1-pyrrolin-2-yl, 1-methyl-2-(1-pyrrolinio), and a compound of the formula:

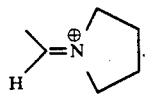

Suitable "N-containing aliphatic heterocyclic group optionally containing additional hetero atom(s)" means aforementioned "heterocyclic group", in which said heterocyclic group is non-aromatic heterocyclic group containing a nitrogen atom and optionally other hetero atom(s) such as sulfur, oxygen, nitrogen, etc.

Non-aromatic heterocyclic group may include aforementioned hetrocyclic group, in which the hetero ring is saturated or containing only non-conjugated double bond(s), and the like.

Preferable "N-containing aliphatic heterocyclic group optionally containing additional hetero atom(s)" thus defined may be:

3 to 8-membered, preferably 4 to 6-membered heteromonocyclic group containing 1 to 4 nitrogen atom(s), which has non-conjugated double bond(s) only in its ring, for example, pyrrolinyl, imidazolinyl, dihydropyridyl, tetrahydropyridyl-, dihydrotriazinyl, etc.;

saturated 3 to 8-membered, preferably 4 to 6-membered heteromonocyclic group containing 1 to 4 nitrogen atom(s), for example, azetidinyl, pyrrolidinyl, imidazolidinyl, piperidinyl, pyrazolidinyl, piperazinyl, etc;

saturated 3 to 8-membered, preferably 4 to 6-membered heteromonocyclic group containing 1 to 2 oxygen atom(s) and 1 to 3 nitrogen atom(s), for example, morpholinyl, etc.;

saturated 3 to 8-membered, preferably 4 to 6-membered heteromonocyclic group containing 1 to 2 sulfur atom(s) and 1 to 3 nitrogen atom(s), for example, thiazolidinyl, isothiazolidinyl, thiadiazolidinyl, thiomorpholinyl, etc.;

More preferable examples of N-containing aliphatic heterocyclic group optionally containing additional hetero atom(s) thus defined may be:

saturated 4 to 6-membered heteromonocyclic group containing 1 to 4 nitrogen atom(s);

saturated 4 to 6-membered heteromonocyclic group containing 1 to 2 oxygen atom(s) and 1 to 3 nitrogen atom(s);

saturated 4 to 6-membered heteromonocyclic group containing 1 to 2 sulfur atom(s) and 1 to 3 nitrogen atom(s); and a heterocyclic group of the formula:

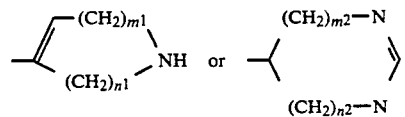

(wherein
m¹ and n¹ are each an integer of 0 to 3, and
m² and n² are each as integer of 0 to 2, with a proviso that $1 \leq m^1 + n^1 \leq 3$ and $0 \leq m^2 + n^2 \leq 2$)
and the like, and the most preferable one may be:
pyrrolinyl (e.g. 3-pyrrolin-3-yl, etc.);
imidazolinyl (e.g. 2-imidazolin-4-yl, etc.);
tetrahydropyridyl (e.g. 1,2,3,6-tetrahydropyridin-4-yl, 1,2,5,6-tetrahydropyridin-3-yl, etc.);
azetidinyl (e.g. azetidin-3-yl, etc.);
pyrrolidinyl (e.g. pyrrolidin-2-yl, pyrrolidin-3-yl, etc.);
piperidinyl [e.g. piperidin-2(or 3 or 4)-yl, etc.];
pyrazolidinyl (e.g. pyrazolidin-4-yl, etc.);
piperazinyl (e.g. piperazin-2-yl, etc.);
morpholinyl [e.g. morpholin-2(or 3)-yl, etc.];
thiazolidinyl (e.g. thiazolidin-4-yl, etc.);
thiomorpholinyl (e.g. thiomorpholin-3-yl, etc.);
and the like.

In case that the "N-containing aliphatic heterocyclic group optionally containing additional hetero atom(s)" is imiazolinyl, it is well known that there are tautomeric isomers as shown, for example, by the following equilibrium:

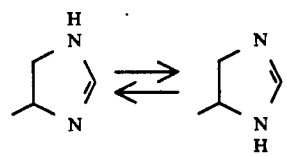

All of the above and the other tautomeric isomers are included within the scope of the present invention, and in the present specification, however, the object and intermediary compounds which include the group of such tautomeric isomers are represented by using one of the expressions therefor, for example, 2-imidazolin-4-yl and the formula:

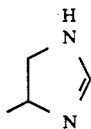

only for convenient sake.

The processes for the preparation of the object compound (I) of the present invention are explained in detail in the following.

(1) Process 1:

The compound (I) or salts thereof can be prepared by cyclizing the compound (II) or salts thereof.

Suitable salts of the compound (II) may be the same as those for the compound (I).

This reaction is usually carried out in a conventional solvent which does not adversely influence the reaction such as dioxane, hexamethylphosphoramide, benzene, toluene, xylene, dimethylsulfoxide, N,N-dimethylformamide, pyridine, etc., or a mixture thereof.

The reaction temperature of this reaction is not critical and the reaction is usually carries out under form warming to heating.

(2) Process 2:

The compound (I-b) or salts thereof can be prepared by subjecting the compound (I-a) or salts thereof to removal reaction of the carboxy-protective group $R_a^1$.

Suitable salts of the compounds (I-a) and (I-b) may be the same as those for the compound (I).

The present reaction is usually carried out be a conventional method such as hydrolysis, reduction, and the like.

(i) Hydrolysis:

Hydrolysis is preferably carried out in the presence of a base or an acid. Suitable base may include an alkali-metal hydroxide (e.g. sodium hydroxide, potassium hydroxide, etc.), an alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride, etc.), alkali metal alkoxide (e.g. sodium methoxide, sodium ethoxide, potassium t-butoxide, etc.), an alkali metal carbonate (e.g. sodium carbonate, potassium carbonate, etc.), and alkaline earth metal carbonate (e.g. magnesium carbonate, calcium carbonate, etc.), an alkali metal bicarbonate (e.g. sodium bicarbonate, potassium bicarbonate, etc.), and the like.

Suitable acid may include an organic acid (e.g. formic acid, acetic acid, propionic acid, trifluoroacetic acid, benzenesulfonic acid, p-toluenesulfonic acid, etc.) and an inorganic acid (e.g. hydrochloric acid, hydrobromic acid, sulfuric acid, phosphoric acid, etc.). The acidic hydrolysis using trifluoroacetic acid is usually accelerated by addition of cation trapping agent (e.g. phenol, anisole, etc.).

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base or acid can be also used as the solvent.

The reaction temperature is not critical and the reaction is usually carried out under from cooling to heating.

(ii) Reduction:

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, palladium hydroxide on carbon, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

In case that the catalytic reduction is applied, the reaction is preferably carried out around neutral condition.

This reaction is usually carried out in a conventional solvent which does not adversely influence the reaction such as water, alcohol (e.g. methanol, ethanol, propanol, etc.), dioxane, tetrahydrofuran, acetic acid, buffer solution (e.g. phosphate buffer, acetate buffer, etc.), and the like, or a mixture thereof.

The reaction temperature is not critical and the reaction is usually carried out under from cooling to warming.

In case that the carboxy-protective group is allyl group, it can be deprotected by hydrogenolysis using a palladium compound.

Suitable palladium compound used in this reaction may be palladium on carbon, palladium hydroxide on carbon, palladium chloride, a palladium-ligand complex such as tetrakis(triphenylphosphine)palladium(0), bis(-dibenzylideneacetone)palladium(0), di[1,2-bis(diphenylphosphino)ethane]palladium(0), tetrakis(triphenyl phosphite)palladium(0), tetrakis(triethyl phosphite)palladium(0), and the like.

The reaction can preferably be carried out in the presence of a scavenger of allyl group generated in situ, such as amine (e.g. morpholine, N-methylaniline, etc.), an activated methylene compound (e.g. dimedone, benzoyl acetate, 2-methyl-3-oxovaleric acid, etc., a cyanohydrin compound (e.g. α-tetrahydropyranyloxybenzyl cyanide, etc.), lower alkanoic acid or a salt thereof (e.g. formic acid, acetic acid, ammonium formate, sodium acetate, etc.), N-hydroxysuccinimide, and the like.

This reaction can be carried out in the presence of a base such as lower alkylamine (e.g. butylamine, triethylamine, etc.), pyridine, and the like.

When palladium-ligand complex is used in this reaction, the reaction can preferably be carried out in the presence of the corresponding ligand (e.g. triphenylphosphine, triphenyl phosphite, triethyl phosphite, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., or a mixture thereof.

The removal reaction can be selected according to the kind of carboxy-protective group to be removed.

The present process includes within the scope thereof a case that the hydroxy-protective group on $R^2$ and $R^4$ and/or imino-protective group on $R^5$ are removed at the same time during the reaction.

(3) Process 3:

The compound (I-d) or salts thereof can be prepared by subjecting the compound (I-c) or salts thereof to removal reaction of the hydroxy-protective group on $R_a^2$.

Suitable salts of the compounds (I-c) and (I-d) may be the same as those for the compound (I).

This reaction is usually carried out be a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the hydroxy-protective group is tri(-lower)alkylsilyl, the removal of this protective group can also be carried out in the presence of tetra(lower)alkylammonium fluoride (e.g. tetrabutylammonium fluoride, etc.).

The present process includes within the scope thereof a case that the carboxy-protective group on $R^1$ and/or imino-protective group on $R^5$ and/or hydroxy-protective group on $R^4$ are removed at the same time during the reaction.

(4) Process 4:

The compound (I-f) or salts thereof can be prepared by subjecting the compound (I-e) or salts thereof to removal reaction of the imino-protective group of $R_a^5$.

Suitable salts of the compound (I-e) may be salts with bases such as those given for the compound (I).

Suitable salts of the compound (I-f) may be the same at those for the compound (I).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or hydroxy-protective group(s) on $R^1$ and/or $R^2$ and/or hydroxy-protective group on $R^4$ are removed at the same time during the reaction.

(5) Process 5:

The compound (I-h) or salts thereof can be prepared by reducing the compound (I-g) or salts thereof.

Suitable salts of the compounds (I-g) and (I-h) may be the same as those for the compound (I).

The method of reduction and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or hydroxy-protective group(s) on $R^1$ and/or $R^2$, and/or hydroxy- and/or imino-protective group(s) on $R^4$ and/or of $R^5$ are removed at the same time during the reaction.

(6) Process 6:

The compound (I-i) or salts thereof can be prepared by reacting the compound (I-f) or salts thereof with the compound (XIII) or salts thereof.

Suitable salts of the compound (I-i) may be the same as those for the compound (I).

Suitable salts of the compound (XIII) may be the same acid addition salts as those given for the compound (I).

Among the compound (XIII), a compound of the formula:

$$R^{10}-O \underset{R^6}{\overset{}{\searrow}}=\overset{\oplus}{N}\underset{R^8}{\overset{R^7}{\nearrow}}$$

can be prepared in situ by reacting a compound of the formula:

$$O \underset{R^6}{\overset{}{\searrow}}-N\underset{R^8}{\overset{R^7}{\nearrow}}$$

with a sulfuric acid derivative having, for example, the formula:

$$(R^{10})_2SO_4.$$

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

This reaction can be carried out in the presence of an organic or inorganic base such as those given in the explanation of Process 2.

The reaction temperature is not critical, and the reaction is usually carried out under from cooling to warming.

(7) Process 7:

The compound (I-k) or salts thereof can be prepared by subjecting the compound (I-j) or salts thereof to removal reaction of the hydroxy-protective group on $R_a^4$.

Suitable salts of the compounds (I-j) and (I-k) may be the same as those for the compound (I).

This reaction is usually carried out by a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the hydroxy-protective group is tri(-lower)alkylsilyl, the removal of this protective group can also be carried out in the presence of tetra(lower)alkylammonium fluoride (e.g. tetrabutylammonium fluoride, etc.).

The present process includes within the scope thereof a case that the carboxy-protective group on $R^1$ and/or imino-protective group of $R^5$ and/or hydroxy-protective group on $R^2$ are removed at the same time during the reaction.

(8) Process 8:

The compound (I-m) or salts thereof can be prepared by reacting the compound (I-l) or salts thereof with Palladium compound in the presence of about 1 equivalent of a scavenger.

Suitable salts of the compounds (I-l) and (I-m) may be the same as those for the compound (I).

Suitable Palladium compound used in this reaction may be palladium on carbon, palladium hydroxide on carbon, palladium chloride, a palladium-ligand complex such as tetrakis(triphenylphosphine)palladium(0), bis(dibenzylideneacetone)palladium(0), di[1,2-bis(diphenylphosphino)ethane]palladium(0), tetrakis(triphenyl phosphite)palladium(0), tetrakis(triethyl phosphite)palladium(0), and the like.

The reaction can preferably be carried out in the presence of about 1 equivalent of a scavenger for lower alkenyl group generated in situ, such as amine (e.g. morpholine, N-methylaniline, etc.), an activated methylene compound (e.g. dimedone, benzoyl acetate, 2-methyl-3-oxovaleric acid, etc.), a cyanohydrin compound (e.g. α-tetrahydropyranyloxybenzyl cyanide, etc.), alkanoic acid or a salt thereof (e.g. formic acid, acetic acid, ammonium formate, sodium acetate, sodium 2-ethylhexanoate, etc.), N-hydroxysuccinimide, and the like.

This reaction can be carried out in the presence of a base such as lower alkylamine (e.g. butylamine, triethylamine, etc.), pyridine, and the like.

When palladium-ligand complex is used in this reaction, the reaction can preferably be carried out in the presence of the corresponding ligand e.g. triphenylphosphine, triphenyl phosphite, triethyl phosphite, etc.).

This reaction is usually carried out in a conventional solvent which does not adversely influence the reaction such as water, methanol, ethanol, propanol, dioxane, tetrahydrofuran, acetonitrile, chloroform, dichloromethane, dichloroethane, ethyl acetate, etc., or a mixture thereof.

(9) Process 9:

The compound (I-n) or salts thereof can be prepared by reacting the compound (I-m) or salts thereof with a lower alkylating agent.

Suitable salts of the compound (I-n) may be the same acid addition salts as those given for the compound (I).

Suitable alkylating agent used in this reaction may include a conventional one which is capable of alkylating a hydroxy group to an alkoxy group such as dialkyl sulfate (e.g. dimethyl sulfate, diethyl sulfate, etc.), alkyl sulfonate (e.g. methyl sulfonate, etc.), alkyl halide (e.g. methyl iodide, ethyl iodide, propyl bromide, etc.), diazoalkanes (e.g. diazomethane, diazoethane, etc.), and the like.

This reaction is preferably carried out in the presence of an inorganic or organic base such as those given in the explanation of the Process 2.

Further, this reaction is usually carried out in a conventional solvent which does not adversely influence the reaction such as water, acetone, dichloromethane, methanol, ethanol, propanol, pyridine, N,N-dimethylformamide, or a mixture thereof.

(10) Process 10

The compound (I-p) can be prepared by reacting the compound (I-o) or salts thereof with the compound (XIII-a) or salts thereof.

Suitable salts of the compound (I-o) may be the same as those for the compound (I).

Suitable salts of the compound (XIII-a) may be the same acid addition salts as those given for the compound (I).

Suitable examples of the compound (XIII-a) may be lower alkyl formimidate (e.g. methyl formimidate, ethyl formimidate, etc.), ar(lower)alkyl formimidate (e.g. benzyl formimidate, etc.), and the like.

This reaction is usually carried out in a conventional solvent which does not adversely influence the reaction such as tetrahydrofuran, dioxane, water, methanol, ethanol, buffer solution (e.g. phosphate buffer, etc.), etc., or a mixture thereof.

This reaction can be carried out in the presence of an organic or inorganic base such as those given in the explanation of Process 2.

The reaction temperature is not critical, and the reaction is usually carried out under from cooling to warming.

(11) Process 11:

The compound (I-q) or salts thereof can be prepared by reacting the compound (XI) or salts thereof with the compound (XIII-b) or salts thereof.

Suitable salts of the compound (I-q) may be the same as those for the compound (I).

This reaction is usually carried out in substantially the same manner as that of Process 10.

The method and the reaction conditions (e.g. reaction temperature, solvent, etc.) are substantially the same as those illustrated for Process 10, and therefore are to be referred to said explanation.

Suitable example of the compound (XIII-b) may be lower alkyl (lower)alkanimidate (e.g. methyl formimidate, ethyl formimidate, methyl acetimidate, ethyl acetimidate, ethyl propionimidate, ethyl butyrimidate, ethyl isovalerimidate, ethyl pentanimidate, ethyl hexanimidate, etc.), ar(lower)alkyl (lower)alkanimidate (e.g. benzyl formimidate, benzyl acetimidate, benzyl propionimidate, benzyl butyrimidate, benzyl isovalerimidate, benzyl pentanimidate, benzyl hexanimidate, etc.), and the like, or an acid addition salt thereof.

The object compound (I) obtained according to the Processes 1 to 11, can be isolated and purified in a conventional manner, for example, extraction, precipitation, fractional crystallization, recrystallization, chromatography, and the like.

Methods for preparing the new starting compound (II) or salts thereof are explained in detail in the following.

(A) Method A :

The compound (V) or salts thereof can be prepared by reacting the compound (III) with the compound (IV) or salts thereof.

Suitable salts of the compound (IV) and (V) may be the same acid addition salts as those for the compound (I).

The compound (IV) or salts thereof can be prepared from the known compounds by a conventional manner or that described in the Preparations of the present specification.

This reaction can be carried out in the presence of a base such as alkali metal hydroxide (e.g. sodium hydroxide, potassium hydroxide, etc.), alkaline earth metal hydroxide (e.g. magnesium hydroxide, calcium hydroxide, etc.), alkali metal hydride (e.g. sodium hydride, potassium hydride, etc.), alkaline earth metal hydride (e.g. calcium hydride etc.), alkali metal alkoxide (e.g. sodium methoxide, sodium ethoxide, potassium t-butoxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), and the like.

This reaction can preferably be carried out in the presence of an enolizating agent. Suitable enolizating agent may include tri(lower)alkylsilyl trihalo(lower)alkanesulfonate, preferably tri($C_1$-$C_4$)alkylsilyl trihalo($C_1$-$C_4$)alkanesulfonate e.g. trimethylsilyl trifluoromethanesulfonate, etc.), tin compound such as stannous (lower)alkylsulfonate which may have halogen(s), preferably stannous polyhalo($C_1$-$C_4$)alkylsulfonate (e.g. stannous trifluoromethanesulfonate, etc.), and the like.

This reaction is usually carried out in a conventional solvent which does not adversely influence the reaction such as water, dichloromethane, alcohol (e.g. methanol, ethanol, etc.), tetrahydrofuran, dioxane, acetone, etc., or a mixture thereof. A liquid base can be also used as the solvent.

The reaction temperature is not critical and the reaction is usually carried out under from cooling to warming.

(B) Method B :

The compound (VII) or salts thereof can be prepared by reacting the compound (V) or salts thereof with the compound (VI) or its reactive equivalent.

Suitable salts of the compound (VII) may be the same as those for the compound (I).

Suitable example of the compound (VI) may be glyoxylic acid, in which the carboxy group may be protected by a conventional carboxy-protective group to form esterified carboxy as mentioned above.

Suitable reactive equivalents of the compound (VI) may include monohydrate thereof, and the like.

This reaction can preferably be carried out with azeotropic removal of water produced in situ. The azeotropic removal of the water can be carried out by a conventional method (e.g. azeotropic distillation, etc.).

This reaction is usually carried out in a conventional solvent which does not adversely influence the reaction such as water, dichloromethane, alcohol (e.g. methanol, ethanol, etc.), tetrahydrofuran, dioxane, acetone, benzene, toluene, xylene, etc., or a mixture thereof.

The reaction temperature is not critical and the reaction is usually carried out under from warming to heating.

(C) Method C:

The compound (II) or salts thereof can be prepared by reacting the compound (VII) or a reactive derivative at the hydroxy group thereof, or salts thereof with the compound (VIII).

Suitable reactive derivative at the hydroxy group of the compound (VII) may include a conventional one such as halide (e.g. chloride, bromide, iodide, etc.), sulfonate (e.g. methanesulfonate, benzenesulfonate, toluenesulfonate, etc.) and the like, in which more preferable example may be halide.

Preferable example of the compound (VIII) may be triphenylphosphine, tri($C_1$-$C_4$)alkyl phosphite (e.g. triethyl phosphite, etc.), and the like.

This reaction can be carried out in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g. magnesium carbonate, calcium carbonate, etc.), tri(lower)alkylamine (e.g. trimethylamine, triethylamine, N,N-diisopropyl-N-ethylamine, etc.), pyridine compounds [e.g. pyridine, picoline, lutidine, N,N-di(lower)alkylaminopyridine such as N,N-dimethylaminopyridine, etc.], quinoline, imidazole, N-lower alkylmorphorine (e.g. N-methylmorphorine, etc.), N-lower alkylpiperidine (e.g. N-ethylpiperidine, etc.), N,N-di(lower)alkylbenzylamine (e.g. N,N-dimethylbenzylamine, etc.), and the like.

This reaction is usually carried out in a conventional solvent which does not adversely influence the reaction such as dioxane, acetonitrile, chloroform, dichloromethane, hexamethylphosphoramide, dichloroethane, tetrahydrofuran, ethyl acetate, dimethyl sulfoxide, N,N-dimethylformamide, pyridine, etc., or a mixture thereof.

The reaction temperature of this reaction is not critical and the reaction is usually carried out under from cooling to warming.

(D) Method D:

The compound (X) or salts thereof can be prepared by reacting the compound (V) or salts thereof with the compound (IX) or salts thereof.

Suitable salts of the compound (X) may be the same as those for the compound (I).

Suitable salts of the compound (IX) may be the same as those for the compound (I-e).

Suitable example of the compound (IX) may be oxalyl halide, in which the carboxy group may be protected by a conventional carboxy-protective group as mentioned above.

This reaction can be carried out in the presence of a base as mentioned in Method C.

This reaction is usually carried out in a conventional solvent which does not adversely influence the reaction such as dioxane, acetonitrile, chloroform, dichloromethane, hexamethylphosphoramide, dichloroethane, tetrahydrofuran, ethyl acetate, dimethyl sulfoxide, N,N-dimethylformamide, pyridine, etc., or a mixture thereof.

The reaction temperature of this reaction is not critical and the reaction is usually carried out under from cooling to warming.

(E) Method E:

The compound (II) or salts thereof can be prepared by reacting the compound (X) or salts thereof with the compound (VIII).

This reaction is usually carried out in a conventional solvent which does not adversely influence the reaction such as dioxane, acetonitrile, chloroform, dichloromethane, hexamethylphosphoramide, dichloroethane, tetrahydrofuran, ethyl acetate, dimethyl sulfoxide, N,N-dimethylformamide, pyridine, benzene, toluene, xylene, etc., or a mixture thereof.

The reaction temperature of this reaction is not critical and the reaction is usually carried out under from warming to heating.

(F) Method F:

The compound (XII) or salts thereof can be prepared by cyclizing the compound (II-a) or salts thereof.

Suitable salts of the compounds (II-a) and (XII) may be the same as those for the compound (I).

The method of cyclization and the reaction conditions (e.g. reaction temperature, solvent, etc.) are substantially the same as those illustrated for cyclization reaction of the compound (II) in Process 1, and therefore are to be referred to said explanation.

(G) Method G:

The compound (XII-b) or salts thereof can be prepared by subjecting the compound (XII-a) or salts thereof to removal reaction of the carboxy-protective group on $R_a^1$.

Suitable salts of the compound (XII-a) may be the same as those for the compound (I-a).

Suitable salts of the compound (XII-b) may be the same as those for the compound (XII).

The present reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the hydroxy-protective group on $R^2$ and $R^4$ and/or imino-protective group of $R^5$ are removed at the same time during the reaction.

(H) Method H:

The compound (XII-d) or salts thereof can be prepared by subjecting the compound (XII-c) or salts thereof to removal reaction of the hydroxy-protective group on $R_a^2$.

Suitable salts of the compounds (XII-c) and (XII-d) may be the same as those for the compound (XII).

This reaction is usually carried out by a conventional method such as hydrolysis, reduction and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

In case that the hydroxy-protective group is tri(-lower)alkylsilyl, the removal of this protective group can also be carried out in the presence of tetra(lower)alkylammonium fluoride (e.g. tetrabutylammonium fluoride, etc.).

The present process includes within the scope thereof a case that the carboxy-protective group on $R^1$ and/or amino-protective group(s) on $R^{12}$ and/or $R^{13}$ are removed at the same time during the reaction.

(I) Method I:

The compound (XII-e) or salts thereof can be prepared by subjecting the compound (XII) or salts thereof to removal reaction of the amino-protective group(s) on $R^{12}$ and/or $R^{13}$.

Suitable salts of the compound (XII-e) may be the same as those for the compound (XII).

This reaction is usually carried out by a conventional method such as hydrolysis, reduction, and the like.

The method of hydrolysis and reduction, and the reaction conditions (e.g. reaction temperature, solvent, etc.) are substantially the same as those illustrated for removal reaction of the carboxy-protective group of the compound (I-a) in Process 2, and therefore are to be referred to said explanation.

The present process includes within the scope thereof a case that the carboxy- and/or hydroxy-protective group(s) on $R^1$ and/or $R^2$ are removed at the same time during the reaction.

The object compound (I) and pharmaceutically acceptable salts thereof of the present invention are novel and exhibit high antimicrobial activity, inhibiting the growth of a wide variety of pathogenic microorganisms including Gram-positive and Gram-negative microorganisms and are useful as antimicrobial agents.

Now in order to show the utility of the object compound (I), the test data on antimicrobial activity of the representative compound of the compound (I) of this invention is shown in the following.

IN VITRO ANTIMICROBIAL ACTIVITY

Test Method in vitro Antimicrobial Activity was determined by the two-fold agar-plate dilution method as described below.

One loopful of an overnight culture of a test strain in Trypticase-soy broth ($10^6$ viable cells per ml) was streaked on heart infusion agar (HI-agar) containing graded concentrations of the test compound, and the minimal inhibitory concentration (MIC) was expressed in terms of µg/ml after incubation at 37° C. for 20 hours.

Test Compound

The compound of Example 12.

Test Result

| Test Strain | MIC (µg/ml) |
|---|---|
| S. aureus 6 | ≦0.025 |

For therapeutic administration, the object compound (I) and the pharmaceutically acceptable salts thereof of the present invention are used in the form of conventional pharmaceutical preparation which contains said compound, as an active ingredient, in admixture with pharmaceutically acceptable carriers such as an organic or inorganic solid or liquid excipient which is suitable for oral, parenteral and external administration. The pharmaceutical preparations may be in solid form such as tablet, granule, powder, capsule, or liquid form such as solution, suspension, syrup, emulsion, lemonade, and the like.

If needed, there may be included in the above preparations auxiliary substances, stabilizing agents, wetting agents and other commonly used additives such as lactose, stearic acid, magnesium stearate, terra alba, sucrose, corn starch, talc, gelatin, agar, pectin, peanut oil, olive oil, cacao butter, ethylene glycol, tartaric acid, citric acid, fumaric acid, and the like.

While the dosage of the compound (I) may vary from and also depend upon the age, conditions of the patient, a kind of diseases, a kind of the compound (I) to be applied, etc. In general, amount between 1 mg and about 4,000 mg or even more per day may be administered to a patient. An average single dose of about 1 mg, 10 mg, 50 mg, 100 mg, 250 mg, 500 mg, 1000 mg, 20,000 mg, of the object compound (I) of the present invention may be used in treating diseases infected by pathogenic microorganisms.

The following Preparations and Examples are given for the purpose of illustrating this invention in more detail.

PREPARATION 1

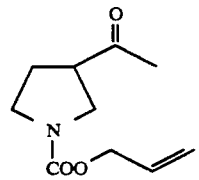

To a solution of 1-allyloxycarbonyl-3-hydroxymethylpyrrolidine (2.6 g) in acetone was added Jones reagent (1.25N, 20 ml) at ambient temperature. After stirring for 1 hour, isopropyl alcohol (10 ml) was added thereto. The resulting precipitate was removed by filtration and the filtrate was evaporated in vacuo. The residue was dissolved in dichloromethane, dicyclohexylcarbodiimide (0.79 g), Meldrum's acid (0.55 g), 4-methylaminopyridine (0.47 g) to the solution at 0° C. After stirring for 24 hours at ambient temperature, the resulting precipitate was removed by filtration. The filtrate was washed with 1N hydrochloric acid and evaporated in vacuo. The residue was dissolved in a mixture of acetic acid (10 ml) and water (7 ml), and the mixture was refluxed for 1 hour. Evaporation of the solvent gave a residue, which was taken up into ethyl acetate. The solution was washed in turn with saturated sodium bicarbonate and brine, dried over magnesium sulfate, and evaporated. The residue was chromatographed on silica gel eluting with a mixture of n-hexane and ethyl acetate (2:1, V/V) to give 3-acetyl-1-allyloxycarbonylpyrrolidine (2.01 g).

IR (CH$_2$Cl$_2$): 1680–1720 cm$^{-1}$.

NMR (CDCl$_3$, δ): 1.9–2.2 (2H, m), 2.22 (3H, s), 3.0–3.9 (5H, m), 4.28–4.35 (2H, m), 5.10–5.20 (2H, m), 5.90–6.10 (1H, m).

PREPARATION 2-1)

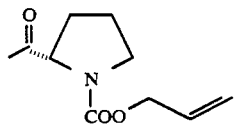

To a solution of (2S)-1-allyloxycarbonyl-2-carboxypyrrolidine (10 g) in dichloromethane (100 ml) were added dicyclohexylcarbodiimide (9.8 g), Meldrum's acid (6.8 g) and 4-dimethylaminopyridine (5.8 g) at 0° C. After stirring for 24 hours at ambient temperature, the resulting precipitate was removed by filtration. The filtrate was washed with 1N hydrochloric acid solution, evaporated in vacuo. The residue was dissolved in a mixture of acetic acid (80 ml) and water (60 ml), and refluxed for 1 hour. Evaporation of the solvent gave a residue, which was taken up into ethyl acetate. The solution was washed in turn with saturated sodium bicarbonate and brine, dried over magnesium sulfate, and evaporated. The residue was chromatographed on silica gel eluting with a mixture of n-hexane and ethyl acetate (2:1, V/V) to give (2S)-2-acetyl-1-allyloxycarbonylpyrrolidine (4.1 g).

IR (Neat): 1690–1720 cm$^{-1}$.

NMR (CDCl$_3$, δ): 1.78–2.00 (4H, m), 2.11, 2.19 (3H, each s), 3.42–3.69 (2H, m), 4.23–4.47 (1H, m), 4.48–4.62 (2H, m), 5.18–5.40 (2H, m), 5.79–6.03 (1H, m).

PREPARATION 2-2)

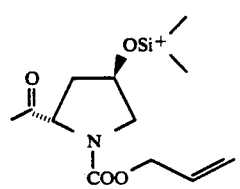

To a solution of (2S,4R)-1-allyloxycarbonyl-4-t-butyldimethylsilyloxy-2-carboxypyrrolidine (15 g) in dichloromethane (150 ml) were added dicyclohexylcarbodiimide (11.5 g), Meldrum's acid (8.0 g) and 4-dimethylaminopyridine (6.8 g) at 0° C. After stirring for 24 hours at ambient temperature, the resulting precipitate was removed by filtration. The filtrate was washed with 1N hydrochloric acid solution, and evaporated in vacuo. The residue was dissolved in a mixture of acetic acid (80 ml) and water (60 ml), and refluxed for 1 hour. Evaporation of the solvent gave a residue, which was taken up into ethyl acetate. The solution was washed in turn with saturated sodium bicarbonate and brine, dried over magnesium sulfate, and evaporated. The residue was dissolved in dimethylformamide (60 ml) and then imidazole (8.7 g) and t-butyldimethylsilyl chloride (8.7 g) were added thereto at ambient temperature. After stirring for 10 hour, the mixture was poured into water (200 ml), extracted with ethyl acetate (100 ml×2), dried over magnesium sulfate and evaporated. The residue was chromatographed on silica gel eluting with a mixture of n-hexane and ethyl acetate (2:1, V/V) to give (2S,4R)-2-acetyl-1-allyloxycarbonyl-4-t-butyldimethylsilyloxypyrrolidine (10.6 g).

IR (Neat): 1700–1720 cm$^{-1}$.

NMR (CDCl$_3$, δ): 0.03 (6H, s), 0.92 (9H, s), 1.70–2.10 (2H, m), 2.06, 2.14 (3H, each s), 3.25–3.60 (3H, m), 4.23–4.61 (3H, m), 5.02–5.24 (2H, m), 5.68–6.00 (1H, m).

The following compounds were obtained in substantially the same manner as that of Preparation 2-1).

PREPARATION 2-3)

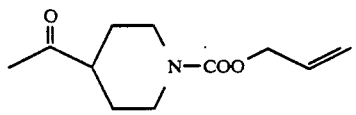

IR (CH$_2$Cl$_2$): 1680–1710 cm$^{-1}$.

NMR (CDCl$_3$, δ): 1.4–1.7 (2H, m), 1.8–2.0 (2H, m), 2.17 (3H, s), 2.3–2.6 (2H, m), 2.7–3.0 (2H, m), 3.9–4.3 (2H, m), 4.58–4.61 (2H, m), 5.1–5.4 (2H, m), 5.8–6.0 (2H, m).

PREPARATION 2-4)

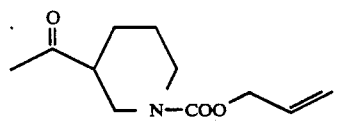

IR (Neat): 1690–1710 cm$^{-1}$.

NMR (CDCl$_3$, δ): 1.4–2.2 (4H, m), 2.19 (3H, s), 2.4–2.6 (1H, m), 2.7–3.2 (2H, m), 3.8–4.3 (2H, m), 4.50–4.60 (2H, m), 5.2–5.4 (2H, m), 5.8–6.1 (1H, m).

PREPARATION 3

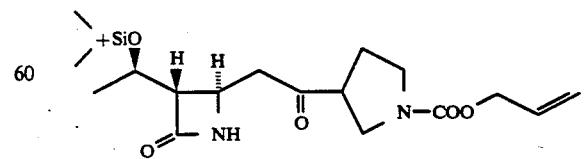

To a solution of (3R,4R)-4-acetoxy-3-[(1R)-1-t-butyldimethylsilyloxyethyl]-2-oxoazetidine (2.2 g) and triethylamine (1.1 ml) in dichloromethane (20 ml) was added trimethylsilyl trifluoromethanesulfonate (1.5 ml) at −60° C. under nitrogen, and the mixture was stirred at 0° C. for 30 minutes (Solution A). To a solution of 4-acetyl-1-allyloxycarbonylpyrrolidine (1.0 g) and triethylamine (0.71 ml) in dichloromethane (10 ml) was added trimethylsilyl trifluoromethanesulfonate (0.98 ml) at −60° C. under nitrogen and the resulting mixture was stirred at 0° C. for 30 minutes. To this mixture was added dropwise the Solution A at 0° C. under nitrogen, and the mixture was stirred for additional 4 hours at 0° C. The reaction mixture was taken up into a mixture of ethyl acetate and water and the mixture was stirred at ambient temperature for 2 hours. After adjusting pH to around 6.5 with aqueous sodium hydrogen carbonate, the organic layer was separated, washed with brine, dried over magnesium sulfate and evaporated in vacuo. The residue was chromatographed on silica gel eluting with a mixture of n-hexane and ethyl acetate (1:2, V/V) to give (3S,4R)-4-[2-(1-allyloxycarbonylpyrrolidin-3-yl)-2-oxoethyl]-3-[(1R)-1-t-butyldimethylsilyloxyethyl]-2-oxoazetidine (1.2 g).

IR (CH$_2$Cl$_2$): 1760, 1690–1710 cm$^{-1}$.

NMR (CDCl$_3$, δ): 0.1 (6H, s), 0.88 (9H, s), 1.22 (3H, d, J=7 Hz), 1.9–2.5 (2H, m), 2.7–3.0 (3H, m), 3.0–3.3 (1H, m), 3.3–3.7 (4H, m), 3.8–4.4 (2H, m), 4.5–4.7 (2H, m), 5.0–5.4 (2H, m), 5.6–6.2 (1H, m), 6.26 (1H, br s).

The following compounds were obtained in substantially the same manner as that of Preparation 3.

PREPARATION 4-1)

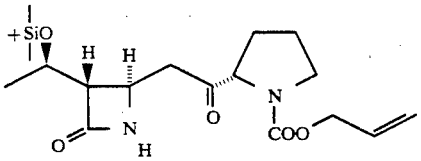

IR (CH$_2$Cl$_2$): 1760, 1690–1710 cm$^{-1}$.

NMR (CDCl$_3$, δ): 0.03 (6H, s), 0.91 (9H, s), 1.11–1.21 (3H, m), 1.69–2.30 (4H, m), 2.41–3.00 (3H, m), 3.39–3.65 (2H, m), 3.82–4.00 (1H, m), 4.02–4.41 (2H, m), 4.42–4.50 (2H, m), 5.08–5.38 (2H, m), 5.62–6.00 (1H, m). Preparation 4-2)

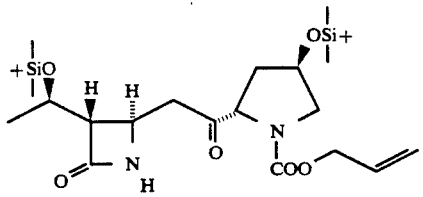

IR (CH$_2$Cl$_2$): 1760, 1690–1710 cm$^{-1}$.

NMR (CDCl$_3$, δ): 0.03 (12H, s), 0.092 (18H, s), 1.12–1.22 (3H, m), 2.44–2.92 (3H, m), 3.35–3.61 (2H, m), 4.29–4.62 (3H, m), 5.11–5.30 (2H, m), 5.60–6.00 (1H, m).

PREPARATION 4-3)

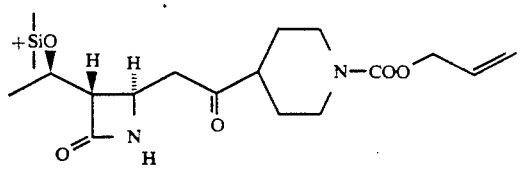

IR (CH$_2$Cl$_2$): 1750, 1690 cm$^{-1}$.

NMR (CDCl$_3$, δ): 0.05 (6H, s), 0.90 (9H, s), 1.15 (3H, d, J=6 Hz), 1.44–1.56 (2H, m), 1.76–1.81 (2H, m), 2.43–2.95 (6H, m), 3.82–4.13 (4H, m), 4.50–4.54 (2H, m), 5.11–5.27 (2H, m), 5.83–5.95 (1H, m), 6.05 (1H, br s).

PREPARATION 4-4)

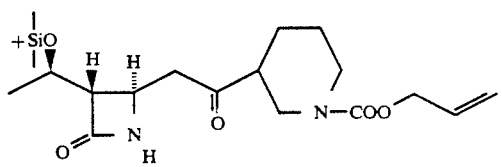

IR (CH$_2$Cl$_2$): 1755, 1690 cm$^{-1}$.

NMR (CDCl$_3$, δ): 0.02 (6H, s), 0.90 (9H, s), 1.14 (3H, d, J=6 Hz), 1.2–2.0 (4H, m), 2.4–3.2 (6H, m), 3.7–4.2 (4H, m), 4.4–4.6 (2H, m), 5.0–5.3 (2H, m), 5.7–6.2 (2H, m).

PREPARATION 5-1)

To a solution of trimethylsilylacetylene (17 ml) in tetrahydrofuran (100 ml) were added successively a solution of n-butyllithium in n-hexane (1.50M, 81 ml) and a solution of 1-acetyl-4-piperidone (11.5 g) in tetrahydrofuran (15 ml) at −78° C. After stirring at −78° C. for 30 minutes, to the mixture was added acetic acid (5.0 ml) and the resultant mixture was taken up into a mixture of aqueous ammonium chloride (300 ml) and ethyl acetate (300 ml) at 0° C. The organic layer was separated and washed with brine, dried over magnesium sulfate. Evaporation of the solvent gave a crystalline which was collected by filtration, and washed with n-hexane to give 1-acetyl-4-hydroxy-4-(2-trimethylsilylethynyl)piperidine (14.48 g).

IR (Nujol): 3160, 1610 cm$^{-1}$.

NMR (CDCl$_3$, δ): 0.17 (9H, s), 1.50–2.22 (4H, m), 2.08 (3H, s), 2.53 (1H, s), 3.13–4.30 (4H, m).

PREPARATION 5-2)

To a solution of 1-acetyl-4-hydroxy-4-(2-trimethylsilylethynyl)piperidine (13 g) in a mixture of tetrahydrofuran (100 ml), water (25 ml) and N,N-dimethylformamide (10 drops) were added mercuric sulfate (1.6 g) and sulfuric acid (10 drops), and the resultant mixture was stirred at ambient temperature for 15 hours. After adjusting pH to around 8 with sodium hydrogen carbonate, the reaction mixture was filtered with "florisil" (trademark, made by Floridin Co.) and the residue was washed with ethyl acetate and tetrahydrofuran. Filtrate and washings were combined and evaporated in vacuo, and the residue was dissolved in ethyl acetate, dried over magnesium sulfate. Evaporation of the solvent gave 1,4-diacetyl-4-hydroxypiperidine (8.75 g).

IR (Nujol): 3350, 1700, 1610 cm$^{-1}$.

NMR (CDCl$_3$, δ): 1.40–2.00 (4H, m), 2.15 (3H, s), 2.27 (3H, s), 2.80–3.30 (1H, br s), 3.30–4.20 (3H, m), 4.20–5.00 (1H, m).

PREPARATION 5-3)

1,4-Diacetyl-4-hydroxypiperidine (0.2 g) was dissolved in 1N hydrochloric acid (4 ml) and the solution was heated at 100° C. for 15 hours. After cooling to 0° C., the reaction mixture was diluted with a mixture of tetrahydrofuran (10 ml) and water (10 ml). To the mixture was added dropwise at 0° C. a solution of allyl chloroformate (0.15 ml) in tetrahydrofuran (2 ml) while adjusting pH to around 10 with aqueous potassium hydride. After stirring at 0° C. for 30 minutes, the reaction mixture was diluted with a mixture of ethyl acetate and water. The organic layer was separated, washed in turn with water and brine, and dried over magnesium sulfate. Evaporation of the solvent gave a residue, which was chromatographed on silica gel (10 g) eluting with a mixture of n-hexane and ethyl acetate (9:1–1:1, V/V) to give 4-acetyl-1-allyloxycarbonyl-4-hydroxypiperidine (0.26 g).

IR (Neat): 3420, 1690 cm$^{-1}$.

NMR (CDCl$_3$, δ): 1.20–1.63 (2H, m), 1.75–2.15 (2H, m), 2.26 (3H, s), 3.00–3.45 (2H, m), 3.82 (1H, br s), 3.96–4.33 (2H, m), 4.50–4.77 (2H, m), 5.10–5.50 (2H, m), 5.74–6.20 (1H, m).

PREPARATION 5-4)

To a solution of 4-acetyl-1-allyloxycarbonyl-4-hydroxypiperidine (0.2 g) in pyridine (4.0 ml) was added dropwise thionyl chloride (0.12 ml) at −20° C. The resultant mixture was allowed to warm to ambient temperature for 1 hour and stirred for another period of 2 hours. Evaporation of the mixture in vacuo gave a residue which was taken up into a mixture of ethyl acetate and water. The organic layer was separated, washed with brine, dried over magnesium sulfate and evaporated. The residue was chromatographed on silica gel (10 g) eluting with a mixture of n-hexane and ethyl acetate (9:1–1:1 V/V) to give 4-acetyl-1-allyloxycarbonyl-1,2,3,6-tetrahydropyridine (69 mg).

NMR (CDCl$_3$, δ): 2.26–2.60 (2H, m), 2.35 (3H, s), 3.60 (2H, t, J=6 Hz), 4.10–4.30 (2H, m), 4.50–4.75 (2H, m), 5.12–5.45 (2H, m), 5.70–6.25 (1H, m), 6.65–6.86 (1H, m).

PREPARATION 5-5)

To a solution of 4-acetyl-1-allyloxycarbonyl-1,2,3,6-tetrahydropyridine (1.33 g) and triethylamine (1.06 ml) in dichloromethane (50 ml) was added trimethylsilyl trifluoromethanesulfonate (2.2 ml) at 0° C. After stirring for 4 hours, a solution of (3R,4R)-4-acetoxy-3-[(1R)-1-t-butyldimethylsilyloxyethyl]-2-oxoazetidine (1.82 g) and zinc bromide (1.86 g) in ethyl acetate (10 ml) was added to the mixture, and the resultant mixture was stirred for 1 hour at 0° C. The reaction mixture was taken up into a mixture of ethyl acetate (200 ml) and water (200 ml). After adjusting pH to 4 with aqueous sodium hydrogen carbonate, the organic layer was separated, washed with brine, dried over magnesium sulfate. Evaporation of the solvent gave a residue, which was chromatographed on silica gel (40 g) eluting with a mixture of n-hexane and ethyl acetate (9:1–3:7, V/V) to give (3S,4R)-4-[2-(1-allyloxycarbonyl-1,2,3,6-tetrahydropyridin-4-yl)-2-oxoethyl]-3-[(1R)-1-t-butyldimethylsilyloxyethyl]-2-oxoazetidine (1.80 g).

IR (CH$_2$Cl$_2$): 3420, 1760, 1700 cm$^{-1}$.

NMR (CDCl$_3$, δ): 0.10 (6H, s), 0.91 (9H, s), 1.25 (3H, d, J=7 Hz), 2.20–2.54 (2H, m), 2.76 (1H, dd, J=7, 18 Hz), 2.80 (1H, dd, J=3, 5 Hz), 3.15 (1H, dd, J=3, 18 Hz), 3.59 (2H, t, J=6 Hz), 3.80–4.38 (4H, m), 4.46–4.70 (2H, m), 5.10–5.43 (2H, m), 5.70–6.20 (2H, m), 6.86 (1H, m).

PREPARATION 5-6)

To a solution of (3S,4R)-4-[2-(1-allyloxycarbonyl-1,2,3,6-tetrahydropyridin-4-yl)-2-oxoethyl]-3-[(1R)-1-t-butyldimethylsilyloxyethyl]-2-oxoazetidine (1.85 g) in toluene (40 ml) was added allyl glyoxylate monohydrate (0.78 g). The resultant mixture was heated to reflux with azeotropic removal of water for 4 hours. Evaporation of the solvent gave a residue, which was dissolved in xylene and evaporated in vacuo. The residue was dissolved in dichloromethane (20 ml). To this solution were added successively 2,6-lutidine (0.58 ml) and thionyl chloride 0.42 ml) at −20° C. After stirring at −20° C. for 15 minutes, the reaction mixture was poured into a mixture of ethyl acetate (100 ml) and water (100 ml) at 5° C. After adjusting pH to around 6.5 with aqueous sodium hydrogen carbonate, the organic layer was separated, washed with brine, dried over magnesium sulfate, and evaporated. The residue was dissolved in degassed N,N-dimethylformamide (20 ml), and to the solution were added 2,6-lutidine (0.58 ml) and triphenylphosphine (1.29 g). After standing for 6 hours at ambient temperature, the reaction mixture was poured into a mixture of ethyl acetate (100 ml) and water (100 ml). The separated organic layer was washed in turn with water, aqueous sodium hydrogen carbonate, and brine, and dried over magnesium sulfate. Evaporation of the solvent gave a residue, which was chromatographed on silica gel (50 g) eluting with a mixture of n-hexane and ethyl acetate (5:1–3:7, V/V) to give allyl 2-[(3S,4R)-4-{2-(1-allyloxycarbonyl-1,2,3,6-tetrahydropyridin-4-yl)-2-oxoethyl}-3-{(1R)-1-t-butyldimethylsilyloxyethyl}-2-oxoazetidin-1-yl]-2-triphenylphosphoranylideneacetate (2.10 g).

IR (CH$_2$CH$_2$): 1740, 1700 cm$^{-1}$.

NMR (CDCl$_3$, δ): −0.10–0.23 (6H, m), 0.70–1.00 (9H, m), 1.00–1.39 (3H, m), 2.20–3.25 (5H, m), 3.25–3.75 (2H, m), 4.00–4.85 (8H, m), 4.85–5.60 (4H, m), 5.60–6.30 (2H, m), 6.70–7.00 (1H, m), 7.30–7.93 (15H, m).

PREPARATION 6-1)

A methylene chloride solution (375 ml) of dimethyl sulfoxide (21.8 ml) was cooled to −70° C. and a methylene chloride solution (125 ml) of oxalyl chloride (13.4 ml) was added thereto below −50° C. After completion of the addition, the mixture was stirred for 30 minutes, at the end of which time a solution of 1-allyloxycarbonyl-3-hydroxypyrrolidine (25 g) in methylene chloride (125 ml) was added below −50° C. The mixture was stirred at the same temperature for 1 hour and, then, triethylamine (101 ml) was added at a temperature below −50° C. The mixture was further stirred at that temperature for 1 hour. Thereafter, the temperature was allowed to rise gradually to room temperature and the reaction mixture was diluted with water and allowed to stand. The aqueous layer was then separated and extracted with 2 portions of methylene chloride. The organic layers were combined, washed with 1N hydrochloric acid, saturated aqueous sodium hydrogen carbonate solution, water and aqueous sodium chloride solution successively, and dried over anhydrous magnesium sulfate. Finally the solvent was distilled off under reduced pressure to give 1-allyloxycarbonyl-3-oxopyrrolidine (24.5 g).

IR (Neat): 1760, 1700, 1650 cm$^{-1}$.

NMR (CDCl$_3$, δ): 2.60 (2H, t, J=8 Hz), 3.80 (2H, s), 3.83 (2H, t, J=8 Hz), 4.61 (2H, dt, J=5 and 1 Hz), 5.10–5.45 (2H, m), 5.70–6.15 (1H, m).

PREPARATION 6-2)

To a solution of trimethylsilylacetylene (16.3 ml) in tetrahydrofuran (100 ml) were added successively a solution of n-butyllithium in n-hexane (1.50M, 70 ml) and a solution of 1-allyloxycarbonyl-3-oxopyrrolidine (15 g) in tetrahydrofuran (15 ml) at −50° C. After stirring at −50° C. for 1 hour, to the mixture was added a mixture of aqueous ammonium chloride and ethyl acetate at 0° C. The organic layer was separated and the aqueous layer was extracted with ethyl acetate twice. The organic layers were combined washed with 1N hydrochloric acid, water and brine successively and dried over magnesium sulfate. Evaporation of the solvent in vacuo gave 1-allyloxycarbonyl-3-hydroxy-3-trimethylsilylethynylpyrrolidine (19.5 g).

IR (Neat): 1700, 1640, 1610 cm$^{-1}$.

NMR (CDCl$_3$, δ): 0.18 (9H, s), 2.16 (2H, t, J=7 Hz), 2.52 (1H, br s), 3.57 (2H, t, J=7 Hz), 3.61 (2H, s), 4.57 (2H, dt, J=5 and 1 Hz), 5.05–5.40 (2H, m), 5.70–6.15 (1H, m).

PREPARATION 6-3)

To a solution of 1-allyloxycarbonyl-3-hydroxy-3-trimethylsilylethynylpyrrolidine (18.0 g) in pyridine (180 ml) was added dropwise thionyl chloride (29 ml) below 20° C. The resultant mixture was stirred for 1 hour and slowly poured into cooled water. The solution was extracted three times with n-hexane The extracts were combined, washed with 1N hydrochloric acid (4 times), saturated aqueous sodium hydrogen carbonate, water and brine successively, dried over magnesium sulfate and evaporated. The residue was chromatographed on silica gel to give 1-allyloxycarbonyl-3-trimethylsilylethynyl-3-pyrroline (7.25 g).

IR (Neat): 2170, 1755, 1700, 1645 cm$^{-1}$.

NMR (CDCl$_3$, δ): 0.22 (9H, s), 3.50–4.40 (2H, m), 4.23 (2H, s), 4.62 (2H, d, J=6 Hz), 5.10–5.50 (2H, m), 5.70–6.30 (2H, m).

PREPARATION 6-4)

A solution of 1-allyloxycarbonyl-3-trimethylsilylethynyl-3-pyrroline (7.60 g), mercuric sulfate (0.9 g) and sulfuric acid (5 drops) in a mixture of tetrahydrofuran (76 ml) and water (23 ml) was stirred at room temperature overnight. After confirming the disappearance of the starting material, to the mixture were added saturated aqueous sodium hydrogen carbonate and ethyl acetate. The aqueous layer was extracted with ethyl acetate twice, and the combined organic layer was washed with 1N hydrochloric acid, saturated aqueous sodium hydrogen carbonate, water and brine successively, dried over magnesium sulfate. Evaporation of the solvent gave 1-allyloxycarbonyl-3-acetyl-3-pyrroline (2.3 g).

IR (Neat): 1760, 1700, 1630 cm$^{-1}$.

NMR (CDCl$_3$, δ): 2.36 (3H, s), 4.40 (4H, m), 4.60 (2H, dt, J=6 and 1 Hz), 5.08–5.45 (2H, m), 5.70–6.15 (1H, m), 6.62 (1H, m).

PREPARATION 6-5)

(3S,4R)-4-[2-(1-Allyloxycarbonyl-3-pyrrolin-3-yl)-2-oxoethyl]-3-[(1R)-1-t-butyldimethylsilyloxyethyl]-2-oxoazetidine was obtained in 58.2% yield in substantially the same manner as that of Preparation 5-5).

IR (CHCl$_3$): 3420, 1755, 1700, 1630 cm$^{-1}$.

NMR (CDCl$_3$, δ): 0.08 (6H, s), 0.87 (9H, s), 1.20 (3H, d, J=7 Hz), 2.6–3.30 (3H, m), 3.80–4.50 (6H, m), 4.59 (2H, d, J=6 Hz), 5.03–5.40 (2H, m), 5.60–6.15 (2H, m), 6.62 (1H, m).

PREPARATION 6-6)

Allyl 2-[(3S,4R)-4-{2-(1-allyloxycarbonyl-3-pyrrolin-3yl)-2-oxoethyl}-3-{(1R)-1-t-butyldimethylsilyloxyethyl}-2-oxoazetidin-1-yl]-2-triphenylphosphoranylideneacetate was obtained in 64.5% yield in substantially the same manner as that of Preparation 5-6). [This compound was immediately used as the starting material of Example 1-2).]

PREPARATION 7-1)

3-Acetylpyridine (10 g), ethylene glycol (50 ml) and p-toluenesulfonic acid (0.5 g) were dissolved in toluene and the solution was refluxed at 150° C. for 1 day with the by-product water being constantly removed. After cooling, saturated aqueous sodium hydrogen carbonate and toluene were added and the mixture was stirred and allowed to stand. The aqueous layer was separated and extracted with 2 portions of toluene. The toluene layers were combined, washed sequentially with saturated aqueous sodium hydrogen carbonate, water and aqueous sodium chloride solution, and dried over anhydrous magnesium sulfate. Finally the solvent was distilled off under reduced pressure to give 2-methyl-2-(pyridin-3-yl)-1,3-dioxolane (13.6 g).

IR (neat): 2990, 2890, 1685 cm$^{-1}$.

NMR (CDCl$_3$, δ): 1.67 (3H, s), 3.60–4.20 (4H, m), 7.05–7.40 (1H, m), 7.60–7.80 (1H, m), 8.45–8.80 (2H, m).

PREPARATION 7-2)

Benzyl bromide (9.8 ml) was added to a solution of 2-methyl-2-(pyridin-3-yl)-1,3-dioxolane (13.6 g) in acetone (140 ml) and the mixture was refluxed. After confirming the disappearance of the starting material, the acetone was distilled off under reduced pressure. The residue was dissolved in ethanol (140 ml) and while the solution was ice-cooled, sodium borohydride (3.12 g) was gradually added. After the mixture was stirred for 1 hour, water and ethyl acetate were added. The mixture was stirred and, then, allowed to stand. The aqueous layer was separated and extracted with 2 portions of ethyl acetate. The organic layers were combined, washed successively with saturated aqueous sodium hydrogen carbonate solution, water and aqueous sodium chloride solution, and dried over anhydrous magnesium sulfate. Finally the solvent was distilled off under reduced pressure to give 2-(1-benzyl-1,2,5,6-tetrahydropyridin-3-yl)-2-methyl-1,3-dioxolane (7.86 g).

IR (neat): 2900, 1740 cm$^{-1}$.

NMR (CDCl$_3$, δ): 1.43 (3H, s), 1.90–2.30 (2H, m), 2.48 (2H, t, J=6 Hz), 2.95 (2H, s), 3.57 (2H, s), 3.70–3.95 (4H, m), 5.83 (1H, m), 7.23 (5H, s).

PREPARATION 7-3)

To a solution of 2-(1-benzyl-1,2,5,6-tetrahydropyridin-3-yl)-2-methyl-1,3-dioxolane (7.8 g) in toluene (70 ml) was added allyl chloroformate (3.9 ml) and the mixture was stirred at 60° C. for 30 minutes. The reaction mixture was then concentrated and the residue was purified by column chromatography to give 2-(1-allyloxycarbonyl-1,2,5,6-tetrahydropyridin-3-yl)-2-methyl-1,3-dioxolane (6.95 g).

IR (neat): 2900, 1700 cm$^{-1}$.

NMR (CDCl$_3$, δ): 1.47 (3H, s), 2.00–2.30 (2H, m), 3.47 (2H, t, J=6 Hz), 3.70–4.00 (6H, m), 4.50–4.65 (2H, m), 5.03–5.35 (2H, m), 5.75 (1H, t, J=6 Hz), 5.83–6.05 (1H, m).

PREPARATION 7-4)

To a solution of 2-(1-allyloxycarbonyl-1,2,5,6-tetrahydropyridin-3-yl)-2-methyl-1,3-dioxolane (6.95 g) in acetone (140 ml) was added p-toluenesulfonic acid dihydrate (523 mg) at room temperature and the mixture was stirred at the same temperature for 1 hour. Then, saturated aqueous sodium hydrogen carbonate solution was added for neutralization of the acid and the reaction mixture was concentrated under reduced pressure. The concentrate was diluted with ethyl acetate and water, followed by stirring, and the aqueous layer was separated and extracted with 2 portions of ethyl acetate. The organic layers were combined, washed successively with saturated aqueous sodium hydrogen carbonate solution, water and aqueous sodium chloride solution, and dried over anhydrous magnesium sulfate. The solvent was then distilled off under reduced pressure and the residue was purified by column chromatography to give 1-allyloxycarbonyl-3-acetyl-1,2,5,6-tetrahydropyridine (4.43 g).

IR (neat): 1700, 1670 cm$^{-1}$.

NMR (CDCl$_3$, δ): 2.30 (3H, s), 2.15–2.50 (2H, m), 3.52 (2H, t, J=6 Hz), 4.15 (2H, m), 4.57 (2H, dt, J=6, 1 Hz), 5.05–5.37 (2H, m), 5.60–6.13 (1H, m), 6.92 (1H, m).

PREPARATION 7-5)

1-Allyloxycarbonyl-3-acetyl-1,2,5,6-tetrahydropyridine (4.4 g), (3R,4R)-4-acetoxy-3-[(1R)-1-tert-butyldimethylsilyloxyethyl]-2-oxoazetidine (6.6 g) and triethylamine (6.9 ml) were dissolved in methylene chloride and the solution (44 ml) was cooled to −50° C. To this cooled solution was gradually added trimethylsilyl trifluoromethanesulfonate (10.6 ml). After completion of the dropwise addition, the mixture was stirred at the same temperature for 15 minutes. The temperature was then allowed to rise gradually to 0° C., at which temperature the reaction mixture was stirred for 1 hour to complete the reaction. This reaction mixture was diluted with ethyl acetate and water and stirred at room temperature for 1 hour. The aqueous layer was separated and extracted with 2 portions of ethyl acetate. The organic layers were combined, washed successively with 1N hydrochloric acid, saturated aqueous sodium hydrogen carbonate, water and aqueous sodium chloride solution, and dried over anhydrous magnesium sulfate. The solvent was then distilled off under reduced pressure and the residue was purified by column chromatography to give (3S,4R)-4-[2-(1-allyloxycarbonyl-1,2,5,6-tetrahydropyridin-3-yl)-2-oxoethyl]-3-[(1R-1-tert-butyldimethylsilyloxyethyl]-2-oxoazetidine (8.73 g).

IR (CHCl$_3$): 3440, 1760, 1695, 1650 cm$^{-1}$.

NMR (CDCl$_3$, δ): 0.08 (6H, s), 0.88 (9H, s), 1.22 (3H, d, J=6 Hz), 2.25–2.88 (2H, m), 2.70–3.10 (3H, m), 3.53 (2H, t, J=6 Hz), 3.83–4.30 (4H, m), 4.56 (2H, dt, J=6, 1 Hz), 5.05–5.40 (2H, m), 5.65–6.07 (1H, m), 6.10 (1H, br. s), 6.93 (1H, m).

PREPARATION 8-1)

A methylene chloride solution (200 ml) of dimethyl sulfoxide (15.1 ml) was cooled to −70° C. and oxalyl chloride (19.3 ml) was added thereto below −50° C. The mixture was stirred for 15 minutes, at the end of which time a solution of (2S,4R)-1-allyloxycarbonyl-4-hydroxy-2-methoxycarbonylpyrrolidine (16.3 g) in methylene chloride was added below −50° C. The mixture was stirred at the same temperature for 1 hour and, then, triethylamine (50 ml) was added at a temperature below −50° C. The mixture was further stirred at that temperature for 30 minutes. Thereafter, the temperature was allowed to rise gradually to room temperature and the reaction mixture was diluted with water and allowed to stand. The aqueous layer was then separated and extracted with 2 portions of methylene chloride. The organic layers were combined, washed with 1N hydrochloric acid twice and, then, with saturated aqueous sodium hydrogen carbonate solution, water and aqueous sodium chloride solution successively, and dried over anhydrous magnesium sulfate. Finally the solvent was distilled off under reduced pressure to give (2S)-1-allyloxycarbonyl-2-methoxycarbonyl-4-oxopyrrolidine (15.5 g).

IR (neat): 1760, 1705 cm$^{-1}$.

NMR (CDCl$_3$, δ): 2.55 (1H, dd, J=18, 4 Hz), 2.97 (1H, dd, J=18, 10 Hz), 3.74 (3H, s), 3.92 (2H, s), 4.60 (2H, d, J=5 Hz), 4.80 (1H, dd, J=10, 4 Hz), 5.05–5.40 (2H, m), 5.60–6.10 (1H, m).

PREPARATION 8-2)

To a solution of trimethylsilylacetylene (5 g) in tetrahydrofuran (60 ml) was added n-butyllithium (32 ml) slowly and dropwise at −50° C. After completion of the dropwise addition, the mixture was stirred at −50° C. for 30 minutes, at the end of which time a tetrahydrofuran solution (10 ml) of (2S)-1-allyloxycarbonyl-2-methoxycarbonyl-4-oxopyrrolidine (10 g) was added below −50° C. The mixture was stirred for 1 hour and, then, diluted with saturated aqueous ammonium chloride solution and ethyl acetate. After standing, the aqueous layer was separated and extracted with ethyl acetate twice and the organic layers were combined, washed successively with 1N hydrochloric acid, saturated aqueous sodium hydrogen carbonate solution, water and aqueous sodium chloride solution and dried over anhydrous magnesium sulfate. Finally the solvent was distilled off under reduced pressure to give 1-allyloxycarbonyl-4-hydroxy-2-methoxycarbonyl-4-trimethylsilylethynylpyrrolidine (8.26 g).

IR (neat): 3400, 2180, 1760, 1700 cm$^{-1}$.

NMR (CDCl$_3$, δ): 0.12 (9H, s), 2.20–2.60 (2H, m), 3.70 (5H, m), 4.30–4.60 (3H, m), 5.00–5.35 (2H, m), 5.55–6.05 (1H, m).

PREPARATION 8-3)

To a solution of 1-allyloxycarbonyl-4-hydroxy-2-methoxycarbonyl-4-trimethylsilylethynylpyrrolidine (7.0 g) in toluene (70 ml) was slowly added phosphorus tribromide (2.25 ml) at room temperature and the mixture was stirred at room temperature for one day. The reaction mixture was then poured into iced water-ethyl acetate. The aqueous layer was then separated and extracted with ethyl acetate twice. The organic layers were combined, washed with saturated aqueous sodium hydrogen carbonate solution twice and further with water and aqueous sodium chloride solution successively, and dried over anhydrous magnesium sulfate. Finally the solvent was distilled off under reduced pressure to give 1-allyloxycarbonyl-2-methoxycarbonyl-4-trimethylsilylethynyl-3-pyrroline (3.0 g).

IR (neat): 2170, 1750, 1720 cm$^{-1}$.

NMR (CDCl$_3$, δ): 0.20 (9H, s), 3.72 (3H, s), 4.20–4.35 (2H, m), 4.35–4.70 (3H, m), 5.00–5.40 (2H, m), 5.60–6.07 (2H, m).

PREPARATION 8-4)

To a solution of 1-allyloxycarbonyl-2-methoxycarbonyl-4-trimethylsilylethynyl-3-pyrroline (2.9 g) in tetrahydrofuran (9 ml) and ethanol (36 ml), previously cooled to 5° C., was slowly added sodium borohydride (713 mg) while the internal temperature was maintained below 10° C. The mixture was stirred at 5° C. for 30 minutes and, then, at room temperature for one hour. After decomposition of the sodium borohydride with addition of a small amount of acetic acid, the reaction mixture was diluted with ethyl acetate and water. The aqueous layer was extracted with ethyl acetate twice. The organic layers were combined, washed successively with 1N hydrochloric acid, saturated aqueous sodium hydrogen carbonate solution, water and aqueous sodium chloride solution, and dried over anhydrous magnesium sulfate. The solvent was then distilled off under reduced pressure. To the residue were added tetrahydrofuran (26 ml), water (5 ml), mercuric sulfate (280 mg) and sulfuric acid (2 drops) and the mixture was stirred at room temperature for 1 day. After completion of the reaction, saturated aqueous sodium hydrogen carbonate solution and ethyl acetate were added. The aqueous layer was then separated and extracted with ethyl acetate twice. The organic layers were combined, washed successively with 1N hydrochloric acid, saturated aqueous sodium hydrogen carbonate solution, water and aqueous sodium chloride solution, and dried over anhydrous magnesium sulfate. Finally the solvent was distilled off under reduced pressure to give 1-allyloxycarbonyl-4-acetyl-2-hydroxymethyl-3-pyrroline (2.50 g).

NMR (CDCl$_3$, δ): 2.35 (3H, s), 3.85 (3H, m), 4.37 (2H, m), 4.60 (2H, dt, J=6, 1 Hz), 4.88 (1H, m), 5.10–5.45 (2H, m), 5.70–6.15 (1H, m), 6.52 (1H, m).

PREPARATION 8-5)

To a methylene chloride solution (50 ml) of 1-allyloxycarbonyl-4-acetyl-2-hydroxymethyl-3-pyrroline (2.5 g) and imidazole (1.51 g) was added tert-butyldimethylsilyl chloride (2.5 g) under ice-cooling. The mixture was then stirred at room temperature for one day, followed by addition of water and ethyl acetate. The aqueous layer was separated and extracted with ethyl acetate twice. The organic layers were combined, washed with 1N hydrochloric acid, saturated aqueous sodium hydrogen carbonate solution, water and aqueous sodium chloride solution, and dried over anhydrous magnesium sulfate. Finally the solvent was distilled off under reduced pressure to give 1-allyloxycarbonyl-4-acetyl-2-tert-butyldimethylsilyloxymethyl-3-pyrroline (1.45 g).

IR (neat): 1700, 1670 cm$^{-1}$.

NMR (CDCl$_3$, δ): 0.04 (6H, s), 0.87 (9H, s), 2.15 (3H, s), 3.70–4.00 (2H, m), 4.15–4.40 (2H, m), 4.57 (2H, d, J=5 Hz), 4.75 (1H, m), 5.00–5.40 (2H, m), 5.60–6.10 (1H, m), 6.60 (1H, m).

PREPARATION 8-6)

In substantially the same manner as described in Preparation 5, (3S,4R)-4-[2-(1-allyloxycarbonyl-2-tert-butyldimethylsilyloxymethyl-3-pyrrolin-4-yl)-2-oxoethyl]-3-[(1R)-1-tert-butyldimethylsilyloxyethyl]-2-oxoazetidine was obtained.

IR (CHCl$_3$): 3410, 1750, 1695, 1670, 1625 cm$^{-1}$.

NMR (CDCl$_3$, δ): 0.08 (3H, s), 0.12 (3H, s), 0.90 (9H, s), 1.25 (3H, d, J=7 Hz), 2.70–3.30 (3H, m), 3.70–4.45 (6H, m), 4.61 (2H, d, J=5 Hz), 4.80 (1H, m), 5.10–5.45 (2H, m), 5.70–6.20 (1H, m), 6.10 (1H, m), 6.65 (1H, m).

PREPARATION 9-1)

To a solution of oxalyl chloride (5.8 ml) in dichloromethane (100 ml) were added dropwise dimethyl sulfoxide (9.44 ml), a solution of 1-benzyl-4-(1-hydroxyethyl)-1,2,3,6-tetrahydropyridine (13.7 g) in dichloromethane (30 ml) and triethylamine (44.2 ml ) under nitrogen atmosphere at −70° C. Then, the reaction mixture was allowed to warm at ambient temperature and precipitate was filtered off. The filtrate was concentrated in vacuo and the residue was dissolved in a mixture of ethyl acetate (200 ml) and water (100 ml). The organic layer was separated, washed with brine (100 ml), dried over magnesium sulfate. Evaporation of the solvent gave a residue, which was chromatographed on silica gel (350 ml) eluting with a mixture of hexane and ethyl acetate (1:1, V/V) to give 4-acetyl-1-benzyl-1,2,3,6-tetrahydropyridine (9.63 g).

IR (Nujol): 1740, 1670 cm$^{-1}$.

NMR (CDCl$_3$, δ): 2.27 (3H, s), 2.26–2.71 (4H, m), 3.13–3.23 (2H, m), 3.61 (2H, s), 6.67–6.82 (1H, m), 7.29 (5H, s).

PREPARATION 9-2)

To a solution of 4-acetyl-1-benzyl-1,2,3,6-tetrahydropyridine (9.63 g) and benzyloxycarbonyl chloride (9.06 ml) in toluene was heated at 85° C. for 8 hours. After the solvent was removed in vacuo, the residual solution was dissolved in ethyl acetate (100 ml), washed with saturated aqueous sodium hydrogen carbonate (100 ml×3) and brine (100 ml) successively. The organic layer was separated, dried over magnesium sulfate and concentrated in vacuo to give an oil, which was chromatographed on silica gel (500 ml) eluting with a mixture of hexane and ethyl acetate (1:1, V/V) to give 4-acetyl-1-benzyloxycarbonyl-1,2,3,6-tetrahydropyridine (10.2 g).

IR (Nujol): 1760, 1680–1715 cm$^{-1}$.

NMR (CDCl$_3$, δ): 2.31 (3H, s), 2.30–2.45 (2H, m), 3.58 (2H, t, J=5.8 Hz), 4.18–4.23 (2H, m), 5.16 (2H, s), 6.7–6.83 (1H, m), 7.30 (5H, s).

PREPARATION 9-3)

To a solution of (3R,4R)-4-acetoxy-3-[(1R)-1-t-butyldimethylsilyloxyethyl]-2-oxoazetidine (3.96 g) and triethylamine (2.03 ml) in dichloromethane (60 ml) was added dropwise trimethylsilyl trifluoromethanesulfonate (3.5 ml) at −70° C. under nitrogen atmosphere. To this solution was added dropwise at −70° C. a reaction mixture, which had been prepared by stirring a solution of 4-acetyl-1-benzyloxycarbonyl-1,2,3,6-tetrahydropyridine (3.268 g), triethylamine (1.94 ml) and trimethylsilyl trifluoromethanesulfonate (2.6 ml) in dichloromethane at −70° C. under nitrogen atmosphere. After the mixture was warmed to ambient temperature, the mixture was stirred for 2 hours. The reaction mixture was poured into a mixture of ethyl acetate (200 ml) and water (100 ml), and the solution was stirred for 30 minutes. The organic layer was separated, washed with brine (100 ml), dried over magnesium sulfate and concentrated to give an oil, which was chromatographed on silica gel (300 ml) eluting with a mixture of hexane and ethyl acetate (2:1–1:5, V/V) to give (3S,4R)-4-[2-(1-benzyloxycarbonyl-1,2,3,6-tetrahydropyridin-4-yl)-2-oxoethyl]-3-[(1R)-1-t-butyldimethylsilyloxyethyl]-2-oxoazetidine (4.65 g).

IR (Nujol): 1740–1760, 1670–1710 cm$^{-1}$.

NMR (CDCl$_3$, δ): 0.07 (6H, s), 0.87 (9H, s), 1.22 (3H, d, J=6 Hz), 2.27–2.38 (2H, m), 2.70–2.92 (2H, m), 3.00–3.21 (1H, dd, J=17, 3 Hz), 3.60 (2H, m), 3.92–4.23 (4H, m), 5.16 (2H, s), 6.18 (1H, s), 6.66–6.77 (1H, m), 7.32 (5H, s).

PREPARATION 9-4)

To a solution of (3S,4R)-4-[2-(1-benzyloxycarbonyl-1,2,3,6-tetrahydropyridin-4-yl)-2-oxoethyl]-3-[(1R)-1-t-butyldimethylsilyloxyethyl]-2-oxoazetidine (4.65 g) in acetonitrile (25 ml) was added dropwise boron trifluoride ether complex (2.6 ml) at 0° C., and the mixture was stirred for 1 hour. Sodium hydrogen carbonate (5 g) was added to the reaction mixture, followed by stirring for 30 minutes, and then precipitate was filtered off. Filtrate was dissolved in ethyl acetate (100 ml), washed in turn with water (50 ml) and brine (50 ml), dried over magnesium sulfate. Evaporation of the solvent in vacuo gave (3S,4R)-4-[2-(1-benzyloxycarbonyl-1,2,3,6-tetrahydropyridin-4-yl)-2-oxoethyl]-3-[(1R)-1-hydroxyethyl]-2-oxoazetidine (3.6 g).

IR (Nujol): 3200–3400, 1670–1750 cm$^{-1}$.

NMR (CDCl$_3$, δ): 1.32 (3H, d, J=7 Hz), 2.24–2.40 (2H, m), 2.74–3.13 (4H, m), 3.49–3.64 (2H, m), 3.83–4.27 (4H, m), 5.15 (2H, s), 6.40–6.50 (1H, br s), 6.67–6.86 (1H, m), 7.33 (5H, s).

PREPARATION 9-5)

To a solution of (3S,4R)-4-[2-(1-benzyloxycarbonyl-1,2,3,6-tetrahydropyridine-4-yl)-2-oxoethyl]-3-[(1R)-1-hydroxyethyl]-2-oxoazetidine (3.59 g) and pyridine (3.9 ml in dichloromethane (3.5 ml) was added dropwise trimethylsilyl chloride (1.42 ml) at −70° C. under nitrogen atmosphere and the mixture was stirred for 1 hour. To this solution was added dropwise at −70° C. a reaction mixture of oxalyl chloride (1.26 ml) and 4-nitrobenzyl alcohol (2.3 g) in dichloromethane (10 ml) at 0° C., which solution was stirred for additional 1 hour. The reaction mixture was poured into a mixture of ethyl acetate (70 ml) and water (40 ml). The organic layer was separated, washed with water (50 ml) containing acetic acid (550 μl), and brine (50 ml) successively, and then dried over magnesium sulfate. Evaporation of the solvent gave a residue, which was chromatographed on silica gel (250 ml) eluting with a mixture of hexane and ethyl acetate (1:1, V/V) to give 4-nitrobenzyl 2-[(3S,4R)-4-{2-(1-benzyloxycarbonyl-1,2,3,6-tetrahydropyridin-4-yl)-2-oxoethyl}-3-{(1R)-1-trimethylsilyloxyethyl}-2-oxoazetidin-1-yl]-2-oxoacetate (4.73 g).

IR (Nujol): 1800, 1750, 1660–1710 cm$^{-1}$.

NMR (CDCl$_3$, δ): 0.04 (9H, s), 1.18 (3H, d, J=7 Hz), 2.29–2.38 (2H, m), 3.00–3.20 (2H, m), 3.51–3.62 (2H, m), 4.06–4.31 (3H, m), 4.56–4.64 (1H, m), 5.15 (2H, s), 5.40 (2H, s), 6.73–6.83 (1H, m), 7.35 (5H, s), 7.55–7.60 (2H, m), 8.21–8.28 (2H, m).

PREPARATION 10-1)

To a solution of (R)-3-hydroxypyrrolidine hydrochloride (20 g) in a mixture of 1,4-dioxane (200 ml) and water (200 ml) were added triethylamine (49.6 ml) and di-t-butyl dicarbonate (38.9 g) at 0° C. After stirring for 12 hours at ambient temperature, the mixture was evaporated in vacuo. The residue was extracted with ethyl acetate, and the organic solution was washed with brine and dried over magnesium sulfate. The solvent was evaporated to give (R)-1-t-butoxycarbonyl-3-hydroxypyrrolidine (32 g).

IR (Neat): 3400, 1660–1680 cm$^{-1}$.

NMR (CDCl$_3$, δ): 1.46 (9H, s), 1.8–2.0 (2H, m), 2.3–2.4 (1H, m), 3.2–3.5 (4H, m).

PREPARATION 10-2)

To a solution of (R)-1-t-butoxycarbonyl-3-hydroxypyrrolidine (32 g) in dichloromethane (300 ml) were added triethylamine (28.6 ml) and then methanesulfonyl chloride (14.6 ml) under nitrogen at −10° C. After stirring at 0° C. for 30 minutes, the solution was washed in turn with water, 1N-hydrochloric acid solution, saturated sodium bicarbonate, and brine. The dried solution was evaporated to give (R)-1-t-butoxycarbonyl-3-methanesulfonyloxypyrrolidine (45 g).

IR (CH$_2$Cl$_2$): 1690 cm$^{-1}$.

NMR (CDCl$_3$, δ): 1.47 (9H, s), 2.9–2.42 (2H, m), 3.00 (3H, s), 3.35–3.75 (5H, m).

PREPARATION 10-3)

To a solution of (R)-1-t-butoxycarbonyl-3-methanesulfonyloxypyrrolidine (20 g) in dimethyl sulfoxide (200 ml) was added sodium benzoate (22 g) under nitrogen. After stirring at 100° C. for 1 hour, the solution was taken up into a mixture of ethyl acetate and water. The organic layer was separated, and washed with water and brine successively. The dried solvent was evaporated to give (S)-3-benzoyloxy-1-t-butoxycarbonylpyrrolidine (22 g).

IR (CH$_2$Cl$_2$): 1725, 1690 cm$^{-1}$.

NMR (CDCl$_3$, δ): 1.48 (9H, s), 2.18–2.31 (2H, m), 3.52–3.67 (4H, m), 7.40–7.61 (3H, m), 8.00–8.14 (2H, m).

PREPARATION 10-4)

To a solution of (S)-3-benzoyloxy-1-t-butoxycarbonylpyrrolidine (21 g) in methanol (210 ml) was added 28% sodium methoxide in methanol solution (18 ml) under nitrogen at −10° C. After stirring at 0° C. for 2 hours, acetic acid (4.95 ml) was added thereto and the mixture was evaporated. The residue was extracted with ethyl acetate and the extract was washed with water and brine successively. The dried organic solvent was evaporated to give (S)-1-t-butoxycarbonyl-3-hydroxypyrrolidine (19.0 g).

IR (Neat): 3400, 1690 cm$^{-1}$.

NMR (CDCl$_3$, δ): 1.46 (9H, s), 1.8–2.0 (2H, m), 2.3–2.4 (1H, m), 3.2–3.5 (4H, m).

PREPARATION 10-5)

(S)-1-t-Butoxycarbonyl-3-methanesulfonyloxypyrrolidine was obtained in 88.4% yield in substantially the same manner as that of Preparation 10-2).

IR (Neat): 1690 cm$^{-1}$.

NMR (CDCl$_3$, δ): 1.47 (9H, s), 2.01–2.42 (2H, m), 3.04 (3H, s), 3.55–3.75 (5H, m).

PREPARATION 10-6)

(R)-1-t-Butoxycarbonyl-3-cyanopyrrolidine was obtained in 48.0% yield in substantially the same manner as that of Preparation 11-1).

IR (Neat): 2225, 1690 cm$^{-1}$.

NMR (CDCl$_3$, δ): 1.46 (9H, s), 1.88–2.43 (2H, m), 2.98–3.29 (1H, m), 3.27–3.80 (4H, m).

PREPARATION 10-7)

(R)-1-Allyloxycarbonyl-3-carboxypyrrolidine was obtained quantitatively in substantially the same manner as that of Preparation 11-2).

IR (CH$_2$Cl$_2$): 1690–1710 cm$^{-1}$.

NMR (CDCl$_3$, δ): 2.00–2.32 (2H, m), 2.88–3.30 (1H, m), 3.32–3.81 (4H, m), 4.53 (2H, d, J=6 Hz), 5.02–5.49 (2H, m), 5.62–6.19 (1H, m).

PREPARATION 10-8)

(R)-3-Acetyl-1-allyloxycarbonylpyrrolidine was obtained in 65.7% yield in substantially the same manner as that of Preparation 2-1).

IR (Neat): 1690–1710 cm$^{-1}$.

NMR (CDCl$_3$, δ): 2.20 (3H, s), 1.89–2.30 (2H, m), 2.85–3.70 (5H, m), 4.45–4.66 (2H, m), 5.02–5.49 (2H, m), 5.61–6.17 (1H, m).

PREPARATION 10-9)

(3S,4R)-4-[2-{(3R)-1-Allyloxycarbonylpyrrolidin-3-yl}-2-oxoethyl]-3-[(1R)-1-t-butyldimethylsilyloxyethyl]-2-oxoazetidine was obtained in 48.0% yield in substantially the same manner as that of Preparation 3.

IR (CH$_2$Cl$_2$): 3270, 1760, 1710 cm$^{-1}$.

NMR (CDCl$_3$, δ): 0.07 (6H, s), 0.87 (9H, s), 1.20–1.29 (3H, m), 2.04–2.21 (2H, m), 2.67–3.30 (4H, m), 3.41–3.80 (4H, m), 3.90–4.23 (2H, m), 4.57–4.60 (2H, m), 5.18–5.34 (2H, m), 5.87–6.03 (1H, m), 6.17 (1H, br s).

PREPARATION 11-1)

To a solution of (R)-1-t-butoxycarbonyl-3-methanesulfonyloxypyrrolidine (20 g) in dimethyl sulfoxide (200 ml) was added sodium cyanide (11 g) at ambient temperature under nitrogen. After stirring at 100° C. under nitrogen for 1 hour, the solution was taken up into a mixture of ethyl acetate and water. The organic layer was separated, and washed with water and brine successively. The dried solvent was evaporated, and the residue was chromatographed on silica gel eluting with a mixture of n-hexane and ethyl acetate (2:1, V/V) to give (S)-1-t-butoxycarbonyl-3-cyanopyrrolidine (9.0 g).

IR (Neat): 2255, 1690 cm$^{-1}$.

NMR (CDCl$_3$, δ): 1.46 (9H, s), 2.00–2.40 (2H, m), 2.98–3.31 (1H, m), 3.31–3.80 (4H, m).

PREPARATION 11-2)

After a solution of (S)-1-t-butoxycarbonyl-3-cyanopyrrolidine (8.0 g) in a mixture of acetic acid (60 ml) and conc. hydrochloric acid (60 ml) was stirred for 3 hours at 100° C., the solvent was evaporated in vacuo. The residue was dissolved in a mixture of water (80 ml) and tetrahydrofuran (80 ml). To the solution was dropwise added allyl chloroformate (4.7 ml) at 0° C. while adjusting pH to 8.5 with 30% aqueous sodium hydroxide solution. After stirring for 10 minutes, the solution was adjusted to pH 2.0 with 1N-hydrochloric acid. The mixture was extracted with ethyl acetate and then the organic layer was washed with brine and dried over magnesium sulfate. The solvent was evaporated to give (S)-1-allyloxycarbonyl-3-carboxypyrrolidine (9.8 g).

IR (CH$_2$Cl$_2$): 1690–1710 cm$^{-1}$.

NMR (CDCl$_3$, δ): 2.05–2.24 (2H, m), 2.98–3.05 (1H, m), 3.38–3.77 (4H, m), 4.56–4.61 (2H, m), 5.17–5.35 (2H, m), 5.84–6.03 (1H, m), 8.58 (1H, br s).

PREPARATION 11-3)

(S)-3-Acetyl-1-allyloxycarbonylpyrrolidine was obtained in 60.8% yield in substantially the same manner as that of Preparation 2-1).

IR (Neat): 1690–1720 cm$^{-1}$.

NMR (CDCl$_3$, δ): 2.21 (3H, s), 1.96–2.25 (2H, m), 3.11–3.22 (1H, m), 3.40–3.71 (4H, m), 4.54–4.60 (2H, m), 5.17–5.34 (2H, m), 5.84–6.03 (1H, m).

PREPARATION 11-4)

(3S,4R)-4-[2-{(S)-1-Allyloxycarbonylpyrrolidin-3-yl}-2-oxoethyl]-3-[(1R)-1-t-butyldimethylsilyloxyethyl]-2-oxoazetidine was obtained in 61.0% yield in substantially the same manner as that of Preparation 3.

IR (CH$_2$Cl$_2$): 3300, 1765, 1710 cm$^{-1}$.

NMR (CDCl$_3$, δ): 0.07 (6H, s), 0.87 (9H, s), 1.19–1.29 (3H, m), 2.04–2.22 (2H, m), 2.66–3.17 (4H, m), 3.36–3.60 (4H, m), 3.93–4.24 (2H, m), 4.57–4.61 (2H, m), 5.18–5.35 (2H, m), 5.84–6.04 (1H, m), 6.08 (1H, br s).

PREPARATION 12-1)

To a solution of 1-(diphenylmethyl)-3-methoxycarbonylazetidine (28 g) in methanol (270 ml) and tetrahydrofuran (130 ml) was added 1N sodium hydroxide (115 ml) and the solution was stirred at room temperature for 1.5 hours. The solution was then concentrated to remove organic solvents under reduced pressure. The resultant aqueous solution was adjusted to pH 2.95 with 10% hydrochloric acid, and resulting precipitates were collected by filtration, washed with water and dried to give 1-(diphenylmethyl)-3-carboxyazetidine (24.7 g).

mp: 138°–140° C.

NMR (DMSO-d$_6$, δ): 3.09–3.45 (5H, m), 4.42 (1H, s), 7.13–7.43 (10H, m).

PREPARATION 12-2)

To a solution of 1-(diphenylmethyl)-3-carboxyazetidine (21.6 g) in methanol (300 ml) and tetrahydrofuran (200 ml) was added 10% palladium on carbon (17 g) and the mixture was hydrogenated for 4 hours under the pressure of 5 kg/cm$^2$ of hydrogen. The catalyst was removed by filtration and the filtrate was evaporated. To the residue were added water (180 ml) and ethyl acetate (120 ml) and the solution was stirred for 5 minutes. The separated aqueous layer was mixed with tetrahydrofuran (100 ml) and cooled to 0°–5° C. A solution of allyl chloroformate (14.2 ml) in tetrahydrofuran (30 ml) was dropwise added thereto while adjusting the pH to 9–10. After 2 hours, ethyl acetate (100 ml) was added and the separated organic layer was washed with water (20 ml), dried and evaporated to give 1-allyloxycarbonyl-3-carboxyazetidine (10.1 g).

NMR (CDCl$_3$, δ): 3.46 (1H, m), 4.18 (4H, d, J=6 Hz), 4.55 (2H, m), 5.08–5.38 (2H, m), 5.65–6.10 (1H, m), 7.29 (1H, s).

PREPARATION 12-3)

3-Acetyl-1-allyloxycarbonylazetidine was obtained in 70.8% yield in substantially the same manner as that of Preparation 2-1).

IR (CH$_2$Cl$_2$): 1710 cm$^{-1}$.

NMR (CDCl$_3$, δ): 2.19 (3H, s), 3.40–3.55 (1H, m), 4.13 (4H, d, J=8 Hz), 4.53–4.57 (2H, m), 5.17–5.35 (2H, m), 5.81–5.98 (1H, m).

PREPARATION 12-4)

(3S,4R)-4-[2-(1-Allyloxycarbonylazetidin-3-yl)-2-oxoethyl]-3-[(1R)-1-t-butyldimethylsilyloxyethyl]-2-oxoazetidine was obtained in 47.8% yield in substantially the same manner as that of Preparation 3.

IR (Neat): 1760, 1710 cm$^{-1}$.

NMR (CDCl$_3$, δ): 0.04 (6H, s), 0.94 (9H, s), 1.20 (3H, d, J=6 Hz), 2.53–2.89 (3H, m), 3.39–3.50 (1H, m), 3.87–4.17 (6H, m), 4.46–4.51 (2H, m), 5.12–5.28 (2H, m), 5.74–5.91 (1H, m), 6.17 (1H, br s).

PREPARATION 13-1)

To a solution of sodium hydride (60% in oil, 816 mg) and methyl iodide (4.9 ml) in tetrahydrofuran (50 ml), which was heated at 50°–60° C., was added dropwise a solution of (2S,4R)-4-(tert-butyldimethylsilyloxy)-1-(tert-butoxycarbonyl)-2-hydroxymethylpyrrolidine (5.2 g) in tetrahydrofuran (10 ml). After stirring for two hours, the reaction mixture was poured into a mixture of water and ethyl acetate, the organic layer was separated, washed in turn with saturated aqueous sodium sulfite and brine, dried over magnesium sulfate. Evaporation of the solvent gave an oil, which was chromatographed on silica gel (200 ml) eluting with a mixture of hexane and ethyl acetate (4:1, V/V) to give (2S,4R)-4-(tert-butyldimethylsilyloxy)-1-(tert-butoxycarbonyl)-2-methoxymethylpyrrolidine (4.5 g).

IR (Nujol): 1700 cm$^{-1}$.

NMR (CDCl$_3$, δ): 0.08 (6H, s), 0.88 (9H, s), 1.45 (9H, s), 1.83–2.04 (2H, m), 3.32 (3H, s), 3.40–4.45 (6H, m).

PREPARATION 13-2)

A solution of (2S,4R)-4-(tert-butyldimethylsilyloxy)-1-(tert-butoxycarbonyl)-2-methoxymethylpyrrolidine (4.48 g) and tetrabutylammonium fluoride (1 Mol tetrahydrofuran solution, 13 ml) in tetrahydrofuran (45 ml) was stirred at 0° C. for eight hours. The reaction mixture was extracted with ethyl acetate, and the organic layer was separated, washed with brine, dried over magnesium sulfate. Evaporation of the solvent gave an oil, which was chromatographed on silica gel (300 ml) eluting with a mixture of hexane and ethyl acetate (1:2, V/V) to give (2S,4R)-1-(tert-butoxycarbonyl)-4-hydroxy-2-methoxymethylpyrrolidine (2.82 g).

IR (Nujol): 1680–1700, 3350 cm$^{-1}$.

NMR (CDCl$_3$, δ): 1.45 (9H, s), 1.96–2.27 (2H, m), 3.31 (3H, s), 3.40–3.50 (4H, m), 3.93–4.16 (1H, m), 4.34–4.50 (1H, m).

PREPARATION 13-3)

To a solution of (2S,4R)-1-(tert-butoxycarbonyl)-4-hydroxy-2-methoxymethylpyrrolidine (2.8 g) and methanesulfonyl chloride (1.12 ml) in dichloromethane (30 ml) was added dropwise triethylamine (2.38 ml) at 0° C. After 30 minutes, the reaction mixture was washed in turn with 1N-hydrochloric acid, water and brine. The organic layer was dried over magnesium sulfate and evaporated to give an oil, which was chromatographed on silica gel (300 ml) eluting with a mixture of hexane and ethyl acetate (1:1, V/V) to give (2S,4R)-1-(tert-butoxycarbonyl)-4-methanesulfonyloxy-2-methoxymethylpyrrolidine (3.61 g).

IR (Nujol): 1700 cm$^{-1}$.

NMR (CDCl$_3$, δ): 1.47 (9H, s), 2.31 (2H, br s), 3.03 (3H, s), 3.34 (3H, s), 3.40–3.75 (4H, m), 4.04–4.17 (1H, s), 5.23–5.32 (1H, m).

PREPARATION 13-4)

A solution of (2S,4R)-1-(tert-butoxycarbonyl)-4-methanesulfonyloxy-2-methoxymethylpyrrolidine (3.3 g) and sodium cyanide (1.75 g) in dimethyl sulfoxide (35 ml) was heated for three hours and forty minutes at 92° C. The reaction mixture was poured into a mixture of water (100 ml) and ethyl acetate (100 ml). The organic layer was separated, washed with brine, and dried over magnesium sulfate. Evaporation of the solvent gave an oil, which was chromatographed on silica gel (200 ml) eluting with a mixture of hexane and ethyl (1:1, V/V) to give (2S,4S)-1-(tert-butoxycarbonyl)-4-cyano-2-methoxymethylpyrrolidine (2.5 g).

IR (Nujol): 1705, 1750 cm$^{-1}$.

NMR (CDCl$_3$, δ): 1.47 (9H, s), 2.30–2.47 (2H, m), 2.93–3.08 (1H, m), 3.37 (3H, s), 3.41–3.63 (3H, m), 3.84–4.10 (2H, m).

PREPARATION 13-5)

(2R)-1-Allyloxycarbonyl-4-carboxy-2-methoxymethylpyrrolidine was obtained in 89.9% yield in substantially the same manner as that of Preparation 11-2).

IR (Nujol): 1710 cm$^{-1}$.

NMR (CDCl$_3$, δ): 2.23–2.50 (2H, m), 3.33 (3H, s), 3.51–4.14 (6H, m), 4.56–4.63 (2H, m), 5.18–5.37 (2H, m), 5.84–6.04 (1H, m).

PREPARATION 13-6)

(2R)-4-Acetyl-1-allyloxycarbonyl-2-methoxymethylpyrrolidine was obtained in 40.9% yield in substantially the same manner as that of Preparation 2-1).

IR (Nujol): 1710 cm$^{-1}$.

NMR (CDCl$_3$, δ): 2.20 (3H, s), 3.33 (3H, d, J=7 Hz), 4.10 (1H, br s), 4.58–4.60 (2H, m), 5.18–5.34 (2H, m), 5.84–6.03 (1H, m).

PREPARATION 13-7)

(3S,4R)-4-[2-{(2S)-1-Allyloxycarbonyl-2-methoxymethylpyrrolidin-4-yl}-2-oxoethyl]-3-[(1R)-1-tert-butyldimethylsilyloxyethyl]-2-oxoazetidine was obtained in 41.4% yield in substantially the same manner as that of Preparation 3.

IR (Nujol): 1710, 1750 cm$^{-1}$.

NMR (CDCl$_3$, δ): 0.07 (6H, s), 0.87 (9H, s), 1.21 (3H, d, J=7 Hz), 3.35 (3H, s), 3.92–4.21 (3H, m), 4.58–4.62 (2H, m), 5.18–5.35 (2H, m), 5.85–6.17 (2H, m).

PREPARATION 13-8)

Allyl 2-[(3S,4R)-4-[2-{(2S)-1-allyloxycarbonyl-2-methoxymethylpyrrolidin-4-yl}-2-oxoethyl]-3-{(1R)-1-tert-butyldimethylsilyloxyethyl}-2-oxoazetidin-1-yl-]-2-oxoacetate was obtained quantitatively in substantially the same manner as that of Preparation 14-6).

IR (Nujol): 1705, 1750, 1810 cm$^{-1}$.

NMR (CDCl$_3$, δ): 0.08 (6H, s), 0.88 (9H, s), 1.23–1.29 (3H, m), 3.34 (3H, s), 4.56–4.80 (4H, m), 5.19–5.50 (4H, m), 5.86–6.04 (2H, m).

PREPARATION 14-1)

To a solution of (2S,4R)-1-benzyloxycarbonyl-2-hydroxymethyl-4-methanesulfonyloxypyrrolidine (60 g) and imidazole (12.9 g) in dichloromethane (300 ml) was added dropwise a solution of tert-butyldimethylsilyl chloride (31.4 g) in dichloromethane at 0° C. over a 30-minute period. After one hour, the reaction mixture was poured into a mixture of ethyl acetate (1 l), water (400 ml) and saturated aqueous sodium chloride (200 ml). The organic layer was separated, washed in turn with water and brine, and dried over magnesium sulfate. Evaporation of the solvent gave an oil, which was chromatographed on silica gel (1.2 l) eluting with a mixture of hexane and ethyl acetate (1:1 V/V) to give (2S,4R)-1-benzyloxycarbonyl-2-(tert-butyldimethylsilyloxy)methyl-4-methanesulfonyloxypyrrolidine (71 g).

IR (Nujol): 1710 cm$^{-1}$.

IR (CDCl$_3$, δ): 0.08 (6H, s), 0.90 (9H, s), 2.28–2.47 (2H, m), 3.03 (3H, s), 3.52–4.27 (5H, m), 5.16 (2H, s), 5.20–5.38 (1H, m), 7.36 (5H, s).

PREPARATION 14-2)

A solution of (2S,4R)-1-benzyloxycarbonyl-2-(tert-butyldimethylsilyloxy)methyl-4-methanesulfonyloxypyrrolidine (10.246 g) and sodium cyanide (3.6 g) in dimethyl sulfoxide (100 ml) was heated for three hours at 92° C. The reaction mixture was poured into a mixture of water (300 ml) and ethyl acetate (300 ml). The organic layer was separated, and the remaining aqueous layer was reextracted with ethyl acetate (200 ml). The organic layers were combined, washed with brine, and dried over magnesium sulfate. Evaporation of the solvent gave an oil, which was chromatographed on silica gel (200 ml) eluting with a mixture of hexane and ethyl acetate (2:1, V/V) to give (2S,4S)-1-benzyloxycarbonyl-2-(tert-butyldimethylsilyloxy)methyl-4-cyanopyrrolidine (4.2 g).

IR (Nujol): 1710 cm$^{-1}$.

NMR (CDCl$_3$, δ): 0.00 (6H, s), 0.88 (9H, s), 2.30–2.45 (2H, m), 2.87–3.10 (1H, m), 3.40–3.55 (1H, m), 3.65–4.18 (4H, m), 5.12 (2H, s), 7.35 (5H, s).

PREPARATION 14-3)

To a solution of methyl lithium (1 Mol solution in ether, 83.7 ml) in ether (36 ml) was added dropwise a solution of (2S,4S)-1-benzyloxycarbonyl-2-(tert-butyldimethylsilyloxy)methyl-4-cyanopyrrolidine (12 g) in ether (12 ml) at 0° C. The reaction mixture was stirred for two hours at 0° C. and one hour at room temperature. Then, to the reaction mixture was added carefully a solution of 6N-sulfuric acid (36 ml) in dioxane (72 ml), and the mixture was heated 50°–60° C. for one hour. After removal of the ether in vacuo, the remaining solution was poured into a mixture of water (120 ml) and tetrahydrofuran (120 ml), cooled at 0° C., and the pH was adjusted to pH 9.0 with 4N-aqueous sodium hydroxide. To the resulting mixture was added dropwise allyl chloroformate (14 ml) at 0° C., while adjusting the pH between 8.0 and 9.0 with 4N-aqueous sodium hydroxide. The reaction mixture was extracted with ethyl acetate (200 ml), the organic layer was separated, washed with brine, and dried over magnesium sulfate. Evaporation of the solvent gave an oil, which was chromatographed on silica gel eluting with a mixture of hexane and ethyl acetate (4:1, V/V) to give (2S)-4-acetyl-1-allyloxycarbonyl-2-hydroxymethylpyrrolidine (2.24 g).

IR (Nujol): 1700–1720, 3450 cm$^{-1}$.

NMR (CDCl$_3$, δ): 2.17 (3H, s), 2.50–2.80 (2H, m), 3.03–4.20 (6H, m), 4.57–4.70 (2H, m), 5.13–5.48 (2H, m), 5.73–6.22 (1H, m).

PREPARATION 14-4)

To a solution of (2S)-4-acetyl-1-allyloxycarbonyl-2-hydroxymethylpyrrolidine (2.14 g) and imidazole (770 mg) in dichloromethane (20 ml) was added dropwise a solution of tert-butyldimethylsilyl chloride (1.7 g) in dichloromethane (5 ml) at 0° C. After one hour, the reaction mixture was washed in turn with 1N-hydrochloric acid and brine, and dried over magnesium sulfate. Evaporation of the solvent gave an oil, which was chromatographed on silica gel eluting with a mixture of hexane and ethyl acetate (2:1, V/V) to give (2S)-4-acetyl-1-allyloxycarbonyl-2-(tert-butyldimethylsilyloxy)methylpyrrolidine (2.725 g).

IR (Nujol): 1710 cm$^{-1}$.

NMR (CDCl$_3$, δ): 0.02 (6H, s), 0.88 (9H, s), 2 20–2.32 (4H, m), 2.92–4.10 (7H, m), 4.55–4.62 (2H, m), 5.15–5.40 (2H, m), 5.85–6.00 (1H, m).

PREPARATION 14-5)

(3S,4R)-4-[2-{(2S)-1-Allyloxycarbonyl-2-hydroxymethylpyrrolidin-4-yl}-2-oxoethyl]-3-[(1R)-1-tert-butyldimethylsilyloxyethyl]-2-oxoazetidine was obtained in 49.5% yield in substantially the same manner as that of Preparation 3.

IR (Nujol): 1700–1710, 1750, 3250 cm$^{-1}$.

NMR (CDCl$_3$, δ): 0.08 (6H, s), 0.87 (9H, s), 1.21 (3H, d, J=7 Hz), 1.80–2.58 (2H, m), 2.68–4.31 (11H, m), 4.53–4.58 (2H, m), 5.03–5.38 (2H, m), 5.68–6.18 (2H, m).

PREPARATION 14-6)

To a solution of (3S,4R)-4-[2-{(2S)-1-allyloxycarbonyl-2-hydroxymethylpyrrolidin-4-yl}-2-oxoethyl]-3-[(1R)-1-tert-butyldimethylsilyloxyethyl]-2-oxoazetidine (1.64 g) and pyridine (2.8 ml) in dichloromethane (30 ml) was added dropwise a solution of tert-butyldimethylsilyl chloride (1.67 g) in dichloromethane (10 ml) at −50° C. After one hour, to the reaction mixture was added dropwise allyl oxalyl chloride (634 μl), and then, the reaction mixture was allowed to warm to room temperature. The reaction mixture was extracted with ethyl acetate, the organic layer was washed in turn with 1N-hydrochloric acid, saturated aqueous sodium bicarbonate and brine. The organic layer was dried over magnesium sulfate, and evaporated to give a residual oil, which was chromatographed on silica gel (300 ml) eluting with a mixture of hexane and ethyl acetate (4:1, V/V) to give allyl 2-[(3S,4R)-4-[2-{(2S)-1-allyloxycarbonyl-2-tert-butyldimethylsilyloxymethylpyrrolidin-4-yl}-2-oxoethyl]-3-{(1R)-1-tert-butyldimethylsilyloxyethyl}-2-oxoazetidin-1-yl]-2-oxoacetate (1.57 g).

IR (Nujol): 1710, 1750, 1810 cm$^{-1}$.

NMR (CDCl$_3$, δ): 0.08 (12H, s), 0.88 (18H, s), 1.23 (3H, d, J=7 Hz), 2.13–2.34 (2H, m), 2.90–4.37 (11H, m), 4.48–4.60 (2H, m), 4.71–4.78 (2H, m), 5.09–5.48 (4H, m), 5.68–6.16 (2H, m).

PREPARATION 15-1)

To a solution of (2S,4R)-1-(tert-butoxycarbonyl)-2-carboxy-4-hydroxypyrrolidine (103 g) and potassium carbonate (64.6 g) in dimethylformamide (500 ml) was added methyl iodide (33.2 ml) at 0° C., and the mixture was stirred for three hours. The reaction mixture was poured into a mixture of water (1 l) and ethyl acetate (1 l), and the organic layer was separated, washed in turn with water (500 ml) and brine, and dried over magnesium sulfate. Evaporation of the solvent gave an oil, which was chromatographed on silica gel (800 ml) eluting with a mixture of hexane and ethyl acetate (1:2, V/V) to give (2S,4R)-1-(tert-butoxycarbonyl)-4-hydroxy-2-methoxycarbonylpyrrolidine (105.2 g).

IR (Nujol): 1670, 1745, 3450 cm$^{-1}$.

NMR (CDCl$_3$, δ): 1.42 (9H, s), 2.00–2.40 (2H, m), 3.42–3.70 (2H, m), 3.74 (3H, s), 4.36–4.51 (2H, m).

PREPARATION 15-2)

To a solution of (2S,4R)-1-(tert-butoxycarbonyl)-4-hydroxy-2-methoxycarbonylpyrrolidine (21.46 g) and imidazole (7.74 g) in dichloromethane (150 ml) was added dropwise a solution of tert-butyldimethylsilyl chloride (14.67 g) in dichloromethane (30 ml) at room temperature. After two hours, resultant precipitate was filtered off, and the filtrate was washed in turn with water and brine. Evaporation of the solvent gave an oil, which was chromatographed on silica gel (500 ml) eluting with a mixture of hexane and ethyl acetate (2:1, V/V) to give (2S,4R)-4-(tert-butyldimethylsilyloxy)-1-(tert-butoxycarbonyl)-2-methoxycarbonylpyrrolidine (32.3 g).

NMR (CDCl$_3$, δ): 0.06 (6H, s), 0.88 (9H, s), 1.42 (9H, s), 1.94–2.27 (2H, m), 3.24–3.68 (2H, m), 3.73 (3H, s), 4.26–4.50 (2H, m).

PREPARATION 15-3)

To a solution of (2S,4R)-4-(tert-butyldimethylsilyloxy)-1-(tert-butoxycarbonyl)-2-methoxycarbonylpyrrolidine (56 g) in tetrahydrofuran (400 ml) was added slowly lithium aluminum hydride (6 g) at 0° C. After stirring for 30 minutes, to the reaction mixture were added dropwise water (6 ml), 4N-aqueous sodium hydroxide (6 ml) and water (18 ml). The precipitate was filtered off, and the solvent was removed in vacuo to give (2S,4R)-4-(tert-butyldimethylsilyloxy)-1-(tert-butoxycarbonyl)-2-hydroxymethylpyrrolidine (44.15 g).

IR (Nujol): 1700, 3400 cm$^{-1}$.

NMR (CDCl$_3$, δ): 0.06 (6H, s), 0.88 (9H, s), 1.47 (9H, s), 3.30–3.72 (4H, m), 4.10–4.34 (2H, m).

PREPARATION 15-4)

To a solution of (2S,4R)-4-(tert-butyldimethylsilyloxy)-1-(tert-butoxycarbonyl)-2-hydroxymethylpyrrolidine (5.3 g) and methanesulfonyl chloride (1.49 ml) in dichloromethane (40 ml) was added dropwise triethylamine (3.2 ml) at 0° C. After one hour, the reaction mixture was washed in turn with 1N-hydrochloric acid, water and brine. The organic layer was dried over magnesium sulfate, and evaporated to give an oil, which was chromatographed on silica gel (250 ml) eluting with a mixture of hexane and ethyl acetate (2:1, V/V) to give (2S,4R)-4-(tert-butyldimethylsilyloxy)-1-(tert-butoxycarbonyl)-2-methanesulfonyloxymethylpyrrolidine (6.06 g).

IR (Nujol): 1695, 1740 cm$^{-1}$.

NMR (CDCl$_3$, δ): 0.08 (6H, s), 0.87 (9H, s), 1.46 (9H, s), 1.93–2.10 (2H, m), 2.97 (3H, s), 3.32–3.48 (2H, m), 4.07–4.58 (3H, m).

PREPARATION 15-5)

To a solution of (2S,4R)-4-(tert-butyldimethylsilyloxy)-1-(tert-butoxycarbonyl)-2-methanesulfonyloxymethylpyrrolidine (6.0 g) in tetrahydrofuran (60 ml) was added slowly lithium aluminum hydride (1.11 g) at 0° C. And then, the reaction mixture was allowed to warm to 40° C. and stirred for one hour. To the reaction mixture were added dropwise water (1.11 ml), 4N-aqueous sodium hydroxide (1.11 ml) and water (3.33 ml). The precipitate was filtered off, and the solvent was removed in vacuo to give (2R,4R)-4-(tert-butyldimethylsilyloxy)-1-(tert-butoxycarbonyl)-2-methylpyrrolidine (4.0 g).

IR (Nujol): 1705 cm$^{-1}$.

NMR (CDCl$_3$, δ): 0.08 (6H, s), 0.87 (9H, s), 2.21 (3H, d, J=7 Hz), 1.47 (9H, s), 3.33–3.40 (2H, m), 3.63–4.35 (3H, m).

PREPARATION 15-6)

A solution of (2R,4R)-4-(tert-butyldimethylsilyloxy)-1-(tert-butoxycarbonyl)-2-methylpyrrolidine (3.9 g) and tetrabutylammonium fluoride (1 Mol-tetrahydrofuran solution, 12.4 ml) in tetrahydrofuran (40 ml) was stirred at 0° C. for one hour. The reaction mixture was extracted with ethyl acetate, the organic layer was separated, washed with brine, and dried over magnesium sulfate. Evaporation of the solvent gave an oil, which was chromatographed on silica gel (200 ml) eluting with a mixture of hexane and ethyl acetate (1:1, V/V) to give (2R,4R)-1-(tert-butoxycarbonyl)-4-hydroxy-2-methylpyrrolidine (1.96 g).

IR (Nujol): 1700, 3400 cm$^{-1}$.

NMR (CDCl$_3$, δ): 1.23 (3H, d, J=7 Hz), 1.47 (9H, s), 1.6–1.79 (1H, m), 2.00–2.17 (1H, m), 3.47 (2H, br s), 3.91–4.11 (1H, m), 4.32–4.45 (1H, m).

PREPARATION 15-7)

To a solution of (2R,4R)-1-(tert-butoxycarbonyl)-4-hydroxy-2-methylpyrrolidine (1.92 g) and methanesulfonyl chloride (955 μl) in dichloromethane (30 ml) was added dropwise triethylamine (1.99 ml) at 0° C. After one hour, the reaction mixture was washed in turn with 1N-hydrochloric acid and brine and the organic layer was dried over magnesium sulfate. Evaporation of the solvent gave an oil, which was chromatographed on silica gel (200 ml) eluting with a mixture of hexane and ethyl acetate (1:1, V/V) to give (2R,4R)-1-(tert-butoxycarbonyl)-4-methanesulfonyloxy-2-methylpyrrolidine (2.49 g).

IR (Nujol): 1695, 1740 cm$^{-1}$.

NMR (CDCl$_3$, δ): 1.27 (3H, d, J=7 Hz), 1.47 (9H, s), 1.78–1.93 (1H, m), 2.34–2.56 (1H, m), 3.03 (3H, s), 3.49–3.61 (1H, s), 3.72–4.16 (2H, m), 5.12–5.28 (1H, m).

PREPARATION 15-8)

A solution of (2R,4R)-1-(tert-butoxycarbonyl)-4-methanesulfonyloxy-2-methylpyrrolidine (2.3 g) and sodium cyanide (1.37 g) in dimethyl sulfoxide (25 ml) was heated for two and a half hours at 90° C. The reaction mixture was poured into a mixture of water (100 ml) and ethyl acetate (100 ml). The organic layer was separated, washed with brine, and dried over magnesium sulfate. Evaporation of the solvent gave an oil, which was chromatographed on silica gel (100 ml) eluting with a mixture of hexane and ethyl acetate (4:1, V/V) to give (2R,4S)-1-(tert-butoxycarbonyl)-4-cyano-2-methylpyrrolidine (1.24 g).

IR (Nujol): 1710, 2250 cm$^{-1}$.

NMR (CDCl$_3$, δ): 1.35 (3H, d, J=7 Hz), 1.47 (9H, s), 1.82–2.00 (1H, m), 2.41–2.57 (1H, m), 2.90–3.06 (1H, m), 3.48–3.60 (1H, m), 3.78–4.04 (2H, m).

PREPARATION 15-9)

(2R)-1-Allyloxycarbonyl-4-carboxy-2-methylpyrrolidine was obtained in 99.3% yield in substantially the same manner as that of Preparation 11-2).

IR (Nujol): 1710 cm⁻¹.

NMR (CDCl₃, δ): 1.28 (3H, d, J=7 Hz), 1.87–1.98 (1H, m), 2.37–2.52 (1H, m), 2.94–3.11 (1H, m), 3.56–3.65 (1H, m), 3.80–4.02 (2H, m), 4.58–4.61 (2H, m), 5.18–5.36 (2H, m), 5.84–6.04 (1H, m).

PREPARATION 15-10)

(2R)-4-Acetyl-1-allyloxycarbonyl-2-methylpyrrolidine was obtained in 54.4% yield in substantially the same manner as that of Preparation-2-1).

NMR (CDCl₃, δ): 1.24 (3H, dd, J=7 Hz), 2.20 (3H, s), 4.57–4.60 (2H, m), 5.18–5.34 (2H, m), 5.84–6.03 (1H, m).

PREPARATION 15-11)

(3S,4R)-4-[2-{(2R)-1-Allyloxycarbonyl-2-methylpyrrolidin-4-yl}-2-oxoethyl]-3-[(1R)-1-tert-butyldimethylsilyloxyethyl]-2-oxoazetidine was obtained in 55.3% yield in substantially the same manner as that of Preparation 3.

IR (Nujol): 1700, 1760 cm⁻¹.

NMR (CDCl₃, δ): 0.06 (6H, s), 0.86 (9H, s), 1.22 (6H, d, J=7 Hz), 4.57–4.60 (2H, m), 5.18–5.35 (2H, m), 5.83–6.08 (2H, m).

PREPARATION 15-12)

Allyl 2-[(3S,4R)-4-[2-{(2R)-1-allyloxycarbonyl-2-methylpyrrolidin-4-yl}-2-oxoethyl]-3-{(1R)-1-tert-butyldimethylsilyloxyethyl}-2-oxoazetidin-1-yl]-2-oxoacetate was obtained quantitatively in substantially the same manner as that of Preparation 14-6).

IR (Nujol): 1710, 1750, 1810 cm⁻¹.

NMR (CDCl₃, δ): 0.08 (6H, s), 0.87 (9H, s), 1.20–1.30 (6H, m), 1.58–1.90 (2H, m), 2.83–4.38 (9H, m), 4.57–4.80 (4H, m), 5.18–5.45 (4H, m), 5.84–6.06 (2H, m).

PREPARATION 16-1)

To a solution of (2S,4R)-1-allyloxycarbonyl-4-hydroxy-2-methoxycarbonylpyrrolidine (3.0 g) in dichloromethane (50 ml) was added hexafluoropropenediethylamine (5.4 ml) at 0° C. After stirring for 12 hours at ambient temperature, the solution was washed with saturated aqueous sodium bicarbonate and brine. The dried solution was evaporated and the residue was chromatographed on silica gel eluting with a mixture of n-hexane and ethyl acetate (3:1, V/V) to give (2S)-1-allyloxycarbonyl-4-fluoro-2-methoxycarbonylpyrrolidine 2.5 g).

IR (Neat): 1700 cm⁻¹.

NMR (CDCl₃, δ): 2.1–2.7 (2H, m), 3.75 (3H, s), 4.4–4.7 (3H, m), 5.0–5.4 (3H, m), 5.8–6.1 (1H, m).

PREPARATION 16-2)

(2S)-1-Allyloxycarbonyl-2-acetyl-4-fluoropyrrolidine was obtained in 50.9% yield in substantially the same manner as those of Preparations 12-1) and 12-3).

IR (Neat): 1700 cm⁻¹.

NMR (CDCl₃, δ): 2.20 (3H, s), 4.62 (2H, d, J=5 Hz), 4.8–5.6 (3H, m), 5.6–6.1 (1H, m).

PREPARATION 16-3)

(3S,4R)-4-{2-[(2S)-1-Allyloxycarbonyl-4-fluoropyrrolidin-2-yl]-2-oxoethyl}-3-[(1R)-1-t-butyldimethylsilyloxyethyl]-2-oxoazetidine was obtained in 66.6% yield in substantially the same manner as that of Preparation 3.

IR (CH₂Cl₂): 1750, 1700 cm⁻¹.

NMR (CDCl₃, δ): 0.06 (6H, s), 0.87 (9H, s), 1.27 (3H, d, J=6 Hz), 2.7–3.2 (3H, m), 4.5–4.7 (2H, m), 5.0–5.5 (3H, m), 5.7–6.2 (2H, m).

PREPARATION 17

(3S,4R)-4-[2-(1-Allyloxycarbonylpiperidin-2-yl)-2-oxoethyl]-3-[(1R)-1-t-butyldimethylsilyloxyethyl]-2-oxoazetidine was obtained in 53.4% yield in substantially the same manner as that of Preparation 3.

IR (CH₂Cl₂): 3400, 1760, 1700 cm⁻¹.

NMR (CDCl₃, δ): 0.04 (6H, s), 0.90 (9H, s), 2.5–2.9 (3H, m), 4.61 (2H, d, J=5 Hz), 5.1–5.3 (2H, m), 5.8–6.1 (1H, m).

PREPARATION 18-1)

To a solution of 1-allyloxycarbonyl-4-carboxypiperidine (37 g) in tetrahydrofuran (400 ml) were added triethylamine (31 ml) and isobutyl chloroformate (27 ml) at −30° C. After stirring for 30 minutes at 0° C., the precipitate was filtered off. The obtained solution was added dropwise to the solution of sodium borohydride (13 g) in water (100 ml) at 0° C. After stirring for 1 hour at 0° C., sodium chloride was added to saturate the aqueous layer, and the organic layer was separated. The dried organic layer was evaporated and then the residue was chromatographed on silica gel eluting with a mixture of n-hexane and ethyl acetate (1:1–1:2, V/V) to give 1-allyloxycarbonyl-4-hydroxymethylpiperidine (24 g).

IR (Neat): 3400–3500, 1700 cm⁻¹.

NMR (CDCl₃, δ): 1.5–1.8 (4H, m), 4.48 (2H, m), 5.1–5.4 (2H, m), 5.8–6.0 (1H, m).

PREPARATION 18-2)

To a solution of oxalyl chloride (7.7 ml) in dichloromethane (200 ml) was added dropwise dimethyl sulfoxide (7.7 ml) at −78° C. After stirring at −78° C. for 20 minutes, to the mixture was added dropwise a solution of 1-allyloxycarbonyl-4-hydroxymethylpiperidine (14 g) in dichloromethane (20 ml). After stirring at −78° C. for 30 minutes, to the mixture was added dropwise triethylamine (35 ml) and the resulting mixture was allowed to stir at 0° C. The solution was washed with brine and dried. Evaporation of the solvent gave an oil, which was dissolved in tetrahydrofuran (100 ml). To the solution was added 1N-ethylmagnesium bromide in tetrahydrofuran solution (35 ml) at 0° C. After stirring for 1 hour at 0° C., to the solution was added saturated aqueous ammonium chloride, and the organic layer was separated. The dried organic layer was evaporated, and the residue was chromatographed on silica gel eluting with a mixture of n-hexane and ethyl acetate (2:1, V/V) to give 1-allyloxycarbonyl-4-(1-hydroxypropyl)piperidine (12.8 g).

IR (Neat): 3450, 1680 cm⁻¹.

NMR (CDCl₃, δ): 0.91 (3H, t, J=7 Hz), 4.4–4.6 (2H, m), 5.0–5.4 (2H, m), 5.6–6.1 (1H, m).

PREPARATION 18-3)

1-Allyloxycarbonyl-4-(1-oxopropyl)piperidine was obtained in 35.9% yield in substantially the same manner as that of Preparation 24-2).

IR (Neat): 1710 cm⁻¹.

NMR (CDCl₃, δ): 1.05 (3H, t, J=7 Hz), 1.4–2.0 (4H, m), 2.9–3.1 (3H, m), 4.1–4.4 (3H, m), 4.5–4.6 (2H, m), 5.1–5.4 (2H, m), 5.8–6.1 (1H, m).

PREPARATION 18-4)

(3S,4R)-4-[2-(1-Allyloxycarbonylpiperidin-4-yl)-1-methyl-2-oxoethyl]-3-[(1R)-1-t-butyldimethylsilyloxyethyl]-2-oxoazetidine was obtained in substantially the same manner as that of Preparation 3. Two isomers (Isomers A and B) were separated by column chromatography on silica gel eluting with a mixture of hexane and ethyl acetate (1:1, V/V) to give Isomer A (4.9 g) and Isomer B (2.1 g).

Isomer A:
IR ($CH_2Cl_2$): 1750, 1690 $cm^{-1}$.
NMR ($CDCl_3$, δ): 0.06 (3H, s), 0.92 (9H, s), 2.6-3.1 (6H, m), 3.7-4.0 (2H, m), 4.1-4.3 (4H, m), 4.5-4.6 (2H, m), 5.1-5.4 (2H, m), 5.8-6.0 (2H, m).

Isomer B:
IR (Neat): 3300, 1750, 1700 $cm^{-1}$.
NMR ($CDCl_3$, δ): 0.06 (3H, s), 0.94 (9H, s), 2.5-3.1 (6H, m), 4.5-4.7 (2H, m), 5.1-5.4 (2H, m), 5.8-6.0 (2H, m).

PREPARATION 19

A solution of N-tert-butoxycarbonyl-3-cyanoazetidine (205 g) in conc. hydrochloric acid (100 ml) and acetic acid (1000 ml) was stirred at 130° C. for 6 hours. The solvent was removed by evaporation, and to the residue were added tetrahydrofuran (1000 ml) and water (1000 ml). To the solution was added allyl chloroformate (167 ml) at 5°-10° C., keeping the pH between 9.5 and 10.5 with 4N aqueous sodium hydroxide. The aqueous layer was separated, washed with ethyl acetate (500 ml). To the aqueous solution was added ethyl acetate (2000 ml) and the solution was adjusted to pH 1.5 with conc. hydrochloric acid with stirring. The organic layer was extracted with ethyl acetate (1000 ml) and evaporated to give 1-allyloxycarbonylazetidine-3-carboxylic acid (215 g).

NMR ($CDCl_3$, δ): 3.26-3.65 (1H, m), 4.22 (4H, d, J=6 Hz), 4.57 (2H, m), 5.10-5.43 (2H, m), 5.67-6.17 (1H, m), 7.33 (1H, s).

PREPARATION 20-1)

Ethyl 4-(allyloxycarbonyl)thiomorpholine-3-carboxylate was obtained from ethyl thiomorpholine-3-carboxylate in 99.3% yield in substantially the same manner as that of Preparation 21-1).

IR (Neat): 1740, 1705 $cm^{-1}$.
NMR ($CDCl_3$, δ): 1.30 (3H, t, J=9.6 Hz), 2.46 (1H, m), 2.73 (1H, m), 2.92 (1H, dd, J=5.4 Hz, 18.6 Hz), 3.0-3.5 (2H, m), 4.05-4.45 (3H, m), 4.6-4.65 (2H, m), 5.1-5.5 (3H, m), 5.8-6.1 (1H, m).

PREPARATION 20-2)

A solution of ethyl 4-(allyloxycarbonyl)thiomorpholine-3-carboxylate (15.4 g) in a mixture of 4N aqueous sodium hydroxide (30 ml), methanol (30 ml) and tetrahydrofuran (75 ml) was refluxed for 90 minutes. The organic solvents were evaporated to give an aqueous solution. The aqueous solution was adjusted to pH 2 with concentrated hydrochloric acid, extracted with ethyl acetate (200 ml), dried over magnesium sulfate, and evaporated under reduced pressure to give 4-(allyloxycarbonyl)thiomorpholine-3-carboxylic acid (14.0 g) as a syrup.

IR (Neat): 1750-1650 $cm^{-1}$.
NMR ($CDCl_3$, δ): 2.45-3.5 (5H, m), 4.3-4.5 (1H, m), 4.6-4.65 (2H, m), 5.2-5.3 (2H, m), 5.3-5.4 (1H, m), 5.8-6.05 (1H, m), 9.62 (1H, br s).

PREPARATION 20-3)

5-[4-(Allyloxycarbonyl)thiomorpholin-3-yl]carbonyl-2,2-dimethyl-1,3-dioxane-4,6-dione was obtained in 99.9% yield in substantially the same manner as that of Preparation 22-4).

IR (Neat): 1780-1650 $cm^{-1}$.

PREPARATION 20-4)

3-Acetyl-4-(allyloxycarbonyl)thiomorpholine was obtained in 75.1% yield in substantially the same manner as that of Preparation 22-5).

IR (Neat): 1730-1690 $cm^{-1}$.
NMR ($CDCl_3$, δ): 2.21 (3H, s), 2.4-3.35 (5H, m), 4.1-4.65 (3H, m), 4.9-5.05 (1H, m), 5.2-5.4 (2H, m), 5.85-6.05 (1H, m).

PREPARATION 20-5)

To a solution of 3-acetyl-4-(allyloxycarbonyl)thiomorpholine (8.70 g) and triethylamine (4.95 ml) in dichloromethane (70 ml) was added trimethylsilyl trifluoromethanesulfonate (6.86 ml) below −60° C. under an atmosphere of nitrogen and the mixture was stirred at 0°~5° C. for 30 minutes to give corresponding silyl enol ether. On the other hand, to a solution of (3S,4R)-4-acetoxy-3-[(1R)-1-tert-butyldimethylsilyloxyethyl]-2-oxoazetidine (10.2 g) and triethylamine (4.95 ml). in dichloromethane (70 ml) was added trimethylsilyl trifluoromethanesulfonate (6.86 ml) below −60° C. under an atmosphere of nitrogen and the mixture was stirred at 0°~5° C. for 30 minutes to give corresponding N-silyl derivative. The solution of the silyl enol ether was cooled below −60° C. To this solution was added a solution of the N-silyl derivative, followed by addition of trimethylsilyl trifluoromethanesulfonate (3.45 ml), and the mixture was stirred at 0°~10° C. for 3 hours. The solution was poured into a mixture of water (140 ml) and ethyl acetate (280 ml). After stirring for 30 minutes, the solution was adjusted to pH 6.5 with saturated aqueous sodium hydrogen carbonate. The organic layer was separated, washed with brine, dried over magnesium sulfate, and concentrated under reduced pressure to give a syrup. The syrup was subjected to a column chromatography on silica gel (170 g) and eluted with a mixture of hexane and ethyl acetate (4:6, V/V) to give Isomer A of (3S,4R)-4-[2-{4-(allyloxycarbonyl)thiomorpholin-3-yl}-2-oxoethyl]-3-[(1R)-1-tert-butyldimethylsilyloxyethyl]-2-oxoazetidine (1.53 g) as a syrup.

IR (Neat): 3300-3250, 1770-1690 $cm^{-1}$.

Elution was continued to give Isomer B of (3S,4R)-4-[2-{4-(allyloxycarbonyl)thiomorpholin-3-yl}-2-oxoethyl]-3-[(1R)-1-tert-butyldimethylsilyloxyethyl]-2-oxoazetidine (1.89 g) as a syrup.

IR (Neat): 3350-3250, 1770-1690 $cm^{-1}$.

PREPARATION 20-6)

Isomer B of allyl 2-[(3S,4R)-4-[2-{4-allyloxycarbonyl)thiomorpholin-3-yl}-2-oxoethyl]-3-{(1R)-1-tert-butyldimethylsilyloxyethyl}-2-oxoazetidin-1-yl]-2-oxoacetate was obtained in 99.7% yield in substantially the same manner as that of Preparation 13-8).

IR (Neat): 1810, 1755, 1710-1690 $cm^{-1}$.

PREPARATION 21-1)

To a solution of piperazine-2-carboxylic acid dihydrochloride (20 g) in a mixture of water (100 ml) and tetrahydrofuran (100 ml) was added a solution of allyl ice-cooling with stirring, keeping the pH between 8.5 and 9.5 with 4N aqueous sodium hydroxide. After stirring for 30 minutes, the mixture was adjusted to pH 2 with concentrated hydrochloric acid and extracted with ethyl acetate. The organic layer was washed with brine, dried over magnesium sulfate, and concentrated under reduced pressure to give 1,4-bis(allyloxycarbonyl)piperazine-2-carboxylic acid (29.65 g) as a syrup.

IR (Neat): 1745-1685 cm$^{-1}$.

NMR (CDCl$_3$, δ): 2.9-3.35 (3H, m), 3.7-4.2 (2H, m), 4.5-4.85 (6H, m), 5.15-5.35 (4H, m), 5.8-6.0 (2H, m).

PREPARATION 21-2)

5-[1,4-Bis(allyloxycarbonyl)piperazin-2-yl]carbonyl-2,2-dimethyl-1,3-dioxane-4,6-dione was obtained in quantitative yield in substantially the same manner as that of Preparation 22-4).

IR (Neat): 1740-1690 cm$^{-1}$.

PREPARATION 21-3)

2-Acetyl-1,4-bis(allyloxycarbonyl)piperazine was obtained in 71.6% yield in substantially the same manner as that of Preparation 22-5).

IR (Neat): 1730-1690 cm$^{-1}$.

NMR (CDCl$_3$, δ): 2.25 (3H, s), 2.95-3.3 (3H, m), 3.8-4.1 (2H, m), 4.55-4.75 (6H, m), 5.2-5.4 (4H, m), 5.8-6.05 (2H, m).

PREPARATION 21-4)

(3S,4R)-4-[2-{1,4-Bis(allyloxycarbonyl)piperazin-2-yl}-2-oxoethyl]-3-[(1R)-1-tert-butyldimethylsilyloxyethyl]-2-oxoazetidine was obtained in 51.2% yield in substantially the same manner as that of Preparation 3.

IR (Neat): 1770-1690 cm$^{-1}$.

PREPARATION 21-5)

Allyl 2-[(3S,4R)-4-[2-{1,4-bis(allyloxycarbonyl)piperazin-2-yl}-2-oxoethyl]-3-{(1R)-1-tert-butyldimethylsilyloxyethyl}-2-oxoazetidin-1-yl]-2-oxoacetate was obtained in 99.7% yield in substantially the same manner as that of Preparation 13-8).

IR (Neat): 1810, 1760, 1690 cm$^{-1}$.

PREPARATION 22-1)

A solution of ethyl (3S)-4-benzylmorpholine-3-carboxylate (6.50 g) in methanol (130 ml) was hydrogenated under atmospheric pressure of hydrogen over 20% palladium hydroxide on carbon (0.6 g) for 3 hours at ambient temperature. The catalyst was filtered off and the methanol was evaporated to give ethyl (3S)-morpholine-3-carboxylate (3.83 g) as a syrup.

IR (Neat): 1740 cm$^{-1}$.

NMR (CDCl$_3$, δ): 1.29 (3H, t, J=7.1 Hz), 2.03 (1H, br s), 2.8-3.2 (2H, m), 3.5-3.7 (2H, m), 3.7-4.9 (2H, m), 4.01 (1H, dd, J=3.4 Hz, 11.1 Hz), 4.21 (2H, q, J=7.1 Hz).

PREPARATION 22-2)

To a solution of ethyl (3S)-morpholine-3-carboxylate (3.80 g) in a mixture of tetrahydrofuran (40 ml) and water (40 ml) was added a solution of allyl chloroformate (3.36 ml), in tetrahydrofuran (3 ml) under ice-cooling with stirring, keeping the pH between 8.5 and 9.5 with 4N aqueous sodium hydroxide. After stirring for 30 minutes, the mixture was extracted with ethyl acetate (100 ml), dried over magnesium sulfate, and evaporated to give ethyl (3S)-4-allyloxycarbonylmorpholine-3-carboxylate (5.83 g) as a syrup.

IR (Neat): 1740, 1705 cm$^{-1}$.

NMR (CDCl$_3$, δ): 1.29 (3H, t, J=7.1 Hz), 3.2-4.0 (5H, m), 4.24 (2H, q, J=7 Hz), 4.3-4.8 (4H, m), 5.1-5.5 (2H, m), 5.8-6.0 (1H, m).

PREPARATION 22-3)

A solution of ethyl (3S)-4-allyloxycarbonylmorpholine-3-carboxylate (5.90 g) in a mixture of ethanol (15 ml) and 4N aqueous sodium hydroxide (15 ml) was stirred at 30°-40° C. for one hour. Ethanol was evaporated to give an aqueous solution. The aqueous solution was adjusted to pH 2 with concentrated hydrochloric acid, extracted with ethyl acetate (100 ml), dried over magnesium sulfate, and evaporated under reduced pressure to give (3S)-4-allyloxycarbonylmorpholine-3-carboxylic acid (5.24 g) as a syrup.

IR (Neat): 1755-1660 cm$^{-1}$.

NMR (CDCl$_3$, δ): 3.2-4.0 (5H, m), 4.3-4.5 (1H, t, J=11 Hz), 4.5-4.7 (3H, m), 5.1-5.4 (2H, m), 5.8-6.1 (1H, m).

PREPARATION 22-4)

To a mixture of (3S)-4-allyloxycarbonylmorpholine-3-carboxylic acid (5.20 g) and 2,2-dimethyl-1,3-dioxane-4,6-dione (3.5 g) in dichloromethane (50 ml) were added dicyclohexylcarbodiimide (5.00 g) and 4-dimethylaminopyridine (2.96 g), in turn, under ice-cooling. The mixture was stirred under ice-cooling for 2 hours and at ambient temperature for 18 hours. Insoluble material was filtered off. The filtrate was washed with 1N hydrochloric acid (50 ml×2) and, next, brine (50 ml), dried over magnesium sulfate, and concentrated under reduced pressure to give 5-[(3S)-4-allyloxycarbonylmorpholin-3-yl]carbonyl-2,2-dimethyl-1,3-dioxane-4,6-dione (8.31 g) as a syrup.

IR (Neat): 1740-1660 cm$^{-1}$.

PREPARATION 22-5)

A solution of 5-[(3S)-4-allyloxycarbonylmorpholin-3-yl]carbonyl-2,2-dimethyl-1,3-dioxane-4,6-dione (8.30 g) in a mixture of glacial acetic acid (17 ml) and water (25 ml) was refluxed for 2 hours. After cooling, the mixture was concentrated under reduced pressure to give a syrup. A solution of the syrup in ethyl acetate (100 ml) was washed in turn with water (100 ml), saturated sodium hydrogen carbonate (100 ml), and brine (100 ml). The solution was dried over magnesium sulfate and evaporated under reduced pressure to give a syrup. The syrup was subjected to a column chromatography on silica gel (40 g) and eluted with a mixture of hexane and ethyl acetate (8:2, V/V) to give (3S)-3-acetyl-4-allyloxycarbonylmorpholine (3.7 g) as a syrup.

IR (Neat): 1730-1690 cm$^{-1}$.

NMR (CDCl$_3$, δ): 2.23 (3H, s), 3.1-4.0 (5H, m), 4.4-4.7 (4H, m), 5.2-5.4 (2H, m), 5.8-6.0 (1H, m).

PREPARATION 22-6)

(3S,4R)-4-[2-{(3S)-4-Allyloxycarbonylmorpholin-3-yl}-2-oxoethyl]-3-[(1R)-1-tert-butyldimethylsilyloxyethyl]-2-oxoazetidine was obtained in 71.5% yield in substantially the same manner as that of Preparation 3.

IR (Neat): 1760, 1725, 1705 cm$^{-1}$.

NMR (CDCl$_3$, δ): 0.07 (6H, s), 0.87 (9H, s), 1.21 (3H, d, J=8 Hz).

PREPARATION 22-7)

Allyl 2-[(3S,4R)-4-[2-{(3S)-4-allyloxycarbonylmorpholin-3-yl}-2-oxoethyl]-3-{(1R)-1-tert-butyldimethylsilyloxyethyl}-2-oxoazetidin-1-yl]-2-oxoacetate was obtained in 97.2% yield in substantially the same manner as that of Preparation 13-8).

IR (Nujol): 1810, 1760–1690 cm$^{-1}$.

NMR (CDCl$_3$, δ): 0.02 (3H, s), 0.10 (3H, s), 0.84 (9H, s), 1.26 (3H, d, J=8 Hz).

PREPARATION 23-1)

2-(N-Allyloxycarbonyl-N-benzylamino)ethanol was obtained from 2-(benzylamino)ethanol quantitatively in substantially the same manner as that of Preparation 22-2).

IR (Neat): 3450–3350, 1710–1670 cm$^{-1}$.

NMR (CDCl$_3$, δ): 3.3–3.5 (2H, m), 3.6–3.8 (2H, m), 4.57 (2H, s), 4.6–4.7 (2H, m), 5.1–5.4 (2H, m), 5.8–6.1 (1H, m), 7.2–7.4 (5H, m).

PREPARATION 23-2)

To a solution of oxalyl chloride (13.8 ml) in dichloromethane (270 ml) was added dropwise a solution of dimethyl sulfoxide (19.7 ml) in dichloromethane (30 ml) below −60° C. under atmosphere of nitrogen. After stirring the mixture at the same condition for 30 minutes, a solution of 2-(N-allyloxycarbonyl-N-benzylamino)ethanol (32.6 g) in dichloromethane (30 ml) was added to the mixture below −60° C. with stirring. After 30 minutes, triethylamine (58 ml) was added to the mixture at the same condition. The mixture was stirred below −60° C. for 30 minutes and the reaction temperature was allowed to rise to ambient temperature. The mixture was washed with water (300 ml), 1N hydrochloric acid (300 ml×2), saturated aqueous sodium hydrogen carbonate (300 ml), and brine (300 ml) successively, dried over magnesium sulfate, and concentrated under reduced pressure to give 2-(N-allyloxycarbonyl-N-benzylamino)acetaldehyde (32.9 g) as a syrup.

IR (Neat): 1735–1680 cm$^{-1}$.

NMR (CDCl$_3$, δ): 3.95 (2H, d, J=10 Hz), 4.58 (2H, s), 4.6–4.7 (2H, m), 5.2–5.4 (2H, m), 5.8–6.0 (1H, m), 7.2–7.4 (5H, m), 9.47 (1H, d, J=10 Hz).

PREPARATION 23-3)

To a solution of (trimethylsilyl)acetylene (23.75 ml) in tetrahydrofuran (250 ml) was added a 1.6M solution of butyllithium in hexane (105 ml) below −60° C. After stirring for one hour, a solution of 2-(N-allyloxycarbonyl-N-benzylamino)acetaldehyde (32.86 g) in tetrahydrofuran (30 ml) was added to the mixture below −60° C. The solution was stirred at the same condition for one hour and an aqueous saturated ammonium chloride (100 ml) was added to the reaction mixture below −60° C. After stirring at the ambient temperature for one hour, ethyl acetate (300 ml) was poured into the mixture. The solution was washed with brine (150 ml×2), dried over magnesium sulfate, and concentrated under reduced pressure to give a syrup. The syrup was subjected to a column chromatography on silica gel (300 g) and eluted with a mixture of hexane and ethyl acetate (9:1, V/V) to give 1-(N-allyloxycarbonyl-N-benzylamino)-4-trimethylsilyl-3-butyn-2-ol (19.77 g) as a syrup.

IR (Neat): 3450–3350, 2190, 1710–1680 cm$^{-1}$.

NMR (CDCl$_3$, δ): 0.17 (9H, s), 3.3–3.5 (2H, m), 4.4–4.7 (5H, m), 5.1–5.3 (2H, m), 5.8–6.0 (1H, m), 7.1–7.3 (5H, m).

PREPARATION 23-4)

Mercury(II) sulfate (3.55 g) was added to a solution of 1-(N-allyloxycarbonyl-N-benzylamino)-4-trimethylsilyl-3-butyn-2-ol (19.75 g) in a mixture of sulfuric acid (0.15 ml), ethylene glycol (60 ml), and tetrahydrofuran (120 ml). The mixture was stirred at 30°~40° C. for 35 hours. Sodium hydrogen carbonate (1 g) was added to the mixture and the mixture was stirred at 30°~40° C. for one hour. An insoluble material was filtered off and the filtrate was concentrated under reduced pressure to give a syrup. A solution of the syrup in ethyl acetate (250 ml) was washed with water (150 ml), dried over magnesium sulfate, and concentrated under reduced pressure to give an oil. The oil was subjected to a column chromatography on silica gel (400 g) and eluted with a mixture of hexane and ethyl acetate (5:5, V/V) to give 2-[2-(N-allyloxycarbonyl-N-benzylamino)-1-hydroxyethyl]-2-methyl-1,3-dioxolane (11.6 g) as a syrup.

IR (Neat): 3450–3400, 1710–1680 cm$^{-1}$.

NMR (CDCl$_3$, δ) 1.29 (3H, s), 3.1–3.3 (1H, br s), 3.3–3.6 (2H, m), 3.6–3.8 (1H, m), 3.8–4.0 (4H, m), 4.5–4.9 (4H, m), 5.2–5.3 (2H, m), 5.8–6.0 (1H, m), 7.2–7.4 (5H, m).

PREPARATION 23-5)

Tetrakis(triphenylphosphine)palladium(0) (2 g) was added to a mixture of 2-[2-(N-allyloxycarbonyl-N-benzylamino)-1-hydroxyethyl]-2-methyl-1,3-dioxolane (10.5 g), triphenylphosphine (0.86 g), and morpholine (3 ml) in tetrahydrofuran (100 ml) at ambient temperature in a stream of nitrogen. The mixture was stirred at the same condition for 2 hours and concentrated under reduced pressure to give a residue. The residue was subjected to a column chromatography on silica gel (150 g) and eluted with a mixture of methanol and chloroform (2:98, and then 5:95, V/V) to give 2-(2-benzylamino-1-hydroxyethyl)-2-methyl-1,3-dioxolane (5.60 g) as a syrup.

IR (Neat): 3450–3250 cm$^{-1}$.

NMR (CDCl$_3$, δ): 1.29 (3H, s), 2.50 (2H, br s), 2.70 (1H, dd, J=11.2 Hz, J=16.2 Hz), 2.83 (2H, dd, J=5.0 Hz, 16.2 Hz), 3.69 (1H, dd, J=5.0 Hz, 11.2 Hz), 3.81 (1H, s), 3.96 (4H, s), 7.31 (5H, s).

PREPARATION 23-6)

To a solution of 2-(2-benzylamino-1-hydroxyethyl)-2-methyl-1,3-dioxolane (5.55 g) in a mixture of tetrahydrofuran (50 ml) and water (50 ml) was added a solution of chloroacetyl chloride (1.9 ml) in tetrahydrofuran (4 ml) under ice-cooling with stirring, while keeping the pH between 8.5 and 9.5 with 4N aqueous sodium hydroxide. After stirring for one hour, the mixture was extracted with ethyl acetate (150 ml), washed with brine (50 ml), dried over magnesium sulfate, and concentrated under reduced pressure to give a syrup. The syrup was subjected to a column chromatography on silica gel (60 g) and eluted with a mixture of hexane and ethyl acetate (5:5, V/V) to give 2-[2-(N-benzyl-N-chloroacetylamino)-1-hydroxyethyl]-2-methyl-1,3-dioxolane (5.39 g) as a syrup.

IR (Nujol): 3400–3350, 1665 cm$^{-1}$.

PREPARATION 23-7)

To a suspension of sodium hydride (60% in oil, 0.75 g) in tetrahydrofuran (50 ml) was added a solution of 2-[2-(N-benzyl-N-chloroacetylamino)-1-hydroxyethyl]-

2-methyl-1,3-dioxolane (5.35 g) in tetrahydrofuran (15 ml) under ice-cooling. The mixture was heated under reflux for 4 hours and poured into a mixture of ice-water (100 ml) and ethyl acetate (150 ml). The organic layer was separated, dried over magnesium sulfate, and concentrated under reduced pressure to give a syrup. The syrup was subjected to a column chromatography on silica gel (50 g) and eluted with a mixture of hexane and ethyl acetate (7:3, V/V) to give 4-benzyl-2-(2-methyl-1,3-dioxolan-2-yl)-5-oxomorpholine (4.65 g) as a syrup.

IR (Neat): 1660–1645 cm$^{-1}$.

NMR (CDCl$_3$, δ): 1.31 (3H, s), 3.16 (1H, dd, J=4.4 Hz, 16.0 Hz), 3.37 (1H, dd, J=14.5 Hz, 16.0 Hz), 3.74 (1H, dd, J=4.5 Hz, 14.5 Hz), 3.85–4.05 (4H, m), 4.23 (1H, d, J=22.3 Hz), 4.42 (1H, d, J=22.3 Hz), 4.55 (1H, d, J=19.8 Hz), 4.67 (1H, d, J=19.8 Hz), 7.25–7.40 (5H, m).

PREPARATION 23-8)

Borane-dimethyl sulfide complex (2.2 ml) was added to a solution of 4-benzyl-2-(2-methyl-1,3-dioxolan-2-yl)-5-oxomorpholine (4.6 g) in tetrahydrofuran (60 ml) under ice-cooling. The mixture was stirred at ambient temperature for 40 hours and methanol (5 ml) was added to the mixture. After 2 hours, the mixture was concentrated under reduced pressure to give a syrup. The syrup was poured into a mixture of water (100 ml) and ethyl acetate (100 ml). The organic layer was separated, dried over magnesium sulfate, and concentrated under reduced pressure to give a syrup. The syrup was subjected to a column chromatography on silica gel (50 g) and eluted with chloroform to give 4-benzyl-2-(2-methyl-1,3-dioxolan-2-yl)morpholine (2.00 g) as a syrup.

NMR (CDCl$_3$, δ): 1.32 (3H, s), 1.9–2.2 (2H, m), 2.63 (2H, d, J=15.2 Hz), 2.90 (2H, d, J=14.8 Hz), 3.4–3.8 (4H, m), 3.8–4.0 (5H, m), 7.2–7.4 (5H, m).

PREPARATION 23-9)

A solution of 4-benzyl-2-(2-methyl-1,3-dioxolan-2-yl)morpholine (4.25 g) in methanol (42 ml) was hydrogenated under atmospheric pressure of hydrogen over 20% palladium hydroxide on carbon (1.0 g) for 30 hours at ambient temperature. The catalyst was filtered off and the filtrate was concentrated under reduced pressure to give an oil. To a solution of the oil in a mixture of water (50 ml) and tetrahydrofuran (50 ml) was added a solution of allyl chloroformate (1.8 ml) in tetrahydrofuran (4 ml) under ice-cooling with stirring, while keeping the pH between 8.5 and 9.5 with 4N aqueous sodium hydroxide. After stirring for one hour, the mixture was extracted with ethyl acetate (100 ml), washed with brine (50 ml), dried over magnesium sulfate, and concentrated under reduced pressure to give a syrup. The syrup was subjected to a column chromatography on silica gel (50 g) and eluted with a mixture of methanol and chloroform (2:98, V/V) to give 4-allyloxycarbonyl-2-(2-methyl-1,3-dioxolan-2-yl)morpholine (2.26 g) as a syrup.

IR (Neat): 1710–1690 cm$^{-1}$.

NMR (CDCl$_3$, δ): 1.35 (3H, s), 2.7–3.1 (2H, m), 3.3–3.6 (2H, m), 3.9–4.2 (7H, m), 4.6–4.65 (2H, m), 5.15–5.4 (2H, m), 5.85–6.05 (1H, m).

PREPARATION 23-10)

A solution of 4-allyloxycarbonyl-2-[2-methyl-1,3-dioxolan-2-yl)morpholine (2.20 g) in acetone (22 ml) was stirred at ambient temperature for 5 days in the presence of p-toluenesulfonic acid monohydrate (1.10 g). The mixture was concentrated under reduced pressure to give a syrup. The syrup was subjected to a column chromatography on silica gel (25 g) and eluted with a mixture of hexane and ethyl acetate (9:1, V/V) to give 2-acetyl-4-allyloxycarbonylmorpholine (1.37 g) as a syrup.

IR (Neat): 1725–1675 cm$^{-1}$.

NMR (CDCl$_3$, δ): 2.24 (3H, s), 2.8–3.1 (2H, m), 3.59 (1H, dd, J=4.1 Hz, 15.8 Hz), 3.8–4.05 (3H, m), 4.24 (1H, br d, J=17.2 Hz), 4.55–4.65 (2H, m), 5.2–5.4 (2H, m), 5.8–6.0 (1H, m).

PREPARATION 23-11)

(3S,4R)-4-[2-{4-Allyloxycarbonylmorpholin-2-yl}-2-oxoethyl]-3-[(1R)-1-tert-butyldimethylsilyloxyethyl]-2-oxoazetidine was obtained in 71.1% yield in substantially the same manner as that of Preparation 3.

IR (Neat): 1750, 1715–1695 cm$^{-1}$.

NMR (CDCl$_3$, δ): 0.07 (6H, s), 0.88 (9H, s), 1.21 (3H, d, J=8.4 Hz), 2.7–3.15 (5H, m), 3.5–3.65 (1H, m), 3.85–4.0 (4H, m), 4.1–4.3 (2H, m), 4.5–4.65 (2H, m), 5.2–5.4 (2H, m), 5.8–6.05 (2H, m).

PREPARATION 23-12)

Allyl 2-[(3S,4R)-4-{2-(4-allyloxycarbonylmorpholin-2-yl)-2-oxoethyl}-3-{(1R)-1-tert-butyldimethylsilyloxyethyl}-2-oxoazetidin-1-yl]-2-oxoacetate was obtained in 86.4% yield in substantially the same manner as that of Preparation 13-8).

IR (Neat): 1805, 1750, 1725–1690 cm$^{-1}$.

NMR (CDCl$_3$, δ): 0.03 (3H, s), 0.07 (3H, s), 0.84 (9H, s), 1.26 (3H, d, J=8.5 Hz), 2.8–3.15 (4H, m), 3.4–3.6 (2H, m), 3.85–4.0 (3H, m), 4.2–4.4 (2H, m), 4.55–4.7 (3H, m), 4.75–4.85 (2H, m), 5.2–5.5 (4H, m), 5.85–6.0 (2H, m).

PREPARATION 24-1)

To hydrazine hydrate (38.6 g) was added dropwise a solution of ethyl 2-(1-hydroxyethyl)acrylate (106 g) in ethanol (20 ml) at 0° C. After the addition, the reaction mixture was allowed to warm to room temperature and stirred for 4 hours at the same temperature. The resulting reaction mixture was chromatographed on silica gel (2.2 l) eluting in turn with chloroform and a mixture of chloroform and methanol (8:1→2:1→1:1, V/V) to give 4-(1-hydroxyethyl)-3-pyrazolidinone (68 g).

NMR (CDCl$_3$, δ): 1.25 (3H, t, J=6 Hz), 3.0–4.4 (7H, m).

PREPARATION 24-2)

To a suspension of sodium borohydride (36.14 g) in tetrahydrofuran (420 ml) was added dropwise boron trifluoride diethyl ether complex (165 ml) at 0° C. To this reaction mixture was added dropwise a solution of 4-(1-hydroxyethyl)-3-pyrazolidinone (41.25 g) in tetrahydrofuran (200 ml) at 0° C. and the mixture was stirred for 1 day at room temperature. To the reaction mixture was quenched carefully with methanol at 0° C. and remaining precipitate was filtered off. After removal of the solvent of the filtrate, the residue was diluted with a mixture of methanol (400 ml) and hydrochloric acid (60 ml), which was stirred for 1 day at room temperature. After removal of the solvent in vacuo, the remaining solution was poured into a mixture of water (400 ml) and tetrahydrofuran (500 ml), cooled to 0° C., and the pH was adjusted to pH 9.0 with 4N-aqueous sodium hydroxide. To the resulting mixture was added dropwise allyl chloroformate (84.1 ml) at 0° C., while adjusting the pH between 8.0 and 8.5 with 4N aqueous sodium hydroxide. The reaction mixture was extracted with ethyl acetate, the organic layer was separated, washed with brine, and dried over magnesium sulfate. Evaporation of the solvent gave an oil, which was chromatographed on silica gel eluting with a mixture of hexane and ethyl acetate (1:2, V/V) to give 1,2-bis(allyloxycarbonyl)-4-(1-hydroxyethyl)pyrazolidine (57.86 g).

NMR (CDCl$_3$, δ): 1.22 (3H, d, J=7 Hz), 2.23–2.64 (1H, m), 3.08–4.24 (5H, m), 4.6–4.75 (4H, m), 5.10–5.41 (4H, m), 5.70–6.13 (2H, m).

PREPARATION 24-3)

To a solution of 1,2-bis(allyloxycarbonyl)-4-(1-hydroxyethyl)pyrazolidine (13 g) in acetone (260 ml) was added dropwise Jones Reagent (2.67N, 34 ml) at 0° C. After stirring for 1 hour, to the reaction mixture was added dropwise 2-propanol (200 ml) and the reaction mixture was stirred at 0° C. for 1 hour. The precipitate was filtered off and the filtrate was evaporated to give a residual oil, which was extracted with ethyl acetate and the organic layer was separated, washed with brine, and dried over magnesium sulfate. Evaporation of the solvent gave an oil, which was chromatographed on silica gel (300 ml) eluting with a mixture of hexane and ethyl acetate (1:1, V/V) to give 4-acetyl-1,2-bis(allyloxycarbonyl)pyrazolidine (9.18 g).

NMR (CDCl$_3$, δ): 2.24 (3H, s), 3.34–3.62 (3H, m), 4.02–4.26 (2H, m), 4.64 (4H, br s), 5.20–5.38 (4H, m), 5.82–6.01 (2H, m).

PREPARATION 24-4)

(3S,4R)-4-[2-{1,2-Bis(allyloxycarbonyl)pyrazolidin-4-yl}-2-oxoethyl]-3-[(1R)-1-tert-butyldimethylsilyloxyethyl]-2-oxoazetidine was obtained in 64.5% yield in substantially the same manner as that of Preparation 3.

IR (Nujol): 1710, 1750 cm$^{-1}$.

NMR (CDCl$_3$, δ): 0.08 (6H, s), 0.87 (9H, s), 1.22 (3H, d, J=6 Hz), 2.76–2.90 (3H, m), 3.31–3.80 (3H, m), 3.86–4.36 (4H, m), 4.60–4.70 (4H, m), 5.15–5.43 (4H, m), 5.7–6.30 (3H, m).

PREPARATION 24-5)

Allyl 2-[(3S,4R)-4-[2-{1,2-bis(allyloxycarbonyl)-pyrazolidin-4-yl}-3-{(1R)-1-tert-butyldimethylsilyloxyethyl}-2-oxoazetidin-1-yl]-2-oxoacetate was obtained in 95% yield in substantially the same manner as that of Preparation 13-8).

IR (Nujol): 1705, 1750, 1805 cm$^{-1}$.

NMR (CDCl$_3$, δ): 0.07 (6H, s), 0.87 (9H, s), 1.24 (3H, d, J=6 Hz), 2.93–3.74 (6H, m), 4.00–4.38 (4H, m), 4.58–4.81 (6H, m), 5.20–5.44 (6H, m), 5.78–6.05 (3H, m).

PREPARATION 25-1)

To a suspension of sodium borohydride (18.1 g) in tetrahydrofuran (200 ml) was added dropwise boron trifluoride diethyl ether complex (83 ml) at 0° C. To this reaction mixture was added dropwise a solution of 4-(1-hydroxyethyl)-3-pyrazolidinone (20.65 g) in tetrahydrofuran (100 ml) at 0° C. and the mixture was stirred for 1 day at room temperature. The reaction mixture was quenched carefully with methanol at 0° C. and remaining precipitate was filtered off. After removal of the solvent of the filtrate, the residue was diluted with a mixture of methanol (200 ml) and conc. hydrochloric acid (30 ml), which was stirred for 1 day at room temperature. After removal of the solvent in vacuo, the remaining solution was poured into a mixture of water (200 ml) and tetrahydrofuran (250 ml), cooled to 0° C., and the pH was adjusted to 9.0 with 4N-aqueous sodium hydroxide. To the resulting mixture was added dropwise dimethylcarbamoyl chloride (19 ml) and allyl chloroformate (20.2 ml) successively at 0° C., while adjusting the pH between 8.0 and 8.5 with 4N-aqueous sodium hydroxyde. The reaction mixture was extracted with ethyl acetate, the organic layer was separated, washed with brine, and dried over magnesium sulfate. Evaporation of the solvent gave an oil, which was chromatographed on silica gel eluting in turn with a mixture of hexane and ethyl acetate (1:2, V/V) and a mixture of ethyl acetate, hexane and methanol (5:3:2, V/V) to give 2-allyloxycarbonyl-1-(dimethylcarbamoyl)-4-(1-hydroxyethyl)pyrazolidine (22.7 g).

IR (Nujol): 1680, 3400 cm$^{-1}$.

NMR (CDCl$_3$, δ): 1.19 (3H, d, J=6 Hz), 2.0–2.64 (1H, m), 3.0 (6H, s), 3.3–3.9 (5H, m), 4.60–4.65 (2H, m), 5.17–5.37 (2H, m), 5.82–6.00 (1H, m).

PREPARATION 25-2)

To a solution of oxalyl chloride (7.42 ml) in dichloromethane (250 ml) was added dropwise dimethyl sulfoxide (12.7 ml) at −70° C. To this reaction mixture was added dropwise a solution of 2-allyloxycarbonyl-1-dimethylcarbamoyl-4-(1-hydroxyethyl)pyrazolidine (22 g) in dichloromethane (40 ml), and then was added dropwise triethylamine (56.5 ml) at −70° C. The reaction mixture was allowed to warm to room temperature. The precipitate was filtered off and the filtrate was concentrated in vacuo. The residue was poured into a mixture of ethyl acetate and 1N-aqueous hydrochloric acid, and the organic layer was extracted, washed with brine, and dried over magnesium sulfate. Evaporation of the solvent gave a residual oil, which was chromatographed on silica gel eluting in turn with a mixture of hexane and ethyl acetate (1:2, V/V) and ethyl acetate to give 4-acetyl-2-allyloxycarbonyl-1-dimethylcarbamoyl-pyrazolidine (21.3 g).

IR (Nujol): 1700 cm$^{-1}$.

NMR (CDCl$_3$, δ): 2.20 (3H, s), 3.00 (6H, s), 3.30–3.96 (5H, m), 4.56–4.65 (2H, m), 5.12–5.41 (2H, m), 5.70–6.13 (1H, m).

PREPARATION 25-3)

(3S,4R)-4-[2-(2-Allyloxycarbonyl-1-dimethylcarbamoylpyrazolidin-4-yl)-2-oxoethyl]-3-[(1R)-1-tert-butyldimethylsilyloxyethyl]-2-oxoazetidine was obtained in 35.5% yield in substantially the same manner as that of Preparation 3.

IR (Nujol): 1700, 1750 cm$^{-1}$.

NMR (CDCl$_3$, δ): 0.08 (6H, s), 0.87 (9H, s), 1.22 (3H, d, J=7 Hz), 2.76–2.90 (3H, s), 3.00 (6H, s), 3.36–4.28 (7H, m), 4.61–4.68 (2H, m), 5.12–5.38 (2H, m), 5.83–6.00 (1H, m), 6.20–6.27 (1H, m).

PREPARATION 25-4)

Allyl 2-[(3S,4R)-4-{2-(2-allyloxycarbonyl-1-dimethylcarbamoylpyrazolidin-4-yl)-2-oxoethyl}-3-{(1R)-1-tert-butyldimethylsilyloxyethyl}-2-oxoazetidin-1-yl]-2-oxoacetate was obtained in 74.9% yield in substantially the same manner as that of Preparation 13-8).

(Nujol): 1690, 1750, 1805 cm$^{-1}$.

NMR (CDCl$_3$, δ): 0.07 (6H, s), 0.84 (9H, s), 1.25 (3H, d, J=6 Hz), 2.97 (3H, s), 2.99 (3H, s), 3.10–4.00 (9H, m), 4.30–4.65 (1H, m), 4.60–4.81 (4H, m), 5.20–5.50 (4H, m), 5.83–6.03 (2H, m).

PREPARATION 26-1)

To a solution of (2S)-5-pyrrolidone-2-carboxylic acid (75 g) in methanol (580 ml) was added dropwise thionyl chloride (150 ml) at 0° C. After the addition, the reaction mixture was allowed to warm to room temperature and stirred for two hours. The solvent was removed in vacuo, and the residue was diluted with a mixture of ethyl acetate (1 l), methanol (50 ml) and water (10 ml). To this mixture was added by portions potassium carbonate (50 g), and the mixture was stirred for two hours. The precipitate was filtered off, and the filtrate was dried over magnesium sulfate. Evaporation of the solvent gave methyl (2S)-5-pyrrolidone-2-carboxylate (82.5 g) as an oil.

IR (Nujol): 1700, 1745 cm$^{-1}$.

NMR (CDCl$_3$, δ): 2.20–2.60 (4H, m), 3.78 (3H, s), 4.23–4.30 (1H, m), 6.23 (1H, br s).

PREPARATION 26-2)

To a solution of methyl (2S)-5-pyrrolidone-2-carboxylate (80 g) in tetrahydrofuran (900 ml) was added sodium hydride (60% in oil, 23.5 g) by portions. After the addition, the reaction mixture was heated to 60° C., and benzyl bromide (69.8 ml) was added dropwise thereto. After 3 hours, the reaction mixture was cooled to room temperature and water (100 ml) was added dropwise thereto. The reaction mixture was poured into a mixture of ethyl acetate (2 l) and water (800 ml). The organic layer was separated, washed with brine, and dried over magnesium sulfate. Evaporation of the solvent gave an oil, which was chromatographed on silica gel (2 l) eluting with a mixture of hexane and ethyl acetate (1:1→1:2, V/V) to give methyl (2S)-1-benzyl-5-pyrrolidone-2-carboxylate (100.8 g).

IR (Nujol): 1690, 1745 cm$^{-1}$.

NMR (CDCl$_3$, δ): 2.00–2.63 (4H, m), 3.67 (3H, s), 3.96–4.04 (2H, m), 5.02 (1H, d, J=14 Hz), 7.18–7.36 (5H, m).

PREPARATION 26-3)

To a solution of methyl (2S)-1-benzyl-5-pyrrolidone-2-carboxylate (100 g) in tetrahydrofuran (1 l) was added lithium aluminum hydride (16.3 g) by portions with care at 0° C. After 30 minutes, to the reaction mixture were added dropwise in turn water (16.3 ml), 4N-aqueous sodium hydroxide (16.3 ml) and water (48.9 ml). The precipitate was filtered off, and the filtrate was evaporated in vacuo. The resultant was dissolved in dichloromethane (800 ml) and imidazole (40.85 g) was added thereto. To this solution was added dropwise a solution of tert-butyldimethylsilyl chloride (71.1 g) in dichloromethane (200 ml) at 0° C. After 3 hours, the precipitate was filtered off, the filtrate was poured into a mixture of ethyl acetate (2 l) and water (800 ml). The organic layer was separated and dried over magnesium sulfate. Evaporation of the solvent gave an oil, which was chromatographed on silica gel (2 l) eluting with a mixture of hexane and ethyl acetate (4:1→1:4) to give (5S)-1-benzyl-5-tert-butyldimethylsilyloxymethyl-2-pyrrolidone (105.34 g).

IR (Nujol): 1700 cm$^{-1}$.

NMR (CDCl$_3$, δ): 0.08 (6H, s), 0.87 (9H, s), 1.80–2.62 (4H, m), 3.48–3.72 (3H, m), 4.03 (1H, d, J=14 Hz), 5.00 (1H, d, J=14 Hz), 7.29 (5H, s).

PREPARATION 26-4)

To a solution of diisopropylamine (53 ml) in tetrahydrofuran (250 ml) was added dropwise n-butyllithium (1.62N in n-hexane) at −70° C. After 30 minutes, to the reaction mixture was added dropwise a solution of (5S)-1-benzyl-5-tert-butyldimethylsilyloxymethyl-2-pyrrolidone (109 g) in tetrahydrofuran (100 ml), and then to this mixture was added dropwise acetaldehyde (31 ml) and the mixture was allowed to warm to room temperature. After 3 hours, the reaction mixture was poured into a mixture of ethyl acetate (1 l) and 1N-hydrochloric acid (500 ml). The organic layer was separated, dried over magnesium sulfate, and concentrated. The resulting oil was chromatographed on silica gel (500 ml) eluting with a mixture of hexane and ethyl acetate (1:4→1:2), and the active fractions were collected. Evaporation of the solvent gave a residual oil of (2S)-1-benzyl-5-tert-butyldimethylsilyloxymethyl-3-(1-hydroxyethyl)-2-pyrrolidone which was dissolved in tetrahydrofuran (300 ml). To this solution was added dropwise a suspension of sodium borohydride (37 g) and boron trifluoride diethyl ether complex (450 ml) in tetrahydrofuran (1.2 l) at 0° C. The reaction mixture was stirred for two days at room temperature. The reaction mixture was quenched carefully with methanol (500 ml) at 0° C. and the remaining precipitate was filtered off. After removal of the solvent of the filtrate, the residue was diluted with a mixture of methanol (800 ml) and conc. hydrochloric acid (100 ml), and the mixture was stirred for 3 days at room temperature. After removal of the solvent in vacuo, the remaining solution was poured into a mixture of ethyl acetate (500 ml) and water (500 ml). The aqueous layer was separated and the pH was adjusted to 10.5. The aqueous layer was extracted with ethyl acetate (500 ml). The organic layer was separated and dried over magnesium sulfate. Evaporation of the solvent gave (2S)-1-benzyl-4-(1-hydroxyethyl)-2-hydroxymethylpyrrolidine (58.0 g).

IR (Nujol): 3350 cm$^{-1}$.

NMR (CDCl$_3$, δ): 1.03–1.18 (3H, m), 1.65–4.12 (11H, m), 7.30 (5H, s).

PREPARATION 26-5)

(2S)-1-benzyl-4-(1-hydroxyethyl)-2-hydroxymethylpyrrolidine (59 g) was hydrogenated for 10 hours in a mixture of methanol (1 l) and conc. hydrochloric acid (18 ml) with palladium on carbon (50% wet, 13 g) and palladium hydroxide (7 g) as catalysts under 6 kg/cm$^2$ hydrogen pressure. The catalysts were filtered off, and the filtrate was concentrated in vacuo. The residue was dissolved in a mixture of water (200 ml) and tetrahydrofuran (200 ml), cooled to 0° C., and the pH was adjusted to 9.0 with 4N-aqueous sodium hydroxide. To the resulting mixture was added dropwise allyl chloroformate (31 ml) at 0° C., while adjusting the pH between 8.0 and 8.5 with 4N-aqueous sodium hydroxide. The reaction mixture was extracted with ethyl acetate, and the organic layer was separated, washed with brine, and dried over magnesium sulfate. Evaporation of the solvent gave an oil, which was chromatographed on silica gel (800 ml) eluting with a mixture of hexane and ethyl acetate (1:2, V/V) to give (2S)-1-allyloxycarbonyl-4-(1-hydroxyethyl)-2-hydroxymethylpyrrolidine (31.68 g).

NMR (CDFCl$_3$, δ): 1.18–1.26 (3H, m), 1.48–2.05 (3H, m), 3.13–4.12 (6H, m), 4.59–4.62 (2H, m), 5.20–5.36 (2H, m), 5.85–6.02 (1H, m).

PREPARATION 26-6)

To a solution of (2S)-1-allyloxycarbonyl-4-(1-hydroxyethyl)-2-hydroxymethylpyrrolidine (30 g) in acetone (300 ml) was added dropwise Jones' Reagent (2.67N, 245 ml) at 0° C. After stirring for 3 hours, to the reaction mixture was added dropwise 2-propanol (500 ml), and the mixture was stirred at 0° C. for 1 hour. The precipitate was filtered off and the filtrate was evaporated to give a residual oil, which was extracted with ethyl acetate and the organic layer was separated, washed with brine, dried over magnesium sulfate. Evaporation of the solvent gave (2S)-4-acetyl-1-allyloxycarbonylpyrrolidine-2-carboxylic acid (26.56 g).

IR (Nujol): 1700 cm$^{-1}$.

NMR (CDCl$_3$, δ): 2.23 (3H, s), 2.15–2.60 (2H, m), 3.63–3.78 (2H, m), 4.39–4.70 (4H, m), 5.18–5.40 (2H, m), 5.84–6.05 (1H, m).

PREPARATION 26-7)

To a solution of (2S)-4-acetyl-1-allyloxycarbonylpyrrolidine-2-carboxylic acid (23.27 g) in tetrahydrofuran (230 ml) were added in turn 1-hydroxybenzotriazole hydrate (13.7 g), dimethylamine hydrochloride (8.27 g) and 1-ethyl-3-(3-dimethylaminopropyl)carbodiimide (18.5 ml) at 0° C. After 2 hours, the reaction mixture was poured into a mixture of ethyl acetate and water, the organic layer was separated, washed twice with saturated aqueous layer hydrogen carbonate and brine in turn. The solvent was dried over magnesium sulfate and removed in vacuo. The residue was chromatographed on silica gel (600 ml) eluting with a mixture of dichloromethane and acetone (6:1→4:1) to give (2S)-4-acetyl-1-allyloxycarbonyl-2-dimethylcarbamoylpyrrolidine (11 g).

IR (Nujol): 1650, 1705 cm$^{-1}$.

NMR (CDCl$_3$, δ): 2.20 (3H, s), 1.99–2.53 (2H, m), 2.95–3.13 (6H, m), 3.40–4.00 (3H, m), 4.50–4.85 (3H, m), 5.15–5.35 (2H, m), 5.75–6.00 (1H, m).

PREPARATION 26-8)

(3S,4R)-4-[2-{(2S)-1-Allyloxycarbonyl-2-dimethylcarbamoylpyrrolidin-4-yl}-2-oxoethyl]-3-[(1R)-1-tert-butyldimethylsilyloxyethyl]-2-oxoazetidine was obtained in 55.6% yield in substantially the same manner as that of Preparation 3.

IR (Nujol): 1650, 1700, 1750 cm$^{-1}$.

NMR (CDCl$_3$, δ): 0.08 (6H, s), 0.87 (9H, s), 1.21 (3H, d, J=7 Hz), 1.8–2.5 (2H, m), 2.60–3.20 (2H, m), 2.96 (3H, s), 3.12 (3H, s), 3.25–4.23 (6H, m), 4.52–4.65 (2H, m), 4.77–4.86 (1H, m), 5.11–5.36 (2H, m), 5.77–6.10 (2H, m).

PREPARATION 26-9)

Allyl 2-[(3S,4R)-4-[2-{(2S)-1-allyloxycarbonyl-2-dimethylcarbamoylpyrrolidin-4-yl}-2-oxoethyl]-3-{(1R)-1-tert-butyldimethylsilyloxyethyl}-2-oxoazetidin-1-yl]-2-oxoacetate was obtained in 89% yield in substantially the same manner as that of preparation 13-8).

IR (Nujol): 1650, 1700, 1755, 1805 cm$^{-1}$.

NMR (CDCl$_3$, δ): 0.08 (6H, s), 0.87 (9H, s), 1.23 (3H, d, J=7 Hz), 2.0–2.4 (2H, m), 2.97 (3H, s), 3.13 (3H, s), 3.00–4.33 (6H, m), 4.57–4.84 (5H, m), 5.18–5.45 (4H, m), 5.78–6.05 (2H, m).

PREPARATION 27-1)

1-t-Butyloxycarbonyl-3-(1-hydroxyethyl)-2-oxopyrrolidine was obtained from 1-t-butyloxycarbonyl-2-oxopyrrolidine in substantially the same manner as that of Preparation 28-1).

IR (Neat): 3400, 1780, 1710 cm$^{-1}$.

NMR (CDCl$_3$, δ): 1.1–1.4 (3H, m), 1.53 (9H, s).

PREPARATION 27-2)

To a solution of 1-t-butyloxycarbonyl-3-(1-hydroxyethyl)-2-oxopyrrolidine (15 g) in dichlormethane (200 ml) were added 3,4-dihydro-2H-pyran (11.9 ml) and p-toluenesulfonic acid (1.2 g) at 0° C. After stirring for 1 hour at the same temperature, the solution was washed in turn with saturated aqueous bicarbonate and brine. The dried solution was evaporated, and the obtained residue was chromatographed on silica gel eluting with a mixture of n-hexane and ethyl acetate (2:1–3:1, V/V) to give 1-t-butyloxycarbonyl-3-{1-(tetrahydropyran-2-yloxy)ethyl}-2-oxopyrrolidine (18.4 g).

IR (Neat): 1780, 1710 cm$^{-1}$.

NMR (CDCl$_3$, δ): 1.52 (9H, s), 1.1–1.4 (3H, m), 3.4–4.0 (4H, m), 4.1–4.4 (1H, m), 4.6–4.8 (1H, m).

PREPARATION 27-3)

To a solution of 1-t-butyloxycarbonyl-3-{1-tetrahydropyran-2-yloxy)ethyl}-2-oxopyrrolidine (18.4 g) in tetrahydrofuran (160 ml) was added 1N-methyl magnesium bromide in tetrahydrofuran (100 ml) at 0° C. After stirring for 30 minutes, saturated aqueous ammonium chloride solution was added to the solution. The organic layer was separated, dried over magnesium sulfate, and evaporated in vacuo. The residue was dissolved in a mixture of tetrahydrofuran (100 ml) and methanol (100 ml), and sodium borohydride (5.8 g) was added to this solution at 0° C. After stirring for 1 hour at the same temperature, the solvent was evaporated and extracted with ethyl acetate. The organic layer was washed in turn with 1N-hydrochloric acid, saturated sodium bicarbonate, and brine. The dried solution was evaporated and the obtained residue was chromatographed on silica gel eluting with a mixture of hexane and ethyl acetate (2:1, V/V) to give N-t-butyloxycarbonyl-N-{3-(1-hydroxyethyl)-4-(tetrahydropyran-2-yloxy)pentyl}amine (13.5 g).

IR (Neat): 3400, 1700 cm$^{-1}$.

NMR (CDCl$_3$, δ): 1.43 (9H, s), 1.1–1.4 (6H, m), 3.0–3.3 (2H, m), 4.5–4.7 (1H, m), 4.7–5.1 (1H, m).

PREPARATION 27-4)

N-t-Butyloxycarbonyl-N-{3-(1-methanesulfonyloxyethyl)-4-(terthydropyran-2-yloxy)pentyl}amine was obtained in substantially the same manner as that of Preparation 10-2).

IR (Neat): 3350, 1700 cm$^{-1}$.

NMR (CDCl$_3$, δ): 1.1–1.4 (6H, m), 1.44 (9H, s), 2.95–3.1 (3H, m), 4.5–5.3 (2H, m).

PREPARATION 27-5)

To a solution of N-t-butyloxycarbonyl-N-{3-(1-methanesulfonyloxyethyl)-4-(tetrahydropyran-2-yloxy)pentyl}amine (17 g) in dimethylformamide (200 ml) was added sodium hydride (6.6 g in 60% oil) at 0° C. After stirring for 4 hours at 38° C., the solution was poured into a mixture of ethyl acetate (400 ml) and water (400 ml). The organic layer was washed with water, 1N-hydrochloride solution, saturated sodium bicarbonate, and brine successively. The dried solution was evaporated and then the residue was chromatographed on silica gel eluting with a mixture of hexane and ethyl acetate (3:1, V/V) to give 1-t-butyloxycarbonyl-2-methyl-3-(1-tetrahydropyranyloxyethyl)pyrrolidine (10.5 g).

IR (Neat): 1690 cm$^{-1}$.

NMR (CDCl$_3$, δ): 1.1–1.4 (6H, m), 1.45 (9H, s), 4.5–4.8 (1H, m).

PREPARATION 27-6)

To a solution of 1-t-butyloxycarbonyl-2-methyl-3-(1-tetrahydropyranyloxyethyl)pyrrolidine (10.2 g) in acetic acid (100 ml) was added 6N-hydrochloric acid solution (100 ml) at ambient temperature. After stirring for 12 hours, the solvent was evaporated. The residue was dissolved into a mixture of tetrahydrofuran (50 ml) and water (50 ml). To the solution was dropwise added allyl chloroformate (4.1 ml) at 0° C., while adjusting pH to 9~10 with 30% aqueous sodium hydroxide solution. The mixture was extracted with ethyl acetate, and then the organic layer was washed with brine and dried over magnesium sulfate. The solvent was evaporated to give 1-t-butyloxycarbonyl-3-(1-hydroxyethyl)-2-methylpyrrolidine 7.45 g).

IR (Neat): 3400, 1680 cm$^{-1}$.

NMR (CDCl$_3$, δ): 1.1–1.4 (6H, m), 3.2–4.0 (4H, m), 4.4–4.7 (2H, m), 5.1–5.4 (2H, m), 5.8–6.0 (1H, m).

PREPARATION 27-7)

3-Acetyl-1-allyloxycarbonyl-2-methylpyrrolidine was obtained in 73.2% yield in substantially the same manner as that of Preparation 24-3).

IR (Neat): 1690–1710 cm$^{-1}$.

NMR (CDCl$_3$, δ): 1.2–1.4 (3H, m), 2.21 (3H, s), 2.75–2.90 (1H, m), 4.5–4.6 (2H, m), 5.1–5.4 (2H, m), 5.8–6.0 (1H, m).

PREPARATION 27-8)

(3S,4R)-4-[2-(1-Allyloxycarbonyl-2-methylpyrrolidin-3-yl)-2-oxoethyl]-3-[(1R)-1-t-butyldimethylsilyloxyethyl]-2-oxoazetidine was obtained in 59.6% yield in substantially the same manner as that of Preparation 3.

IR (Neat): 3250, 1750, 1700 cm$^{-1}$.

NMR (CDCl$_3$, δ): 0.06, 0.07 (6H, each s), 0.87 (9H, s), 1.1–1.4 (6H, m), 2.6–3.0 (3H, m), 4.5–4.6 (2H, m), 5.1–5.4 (2H, m), 5.8–6.1 (2H, m).

PREPARATION 28-1)

To a solution of lithium diisopropylamide (4.7×10$^{-3}$ mole) in tetrahydrofuran was added a solution of 1-benzyl-4-(t-butyldimethylsilyloxymethyl)-2-oxopyrrolidine (1.0 g) in tetrahydrofuran (20 ml) at −78° C. under nitrogen. The mixture was stirred for 30 minutes at −78° C., and acetaldehyde (5 ml) was added to the reaction mixture. After stirring for 30 minutes at −78° C., the solution was poured into ice water, and sodium chloride was added to saturate the aqueous phase. The organic phase was separated and the aqueous phase was extracted with ethyl acetate. The combined organic phase was dried over magnesium sulfate, and concentrated. The residue was chromatographed on silica gel eluting with a mixture of n-hexane and ethyl acetate (3:1~2:1, V/V) to give 1-benzyl-3-(1-hydroxyethyl)-4-(t-butyldimethylsilyloxymethyl)-2-oxopyrrolidine (1.01 g).

IR (Neat): 3400, 1665 cm$^{-1}$.

NMR (CDCl$_3$, δ): 0.08 (6H, s), 0.85 (9H, s), 3.0–3.4 (4H, m), 3.5–3.7 (2H, m), 3.9–4.4 (1H, m), 4.45 (1H, br s), 7.1–7.4 (5H, m).

PREPARATION 28-2)

1-Benzyl-3-(1-hydroxyethyl)-4-(hydroxymethyl)pyrrolidine was obtained quantitatively by reacting with a suspension of sodium borohydride and boron trifluoride and then with hydrochloric acid in substantially the same manner as that of Preparation 26-4).

IR (Neat): 3350 cm$^{-1}$.

NMR (D$_2$O, δ): 1.1–1.3 (3H, m), 3.4–4.1 (7H, m), 7.2–7.4 (5H, m).

PREPARATION 28-3)

1-Allyloxycarbonyl-3-(1-hydroxyethyl)-4-(hydroxymethyl)pyrrolidine was obtained in 87.0% yield in substantially the same manner as that of Preparation 26-5).

IR (Neat): 3400, 1680 cm$^{-1}$.

NMR (CDCl$_3$, δ): 1.1–1.4 (3H, m), 4.5–4.6 (2H, m), 5.1–5.5 (2H, m), 5.8–6.0 (1H, m).

PREPARATION 28-4)

1Allyloxycarbonyl-4-(t-butyldimethylsilyloxymethyl)-3-(1-hydroxyethyl)pyrrolidine was obtained in 30.9% yield by reacting with about 1-equivalent of tert-butyldimethylsilyl chloride in substantially the same manner as that of Preparation 14-1).

IR (Neat): 3400, 1690 cm$^{-1}$.

NMR (CDCl$_3$, δ): 0.08 (6H, s), 0.91 (9H, s), 1.24 (3H, d, J=7 Hz), 4.5–4.7 (2H, m), 5.1–5.4 (2H, m), 5.8–6.0 (1H, m).

PREPARATION 28-5)

3-Acetyl-1-allyloxycarbonyl-4-(t-butyldimethylsilyloxymethyl)pyrrolidine was obtained in 92.4% yield in substantially the same manner as that of Preparation 24-3).

IR (Neat): 1705 cm$^{-1}$.

NMR (CDCl$_3$, δ): 0.08 (6H, s), 0.90 (9H, s), 2.17 (3H, s), 3.0–3.4 (2H, m), 3.5–3.8 (5H, m), 4.5–4.6 (2H, m), 5.1–5.3 (2H, m), 5.8–6.0 (1H, m).

PREPARATION 28-6)

(3S,4R)-4-[2-{1-Allyloxycarbonyl-4-(t-butyldimethylsilyloxymethyl)pyrrolidin-3-yl}-2-oxoethyl]-3-[(1R)-1-t-butyldimethylsilyloxyethyl]-2-oxoazetidine was obtained in 54.8% yield in substantially the same manner as that of Preparation 3.

IR (Neat): 3250, 1750, 1700 cm$^{-1}$.

NMR (CDCl$_3$, δ): 0.07, 0.06 (6H, each s), 0.86, 0.88 (9H, each s), 1.24 (3H, d, J=7 Hz), 3.4–3.8 (4H, m), 3.9–4.2 (2H, m), 4.5–4.6 (2H, m), 5.1–5.3 (2H, m), 5.8–6.0 (1H, m), 6.03 (1H, br s).

PREPARATION 29-1)

To a solution of (R)-thiazolidine-4-carboxylic acid (20.0 g) in a mixture of water (100 ml) and tetrahydrofuran (100 ml) was added a solution of 4-nitrobenzyloxycarbonyl chloride (32.4 g) in tetrahydrofuran (60 ml) under ice-cooling with stirring, keeping the pH between 8.5 and 9.0 with 4N aqueous sodium hydroxide. After stirring for 30 minutes, the mixture was adjusted to pH 1 with concentrated hydrochloric acid, extracted with ethyl acetate, dried over magnesium sulfate, and evaporated under reduced pressure to give (R)-3-(4-nitrobenzyloxycarbonyl)thiazolidine-4-carboxylic acid (54.5 g) as a crude syrup.

IR (Neat): 1720-1680 cm$^{-1}$.

PREPARATION 29-2)

5-[(4R)-3-(4-Nitrobenzyloxycarbonyl)thiazolidin-4-yl]carbonyl-2,2-dimethyl-1,3-dioxane-4,6-dione was obtained in 75.4% yield in substantially the same manner as that of Preparation 20-3).

IR (CHCl$_3$): 1725-1660 cm$^{-1}$.

PREPARATION 29-3)

(4R)-4)-Acetyl-3-(4-nitrobenzyloxycarbonyl)thiazolidine was obtained in 56.5% in substantially the same manner as that of Preparation 20-4).

IR (Nujol): 1725, 1690 cm$^{-1}$.

NMR (CDCl$_3$, δ): 2.25 (3H, s), 3.1-3.45 (2H, m), 4.5-5.0 (3H, m), 5.29 (2H, s), 7.45-7.6 (2H, m), 8.15-8.25 (2H, m).

PREPARATION 29-4)

(3S,4R)-3-[(1R)-1-tert-Butyldimethylsilyloxyethyl]-4-[2-{(4R)-3-(4-nitrobenzyloxycarbonyl)thiazolidin-4-yl}2-oxoethyl]-2-oxoazetidine was obtained in 61.8% yield in substantially the same manner as that of Preparation 20-5).

IR (CHCl$_3$): 1755, 1705 cm$^{-1}$.

NMR (CDCl$_3$, δ): 0.05 (6H, s), 0.85 (9H, s), 1.18 (3H, d, J=5.6 Hz).

PREPARATION 29-5)

4-Nitrobenzyl-2-[(3S,4R)-3-{(1R)-1-tert-butyldimethylsilyloxyethyl}-4-[2-{(4R)-3-(4-nitrobenzyloxycarbonyl)thiazolidin-4-yl}-2-oxoethyl]-2-oxoazetidin-1-yl]-2-oxoacetate was obtained in 80.7% yield in substantially the same manner as that of Preparation 20-6).

IR (CHCl$_3$): 1805, 1755-1685 cm$^{-1}$.

PREPARATION 30-1)

To a suspension of (2S,3R)-2-(benzyloxycarbonylamino)-3-hydroxybutyric acid (100 g) and 1-hydroxybenzotriazole (53.5 g) in tetrahydrofuran (800 ml) was added portionwise 1-(3-dimethylaminopropyl)-3-ethylcarbodiimide hydrochloride (75.6 g) at −10°~0° C. and the mixture was stirred at the same temperature for one hour. This cold mixture was added dropwise to concentrated ammonia water (800 ml) at 0°~10° C. The mixture was stirred at 0°~10° C. for two hours and ethyl acetate (1.6 l) was added to this mixture. The organic layer was washed with water, 1N hydrochloric acid, saturated aqueous sodium hydrogen carbonate solution, and brine, in turn, dried over magnesium sulfate, and concentrated under reduced pressure to give a syrup. The syrup was triturated to give (2S,3R)-2-(benzyloxycarbonylamino)-3-hydroxybutylamide (71.3 g) as a solid.

mp: 96°-98° C.

IR (Nujol): 3450-3200, 1660-1650 cm$^{-1}$.

NMR (CDCl$_3$, δ): 1.10 (3H, d, J=5.6 Hz), 4.0–4.2 (2H, m), 4.29 (2H, br s), 5.06 (2H, s), 6.29 (1H, d, J=8.3 Hz), 6.62 (1H, s), 6.84 (1H, s), 7.29 (5H, s).

PREPARATION 30-2)

To a solution of (2S,3R)-2-benzyloxycarbonyl-3-hydroxybutylamide (71.1 g) in tetrahydrofuran (1.4 l) was added borane-dimethyl sulfide complex (85 ml) under ice-cooling with stirring and the mixture was stirred at ambient temperature for 2 days. To the mixture was added dropwise methanol (220 ml) under ice-cooling. The mixture was concentrated under reduced pressure to give a residue. The residue was dissolved in methanol. To this solution was added a solution of hydrogen chloride (37.5 g) in methanol (250 ml) and the solution was stirred at ambient temperature for 24 hours. The solution was concentrated under reduced pressure to give a syrup. To a solution of the syrup in a mixture of water (350 ml) and tetrahydrofuran (350 ml) was added a solution of benzyl chloroformate (40.1 ml) in tetrahydrofuran (120 ml) under ice-cooling with stirring, while keeping the pH between 8.5-9.5 with 4N aqueous sodium hydroxide. After stirring for 30 minutes. The mixture was extracted with ethyl acetate (700 ml), dried over magnesium sulfate, and evaporated under reduced pressure to give a syrup. The syrup was subjected to a column chromatography on silica gel (710 g) and eluted with a mixture of methanol and chloroform (1:99, V/V) to give (2R,3R)-1,2-bis(benzyloxycarbonylamino)-3-hydroxybutane (74.16 g) as a syrup.

IR (Neat): 3450-3300, 1720-1680 cm$^{-1}$.

NMR (CDCl$_3$, δ): 1.16 (3H, d, J=6.4 Hz).

PREPARATION 30-3)

A solution of (2R,3R)-1,2-bis(benzyloxycarbonylamino)-3-hydroxybutane (80.5 g) in methanol (800 ml) was hydrogenated under atmospheric pressure of hydrogen over palladium on carbon (10%, 8 g) for 5 hours at ambient temperature. The catalyst was filtered off and the filtrate was concentrated under reduced pressure to give a syrup. To a solution of the syrup in a mixture of water (400 ml) and tetrahydrofuran (400 ml) in tetrahydrofuran (90 ml) under ice-cooling with stirring, keeping the pH between 8.5 and 9.5 with 4N aqueous sodium hydroxide. After stirring for one hour, the mixture was extracted with ethyl acetate (800 ml), washed with brine (400 ml), dried over magnesium sulfate, and concentrated under reduced pressure to give a syrup. The syrup was subjected to a column chromatography on silica gel (600 g) and eluted with a mixture of methanol and chloroform (1:99, V/V) to give (2R,3R)-1,2-bis(allyloxycarbonylamino)-3-hydroxybutane (41.78 g) as a syrup.

IR (Neat): 3400-3300, 1730-1675 cm$^{-1}$.

NMR (CDCl$_3$, δ): 1.19 (3H, d, J=6.4 Hz).

PREPARATION 30-4)

(2R)-1,2-Bis(allyloxycarbonylamino)-3-oxobutane was obtained in 79.3% yield in substantially the same manner as that of Preparation 24-2).

IR (Neat): 3450, 1730-1680 cm$^{-1}$.

NMR (CDCl$_3$, δ): 2.31 (3H, s).

PREPARATION 30-5)

(3S,4R)-4-[(3R)-3,4-Bis(allyloxycarbonylamino)-2-oxobutyl]-3-[(1R)-1-tert-butyldimethylsilyloxyethyl]-2-oxoazetidine was obtained in 66.9% yield in substantially the same manner as that of Preparation 3.

IR (Neat): 3325, 1755-1700 cm$^{-1}$.

NMR (CDCl$_3$, δ): 0.05 (6H, s), 0.85 (9H, s), 1.18 (3H, d, J=6.3 Hz).

PREPARATION 30-6)

Allyl 2-[(3S,4R)-4-{(3R)-3,4-bis(allyloxycarbonylamino-2-oxobutyl}-3-{(1R)-1-tert-butyldimethylsilyloxy)ethyl}-2-oxoazetidin-1-yl]-2-oxoacetate was obtained in 88.6% yield in substantially the same manner as that of Preparation 13-8).

IR (Neat): 3350, 1805, 1760–1685 cm⁻¹.

NMR (CDCl₃, δ): 0.03 (3H, s), 0.07 (3H, s), 0.84 (9H, s), 1.23 (3H, d, J=7.2 Hz).

PREPARATION 30-7)

Allyl (5R,6S)-3-[(1S)-1,2-bis(allyloxycarbonylamino)ethyl]-6-[(1R)-1-tert-butyldimethylsilyloxyethyl]-7-oxo-1-azabicyclo[3.2.0]hept-2-ene-2-carboxylate was obtained in 70.8% yield in substantially the same manner as that of Example 6.

IR (CHCl₃): 3340, 1775, 1725–1700 cm⁻¹.

NMR (CDCl₃, δ): 0.07 (6H, s), 0.90 (9H, s), 1.16 (3H, d, J=6.2 Hz).

PREPARATION 30-8)

Allyl (5R,6S)-3-[(1S)-1,2-bis(allyloxycarbonylamino)ethyl]-6-[(1R)-1-hydroxyethyl]-7-oxo-1-azabicyclo[3.2.0]hept-2-ene-2-carboxylate was obtained in 65.0% yield in substantially the same manner as that of Example 7.

IR (Nujol): 3400–3300, 1775–1760, 1725–1685 cm⁻¹.

NMR (CDCl₃, δ): 1.33 (3H, d, J=6.3 Hz).

PREPARATION 30-9)

(5R,6S)-3-[(1S)-1,2-Diaminoethyl]-6-[(1R)-1-hydroxyethyl]-7-oxo-1-azabicyclo[3.2.0]hept-2-ene-2-carboxylic acid was obtained quantitatively as a crude solid in substantially the same manner as that of Example 9.

IR (Nujol): 1765–1745 cm⁻¹.

EXAMPLE 1-1)

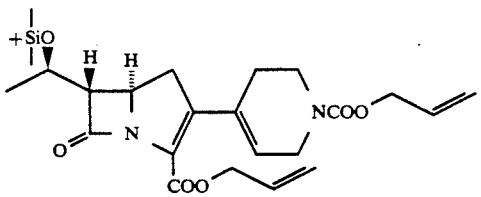

Allyl 2-[(3S,4R)-4-{2-(1-allyloxycarbonyl-1,2,3,6-tetrahydropyridin-4-yl)-2-oxoethyl}-3-{(1R)-1-t-butyldimethylsilyloxyethyl}-2-oxoazetidin-1-yl]-2-triphenylphosphoranylideneacetate (2.0 g) was dissolved in degassed toluene (40 ml) and the solution was heated to reflux for 8 hours. Evaporation of the solvent gave a residue, which was chromatographed on silica gel (50 g) eluting with a mixture of n-hexane and ethyl acetate (19:1-7:3 V/V) to give allyl (5R,6S)-3-(1-allyloxycarbonyl-1,2,3,6-tetrahydropyridin-4-yl)-6-[(1R)-1-t-butyldimethylsilyloxyethyl]-7-oxo-1-azabicyclo[3.2.0]hept-2-ene-2-carboxylate (0.94 g).

IR (CH₂Cl₂): 1775, 1700 cm⁻¹.

NMR (CDCl₃, δ): 0.10 (6H, s), 0.91 (9H, s), 1.26 (3H, d, J=6 Hz), 2.13–2.70 (2H, m), 2.87–3.20 (3H, m), 3.23–3.90 (2H, m), 4.00–4.36 (4H, m), 4.50–4.82 (4H, m), 5.10–5.55 (4H, m), 5.65–6.20 (3H, m).

EXAMPLE 1-2)

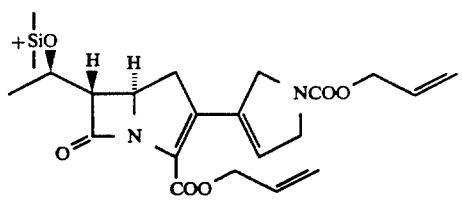

Allyl (5R,6S)-3-(1-allyloxycarbonyl-3-pyrrolin-3-yl)-6-[(1R)-1-t-butyldimethylsilyloxyethyl]-7-oxo-1-azabicyclo[3.2.0]hept-2-ene-2-carboxylate was obtained in 77.0% yield in substantially the same manner as that of Example 1-1).

IR (CHCl₃): 1780, 1700 cm⁻¹.

NMR (CDCl₃, δ): 0.10 (6H, s), 0.90 (9H, s), 1.25 (3H, d, J=6.0 Hz), 2.90–3.20 (3H, m), 4.00–4.40 (6H, m), 4.50–4.80 (4H, m), 5.08–5.52 (4H, m), 5.66–6.20 (3H, m).

EXAMPLE 2-1)

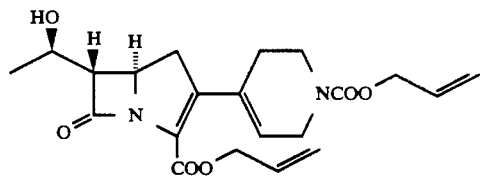

To a solution of allyl (5R,6S)-3-(1-allyloxycarbonyl-1,2,3,6-tetrahydropyridin-4-yl)-6-[(1R)-1-t-butyldimethylsilyloxyethyl]-7-oxo-1-azabicyclo[3.2.0]hept-2-ene-2-carboxylate (0.94 g) in tetrahydrofuran (38 ml) were added dropwise acetic acid (1.65 ml) and a solution of tetrabutylammonium fluoride in tetrahydrofuran (1M, 9.6 ml) at 0° C. After standing at ambient temperature for 8 hours, the reaction mixture was taken up into a mixture of ethyl acetate (300 ml) and water (300 ml). After adjusting pH to around 7 with aqueous sodium hydrogen carbonate the organic layer was separated washed in turn with water and brine and dried over magnesium sulfate. Evaporation of the solvent gave a residue, which was chromatographed on silica gel (25 g) eluting with a mixture of n-hexane and ethyl acetate (9:1-3:7, V/V) to give allyl (5R,6S)-3-(1-allyloxycarbonyl-1,2,3,6-tetrahydropyridin-4-yl)-6-[(1R)-1-hydroxyethyl]-7-oxo-1-azabicyclo[3.2.0]hept-2-ene-2-carboxylate (281 mg).

IR (CH₂Cl₂): 1780 1700 cm⁻¹.

NMR (CDCl₃, δ): 1.38 (3H, d, J=7 Hz), 2.15–2.50 (2H, m), 3.05 (2H, d, J=9 Hz), 3.19 (1H, dd, J=3, 7 Hz), 3.30–3.96 (2H, m), 3.96–4.40 (4H, m), 4.50–4.88 (4H, m), 5.10–5.60 (4H, m), 5.65–6.23 (3H, m).

EXAMPLE 2-2)

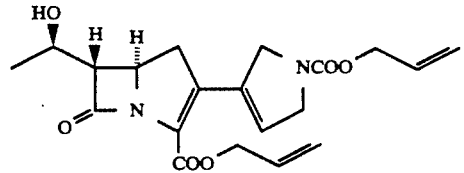

Allyl (5R,6S)-3-(1-allyloxycarbonyl-3-pyrrolin-3-yl)-6-[(1R)-1-hydroxyethyl]-7-oxo-1-azabicyclo[3.2.0]hept- 2-ene-2-carboxylate was obtained in 57.2% yield in substantially the same manner as that of Example 2-1).

IR (CHCl₃): 1780, 1700 cm⁻¹.

NMR (CDCl₃, δ): 1.33 (3H, d, J=6.0 Hz), 2.63 (1H, br s), 3.12 (2H, m), 3.22 (1H, dd, J=3.0 and 6.0 Hz), 4.00–4.90 (10H, m), 5.00–5.60 (4H, m), 5.60–6.20 (3H, m).

EXAMPLE 3-1)

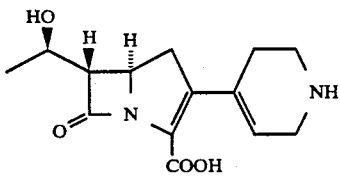

To a solution of allyl (5R,6S)-3-(1-allyloxycarbonyl-1,2,3,6-tetrahydropyridin-4-yl)-6-[(1R)-1-hydroxyethyl]-7-oxo-1-azabicyclo[3.2.0]hept-2-ene-2-carboxylate (0.280 g) in tetrahydrofuran (9 ml) were added successively triphenylphosphine (0.094 g), 5,5-dimethyl-1,3-cyclohexanedione (dimedone) (0.201 g) and tetrakis(triphenylphosphine) palladium(0) (41.5 mg). After stirring at ambient temperature for 1 hour, the mixture was poured into a mixture of cold water (50 ml) and ethyl acetate (30 ml). The separated aqueous layer was washed with ethyl acetate (30 ml×2) and concentrated in vacuo to remove the organic solvent. The residue was chromatographed on acid aluminum oxide (3 ml) eluting with water. The fractions containing the desired compound were collected and chromatographed on nonionic adsorption resin, "Diaion HP-20" (Trademark, made by Mitsubishi Chemical Industries) (20 ml) eluting with water. The fractions containing the desired compound were collected and lyophilized to give (5R,6S)-6-[(1R)-1-hydroxyethyl]-7-oxo-3-(1,2,3,6-tetrahydropyridin-4-yl)-1-azabicyclo[3.2.0]hept-2-ene-2-carboxylic acid (68 mg).

IR (Nujol): 3250, 1745 cm⁻¹.

NMR (D₂O, δ): 1.31 (3H, d, J=7 Hz), 2.20–2.88 (2H, m), 2.88–3.20 (2H, m), 3.20–3.56 (3H, m), 3.70–3.95 (2H, m), 4.02–4.40 (2H, m), 5.55–5.83 (1H, m).

EXAMPLE 3-2)

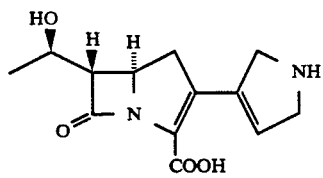

(5R,6S)-6-[(1R)-1-Hydroxyethyl]-7-oxo-3-(3-pyrrolin-3-yl)-1-azabicyclo[3.2.0]hept-2-ene-2-carboxylic acid was obtained in 79.0% yield in substantially the same manner as that of Example 3-1).

IR (Nujol): 3300, 1760 cm⁻¹.

NMR (D₂O, δ): 1.29 (3H, d, J=6.0 Hz), 3.10 (1H, d, J=11.0 Hz), 3.00–3.22 (2H, m), 3.46 (1H, dd, J=3.0 and 6.0 Hz), 3.90–4.85 (6H, m), 5.89 (1H, m).

EXAMPLE 4

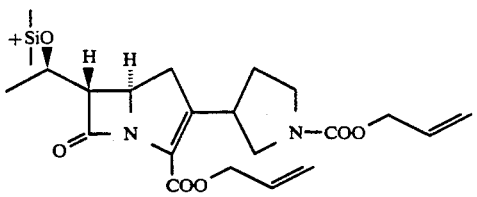

To a solution of (3S,4R)-4-[2-(1-allyloxycarbonylpyrrolidin-3-yl)-2-oxoethyl]-3-[(1R)-1-t-butyldimethylsilyloxyethyl]-2-oxoazetidine (2.13 g) and triethylamine (1.4 ml) in dichloromethane (30 ml) was added allyl oxalyl chloride (1.1 g) at −20° C. under nitrogen, and the resulting mixture was stirred for 30 minutes at −20° C. The reaction mixture was taken up into a mixture of water and ethyl acetate. The organic layer was separated, washed in turn with water, aqueous sodium hydrogen carbonate and brine, dried over magnesium sulfate, and evaporated. To a solution of the residue in xylene (30 ml) was added triethyl phosphite (5.2 ml). The resulting mixture was heated at 90° C. for 15 hours under nitrogen, and then to the mixture was added hydroquinone (0.9 g) and the mixture was heated at 130° C. for 2 hours under nitrogen. Evaporation of the solvent gave a residue, which was chromatographed on silica gel eluting with a mixture of n-hexane and ethyl acetate (4:1, V/V) to give allyl (5R,6S)-3-(1-allyloxycarbonylpyrrolidin-3-yl)-6-[(1R)-1-t-butyldimethylsilyloxyethyl]-7-oxo-1-azabicyclo[3.2.0]hept-2-ene-2-carboxylate (2.9 g).

IR (CH₂Cl₂): 1775, 1690–1710 cm⁻¹.

NMR (CDCl₃, δ): 0.14 (6H, s), 0.81 (9H, s), 1.9–2.2 (2H, m), 2.8–3.8 (6H, m), 3.9–4.2 (4H, m), 4.3–4.9 (4H, m), 5.1–5.4 (4H, m), 5.8–6.0 (2H, m).

The following compounds were obtained in substantially the same manner as that of Example 4.

EXAMPLE 5-1)

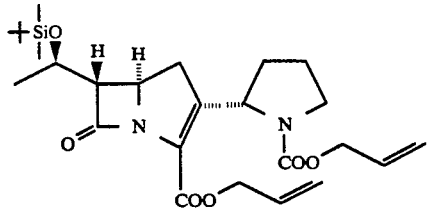

IR (CH₂Cl₂): 1765, 1690 cm⁻¹.

NMR (CDCl₃, δ): 0.03 (6H, s), 0.92 (9H, s), 1.22 (3H, d, J=6 Hz), 1.60–2.39 (4H, m), 4.42–4.83 (4H, m), 5.19–5.43 (4H, m), 5.64–6.18 (2H, m).

EXAMPLE 5-2)

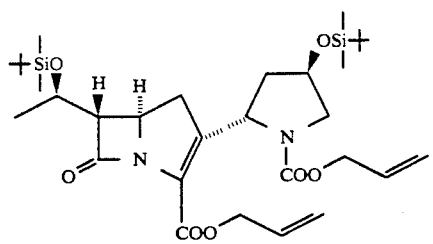

IR (CH₂Cl₂): 1780, 1710 cm⁻¹.
NMR (CDCl₃, δ): 0.03 (12H, s), 0.93 (18H, s), 2.52-2.97 (2H, m), 2.98-3.02 (1H, m), 3.20-3.43 (1H, m), 4.48-4.81 (4H, m), 5.00-5.58 (4H, m), 5.62-6.00 (2H, m).

EXAMPLE 5-3

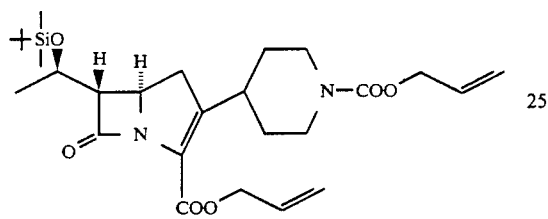

IR (CH₂Cl₂): 1770, 1690 cm⁻¹.
NMR (CDCl₃, δ): 0.03 (6H, s), 0.90 (9H, s), 2.50-2.95 (4H, m), 2.98-3.05 (1H, m), 4.50-4.70 (4H, m), 5.10-5.62 (4H, m), 5.85-6.02 (2H, m).

EXAMPLE 5-4)

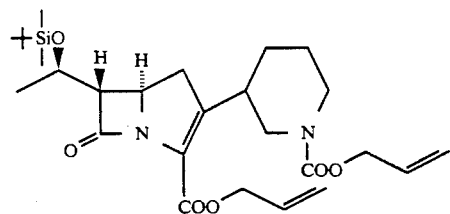

IR (CH₃Cl₂): 1770, 1690 cm⁻¹.
NMR (CDCl₃, δ): 0.03 (6H, s), 0.90 (9H, s), 1.13 (3H, d, J=6 Hz), 2.4-3.0 (5H, m), 3.2-3.5 (1H, m), 3.9-4.2 (4H, m), 4.4-4.8 (4H, m), 5.0-5.4 (4H, m), 5.6-6.0 (2H, m).

EXAMPLE 5-5)

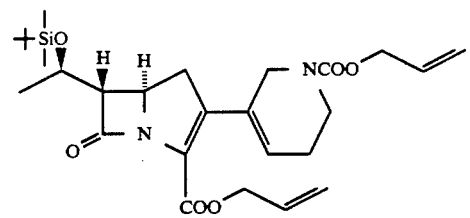

IR (CHCl₃): 1765, 1710, 1680 cm⁻¹.
NMR (CDCl₃, δ): 0.08 (6H, s), 0.88 (9H, s), 1.30 (3H, d, J=7 Hz), 2.15-2.40 (2H, m), 2.98 (2H, d, J=9 Hz), 3.10 (1H, dd, J=3, 6 Hz), 3.40-3.65 (2H, m), 3.90-4.25 (4H, m), 4.50-4.75 (4H; m), 5.05-5.55 (4H, m), 5.67-6.15 (3H, m).

EXAMPLE 5-6)

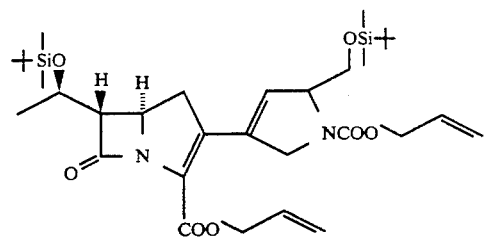

IR (CHCl₃): 1775, 1695 cm⁻¹.
NMR (CDCl₃, δ): 0.08 (6H, s), 0.12 (6H, s), 0.92 (18H, s), 1.28 (3H, d, J=7 Hz), 2.95-3.20 (2H, m), 3.50-4.50 (7H, m), 4.50-4.80 (4H, m), 5.10-5.52 (4H, m), 5.70-6.20 (3H, m).

EXAMPLE 6

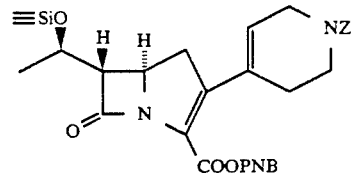

To a solution of 4-nitrobenzyl 2-[(3S,4R)-4-{2-(1-benzyloxycarbonyl-1,2,3,6-tetrahydropyridin-4-yl)-2-oxoethyl}-3-{(1R)-1-trimethylsilyloxyethyl}-2-oxoazetidin-1-yl]-2-oxoacetate (4.73 g) and triethyl phosphite (6.2 ml) in toluene (70 ml) was heated under reflux for 2 hours under nitrogen atmosphere. To this solution was added hydroquinone (800 mg), and the reflux was continued for additional 6 hours. The solvent was removed in vacuo to give a residue, which was chromatographed on silica gel (400 ml) eluting with a mixture of hexane and ethyl acetate (4:1 v/v) to give 4-nitrobenzyl (5R,6S)-3-(1-benzyloxycarbonyl-1,2,3,6-tetrahydropyridin-4-yl)-6-[(1R)-1-trimethylsilyloxyethyl]-7-oxo-1-azabicyclo[3.2.0]hept-2-ene-2-carboxylate (3.77 g).

IR (Nujol): 1660-1745 cm⁻¹.
NMR (CDCl₃, δ): 1.09 (9H, s), 1.23 (3H, d, J=7 Hz), 2.04-2.39 (2H, m), 2.90-3.20 (3H, m), 3.28-3.67 (2H, m), 3.90-4.26 (4H, m), 5.08 (2H, s), 5.26 (2H, d, J=8 Hz), 5.66-5.76 (1H, m), 7.27 (5H, s), 7.47-7.58 (2H, m), 8.07-8.17 (2H, m).

EXAMPLE 7

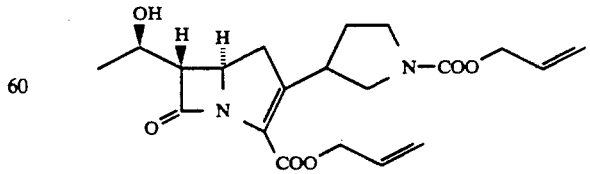

To a solution of allyl (5R,6S)-3-(1-allyloxycarbonyl-pyrrolidin-3-yl)-6-[(1R)-1-t-butyldimethylsilyoxyethyl]-7-oxo-1-azabicyclo[3.2.0]hept-2-ene-2-carboxylate (2.9 g) in tetrahydrofuran (30 ml) were added acetic acid (3.3 ml) and a 1M solution of tetrabutylammonium fluoride in tetrahydrofuran (28.7 ml) at 0° C. under nitrogen. After standing at ambient temperature for 7 hours and additionally at 5° C. for 14 hours, the reaction mixture was taken up into a mixture of ethyl acetate and water. After adjusting pH to around 7 with an aqueous sodium hydrogen carbonate, the organic layer was separated, washed in turn with water and brine, and dried over magnesium sulfate. Removal of the solvent gave a residue, which was chromatographed on silica gel eluting with a mixture of n-hexane and ethyl acetate (1:2, V/V) to give allyl (5R,6S)-3-(1-allyloxycarbonylpyrrolidin-3-yl)-6-[(1R)-1-hydroxyethyl]-7-oxo-1-azabicyclo[3.2.0]hept-2-ene-2-carboxylate (0.94 g).

IR (CH$_2$Cl$_2$): 3300–3400, 1770–1780, 1680–1710 cm$^{-1}$.

NMR (CDCl$_3$, δ): 1.8–2.2 (2H, m), 2.8–3.9 (7H, m), 4.0–4.2 (2H, m), 4.5–4.0 (4H, m), 5.1–5.7 (4H, m), 5.8–6.1 (2H, m).

The following compounds were obtained in substantially the same manner as that of Example 7.

EXAMPLE 8-1)

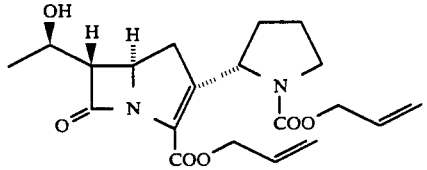

IR (CH$_2$Cl$_2$): 3300–3400, 1775, 1690–1710 cm$^{-1}$.

NMR (CDCl$_3$, δ): 1.56–2.22 (4H, m), 4.02–4.40 (2H, m), 4.40–4.88 (4H, m), 5.09–5.47 (4H, m), 5.78–6.12 (2H, m).

EXAMPLE 8-2)

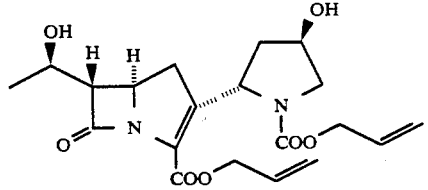

IR (CH$_2$Cl$_2$): 3400, 1770, 1680–1710 cm$^{-1}$.

NMR (CDCl$_3$, δ): 1.31 (3H, d, J=6 Hz), 3.18–3.77 (2H, m), 4.17–4.30 (2H, m), 4.31–4.85 (4H, m), 5.08–5.61 (4H, m), 5.72–6.08 (2H, m).

EXAMPLE 8-3)

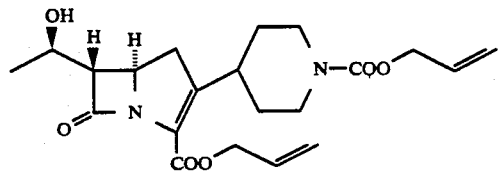

IR (CH$_2$Cl$_2$): 3400, 1775, 1690–1705 cm$^{-1}$.

NMR (CDCl$_3$, δ): 2.60–3.20 (3H, m), 4.42–4.83 (4H, m), 5.18–5.60 (4H, m), 5.81–6.07 (2H, m).

EXAMPLE 8-4)

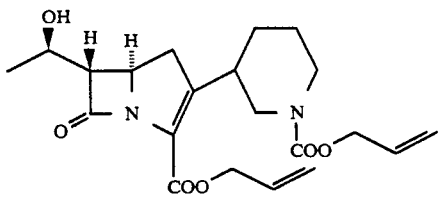

IR (CH$_2$Cl$_2$): 3100, 1780, 1690 cm$^{-1}$.

NMR (CDCl$_3$, δ): 1.33 (3H, d, J=6 Hz), 2.6–3.4 (6H, m), 4.0–4.3 (4H, m), 4.4–4.9 (4H, m), 5.0–5.5 (4H, m), 5.8–6.0 (2H, m).

EXAMPLE 8-5)

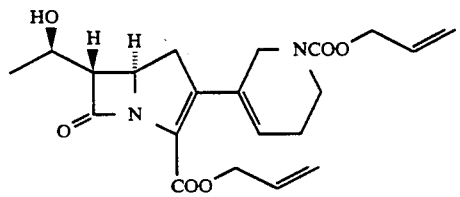

IR (CHCl$_3$): 3400, 1760, 1700, 1680 cm$^{-1}$.

NMR (CDCl$_3$, δ): 1.33 (3H, d, J=7 Hz), 2.10–2.40 (3H, m), 3.02 (2H, d, J=9 Hz), 3.15 (1H, dd, J=7, 3 Hz), 3.55 (2H, m), 4.00–4.30 (4H, m), 4.45–4.80 (4H, m), 5.05–5.50 (4H, m), 5.65–6.15 (3H, m).

EXAMPLE 8-6)

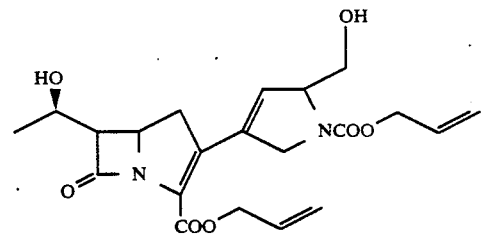

IR (CHCl$_3$): 3400, 1775, 1680 cm$^{-1}$.

NMR (CDCl$_3$, δ): 1.34 (3H, d, J=7 Hz), 2.80 (2H, br s), 3.00–3.30 (2H, m), 3.50–4.00 (3H, m), 4.00–5.00 (9H, m), 5.10–5.55 (4H, m), 5.70–6.20 (3H, m).

EXAMPLE 8-7)

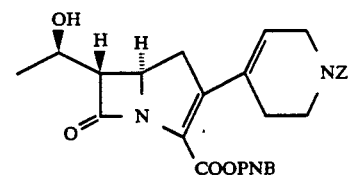

IR (Nujol): 3100–3400, 1685–1740 cm$^{-1}$.

NMR (CDCl$_3$, δ): 1.34 (3H, d, J=7 Hz), 2.15–2.44 (2H, m), 2.97–3.84 (5H, m), 3.97–4.33 (4H, m), 5.14 (2H, s), 5.31 (2H, d, J=8 Hz), 5.69–5.84 (1H, m), 7.33 (5H, s), 7.50–7.62 (2H, m), 8.12–8.23 (2H, m).

EXAMPLE 9

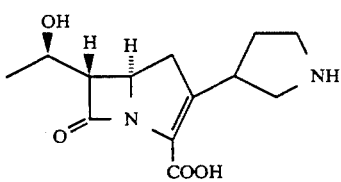

To a solution of allyl (5R,6S)-3-(1-allyloxycarbonyl-pyrrolidin-3-yl)-6-[(1R)-1-hydroxyethyl]-7-oxo-1-azabicyclo[3.2.0]hept-2-ene-2-carboxylate (0.94 g) in a mixture of tetrahydrofuran (14 ml) and ethanol (2 ml) were added successively triphenylphosphine (130 mg), 5,5-dimethyl-1,3-cyclohexanedione (dimedone) (0.66 g) and tetrakis(triphenylphosphine)palladium(0) (280 mg). Stirring at ambient temperature for 1 hour gave a precipitate, which was collected by filtration and washed with tetrahydrofuran to give (5R,6S)-6-[(1R)-1-hydroxyethyl]-7-oxo-3-(pyrrolidin-3-yl)-1-azabicyclo[3.2.0-]hept-2-ene-2-carboxylic acid (480 mg).

IR (Nujol): 1760 cm$^{-1}$.
NMR (D$_2$O, δ): 1.38 (3H, d, J=6 Hz), 1.8–2.6 (3H, m), 4.0–4.3 (2H, m).

The following compounds were obtained in substantially the same manner as that of Example 9.

EXAMPLE 10-1)

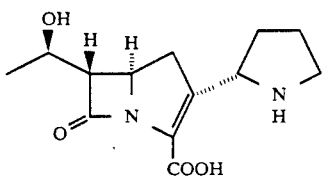

IR (Nujol): 1760 cm$^{-1}$.
NMR (D$_2$O, δ): 1.31 (3H, d, J=6 Hz), 1.80–2.52 (4H, m), 2.90–3.52 (4H, m), 4.00–4.50 (3H, m).

EXAMPLE 10-2)

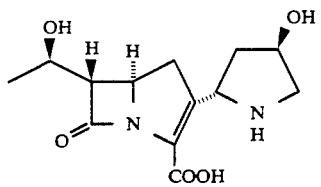

IR (Nujol): 1760 cm$^{-1}$.
NMR (D$_2$O, δ): 1.28 (3H, d, J=6 Hz), 1.80–2.60 (2H, m), 3.95–4.35 (2H, m).

EXAMPLE 10-3)

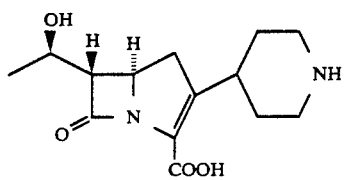

IR (Nujol): 1725–1755 cm$^{-1}$.

NMR (D$_2$O, δ): 1.26 (3H, d, J=7 Hz), 1.53–2.61, (5H, m), 2.80–4.24 (9H, m).

EXAMPLE 10-4)

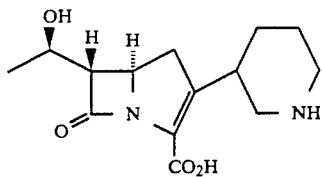

IR (Nujol): 1760 cm$^{-1}$.
NMR (D$_2$O, δ): 1.29 (3H, d, J=6 Hz), 1.3–2.2 (4H, m), 3.9–4.4 (2H, m).

EXAMPLE 10-5)

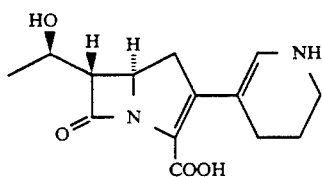

IR (Nujol): 3300, 1750, 1580 cm$^{-1}$.
NMR (D$_2$O, δ): 1.28 (3H, d, J=7 Hz), 2.52 (2H, m), 3.03 (2H, dd, J=7, 8 Hz), 3.15–3.45 (4H, m), 3.85–4.35 (3H, m), 5.94 (1H, m).

EXAMPLE 10-6)

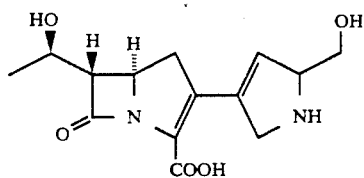

IR (Nujol): 3300, 1760, 1590 cm$^{-1}$.
NMR (D$_2$O, δ): 1.28 (3H, d, J=6.0 Hz), 3.00–3.20 (2H, m), 3.45 (1H, dd, J=3 and 6 Hz), 3.70–4.50 (7H, m), 5.78 (1H, m).

EXAMPLE 11

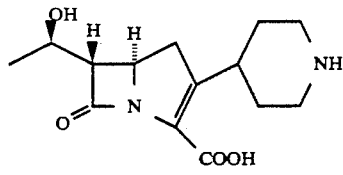

To a solution of 4-nitrobenzyl (5R,6S)-3-(1-benzyloxycarbonyl-1,2,3,6-tetrahydropyridin-4-yl)-6-[(1R)-1-hydroxyethyl]-7-oxo-1-azabicyclo[3.2.0]hept-2-ene-2-carboxylate (500 mg) in 0.1M phosphate buffer (pH 6.93, 20 ml) was added 20% (W/W) palladium on carbon (50% wet) and the solution was stirred under atmospheric pressure of hydrogen at ambient temperature for 5 hours. The catalyst was filtered off and the filtrate was concentrated in vacuo to give a residual solution, which was chromatographed on "Diaion HP-20" (100 ml) eluting in turn with water and a mixture of water and acetone (50:1–20:1, V/V). The fractions containing the desired compound were collected and lyophilized to give (5R,6S)-6-[(1R)-1-hydroxyethyl]-7-oxo-3-(piperidin-4-yl)-1-azabicyclo[3.2.0]hept-2-ene-2-carboxylic acid (150 mg).

IR (Nujol): 1725–1755 cm⁻¹.

NMR (D₂O, δ): 1.26 (3H, d, J=7 Hz), 1.53–2.61 (5H, m), 2.80–4.24 (9H, m).

EXAMPLE 12

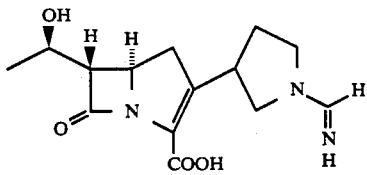

To a solution of (5R,6S)-6-[(1R)-1-hydroxyethyl]-7-oxo-3-(pyrrolidin-3-yl)-1-azabicyclo[3.2.0]hept-2-ene-2-carboxylic acid (250 mg) was added benzyl formimidate hydrochloride (0.48 g) at 0° C. while adjusting pH to 8.5 with 30% aqueous sodium hydroxide solution. After 30 minutes at the same temperature, the solution was adjusted to pH 6.5 with 1N hydrochloric acid, washed with ethyl acetate and concentrated in vacuo. The residue was chromatographed on nonionic adsorption resin "Diaion HP-20" (Trademark, made by Mitsubishi Chemical Industries) eluting with 3% aqueous isopropyl alcohol. The fractions containing the desired compound were collected and lyophilized to give (5R,6S)-3-(1-formimidoylpyrrolidin-3-yl)-6-[(1R)-1-hydroxyethyl]-7-oxo-1-azabicyclo[3.2.0]hept-2-ene-2-carboxylic acid (120 mg).

IR (Nujol): 1750, 1700 cm⁻¹.

NMR (D₂O, δ): 1.28 (3H, d, J=6 Hz), 1.8–2.4 (2H, m), 2.7–3.0 (2H, m), 7.89 (1H, br s).

The following compounds were obtained in substantially the same manner as that of Example 12.

EXAMPLE 13-1)

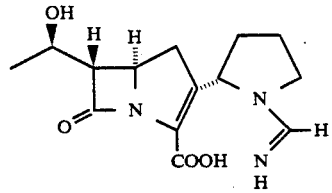

IR (Nujol): 1760, 1705 cm⁻¹.

NMR (D₂O, δ): 1.29 (3H, d, J=6 Hz), 1.60–2.45 (4H, m), 2.55–3.12 (2H, m), 7.67, 7.92 (1H, each br s).

EXAMPLE 13-2)

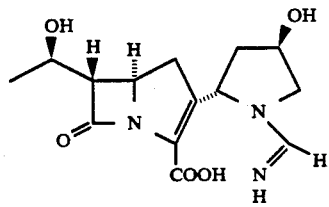

IR (Nujol): 1760, 1705 cm⁻¹.

NMR (D₂O, δ): 1.25 (3H, d, J=6 Hz), 2.00–2.52 (2H, m), 2.52–3.10 (2H, m), 7.72, 7.98 (1H, each br s).

EXAMPLE 13-3)

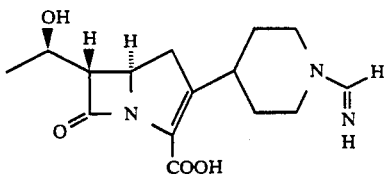

IR (Nujol): 1755, 1710 cm⁻¹.

NMR (D₂O, δ): 1.26 (3H, d, J=6 Hz), 1.20–2.20 (4H, m), 7.71 (1H, br s).

EXAMPLE 13-4)

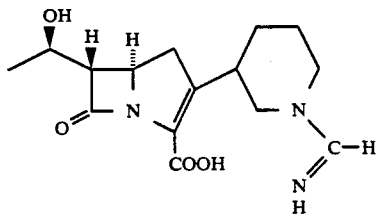

IR (Nujol): 1755, 1705 cm⁻¹.

NMR (D₂O, δ): 1.28 (3h, d, J=6 Hz), 1.3–2.2 (4H, m), 7.72 (1H, br s).

EXAMPLE 14-1)

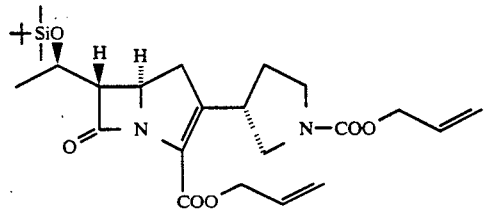

Allyl (5R,6S)-3-[(3S)-1-allyloxycarbonylpyrrolidin-3-yl]-6-[(1R)-1-t-butyldimethylsilyloxyethyl]-7-oxo-1-azabicyclo[3.2.0]hept-2-ene-2-carboxylate was obtained in 84.1% yield in substantially the same manner as that of Example 4.

IR (CH₂Cl₂): 1780, 1710 cm⁻¹.

NMR (CDCl₃, δ): 0.07 (6H, s), 0.88 (9H, s), 1.68–2.21 (2H, m), 2.64–3.72 (7H, m), 4.01–4.22 (3H, m), 4.58–4.82 (4H, m), 5.18–5.45 (4H, m), 5.87–6.71 (2H, m).

EXAMPLE 14-2)

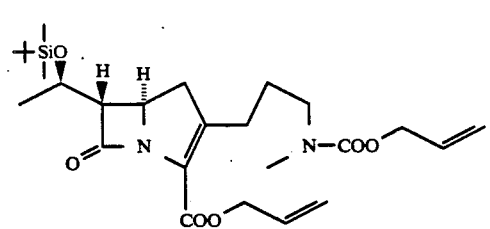

Allyl (5R,6S)-3-[(3R)-1-allyloxycarbonylpyrrolidin-3-yl]-6-[(1R)-1-t-butyldimethylsilyloxyethyl]-7-oxo-1-azabicyclo[3.2.0]hept-2-ene-2-carboxylate was obtained in 71.0% yield in substantially the same manner as that of Example 4.

IR (CH$_2$Cl$_2$): 1780, 1710 cm$^{-1}$.

NMR (CDCl$_3$, δ): 0.08 (6H, s), 0.90 (9H, s), 1.69–2.24 (2H, m), 2.72–3.73 (7H, m), 4.52–4.86 (4H, m), 5.17–5.52 (4H, m), 5.84–6.13 (2H, m).

EXAMPLE 14-3)

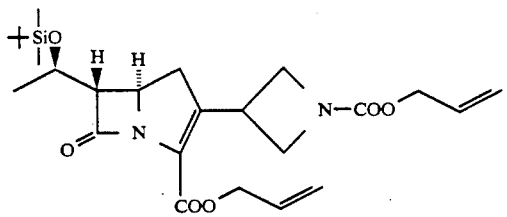

Allyl (5R,6S)-3-(1-allyloxycarbonylazetidin-3-yl)-6-[(1R)-1-t-butyldimethylsilyloxyethyl]-7-oxo-1-azabicyclo[3.2.0]hept-2-ene-2-carboxylate was obtained in 76.6% yield in substantially the same manner as that of Example 4.

IR (CH$_2$Cl$_2$): 1780, 1710 cm$^{-1}$.

NMR (CDCl$_3$, δ): 0.04 (6H, s), 0.91 (9H, s), 1.22 (3H, d, J=6 Hz), 2.89–3.12 (3H, m), 5.10–5.39 (4H, m), 5.76–5.88 (2H, m).

EXAMPLE 15-1)

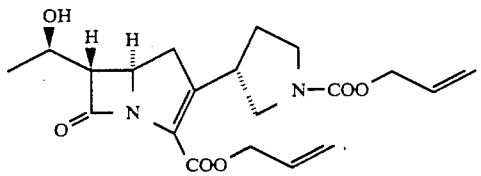

Allyl (5R,6S)-3-[(3S)-1-allyloxycarbonylpyrrolidin-3-yl]-6-[(1R)-1-hydroxyethyl]-7-oxo-1-azabicyclo[3.2.0-]hept-2-ene-2-carboxylate was obtained in 59.6% yield in substantially the same manner as that of Example 7.

IR (Neat): 3400, 1775, 1690–1710 cm$^{-1}$.

NMR (CDCl$_3$, δ): 1.34 (3H, d, J=6 Hz), 2.60–3.80 (7H, m), 4.47–4.83 (4H, m), 5.15–5.62 (4H, m), 5.80–6.07 (2H, m).

EXAMPLE 15-2)

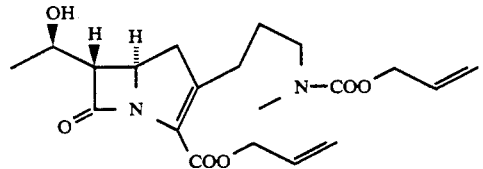

Allyl (5R,6S)-3-[(3R)-1-allyloxycarbonylpyrrolidin-3-yl]-6-[(1R)-1-hydroxyethyl]-7-oxo-1-azabicyclo[3.2.0]-hept-2-ene-2-carboxylate was obtained in 49.7% yield in substantially the same manner as that of Example 7.

IR (CH$_2$Cl$_2$): 3400, 1780, 1710 cm$^{-1}$.

NMR (CDCl$_3$, δ): 1.34 (3H, d, J=6 Hz), 2.73–3.80 (7H, m), 4.04–4.35 (2H, m), 4.50–5.00 (4H, m), 5.18–5.54 (4H, m), 5.80–6.02 (2H, m).

EXAMPLE 15-3)

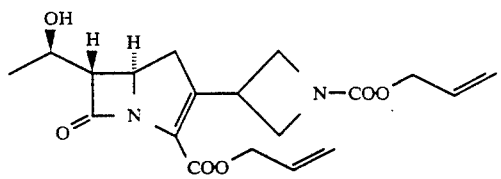

Allyl (5R,6S)-3-(1-allyloxycarbonylazetidin-3-yl)-6-[(1R)-1-hydroxyethyl]-7-oxo-1-azabicyclo[3.2.0]hept-2-ene-2-carboxylate was obtained in 62.4% yield in substantially the same manner as that of Example 7.

IR (Neat): 3400, 1780, 1690–1710 cm$^{-1}$.

NMR (CDCl$_3$, δ): 2.95–3.25 (3H, m), 5.20–5.43 (4H, m), 5.82–6.00 (2H, m).

EXAMPLE 16-1)

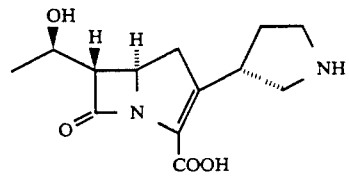

(5R,6S)-6-[(1R)-1-Hydroxyethyl]-7-oxo-3-[(3S)pyrrolidin-3-yl]-1-azabicyclo[3.2.0]hept-2-ene-2-carboxylic acid was obtained in 91.0% yield in substantially the same manner as that of Example 9.

IR (Nujol): 1750 cm$^{-1}$.

NMR (D$_2$O, δ): 1.29 (3H, d, J=6 Hz), 1.80–2.23 (2H, m), 4.00–4.40 (2H, m).

EXAMPLE 16-2)

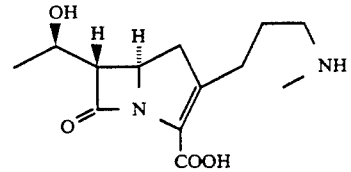

(5R,6S)-6-[(1R)-1-Hydroxyethyl]-7-oxo-3-[(3R)-pyrrolidin-3-yl]-1-azabicyclo[3.2.0]hept-2-ene-2-carboxylic acid was obtained in 93.0% yield in substantially the same manner as that of Example 9.

IR (Nujol): 1750 cm$^{-1}$.

NMR (D$_2$O, δ): 1.28 (3H, d, J=6 Hz), 1.98–2.22 (2H, m).

EXAMPLE 16-3)

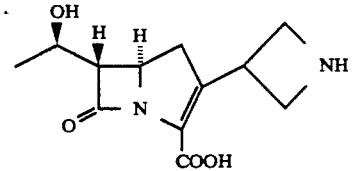

(5R,6S)-3-(Azetidin-3-yl)-6-[(1R)-1-hydroxyethyl]-7-oxo-1-azabicyclo[3.2.0]hept-2-ene-2-carboxylic acid was obtained in 78.3% yield in substantially the same manner as that of Example 9.

IR (Nujol): 1750 cm$^{-1}$.

NMR (D$_2$O, δ): 1.28 (3H, d, J=6 Hz).

EXAMPLE 17-1)

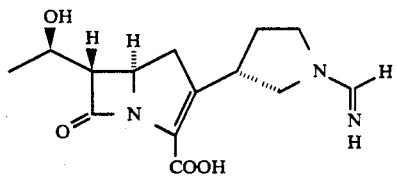

(5R,6S)-3-[(3S)-1-Formimidoylpyrrolidin-3-yl]-6-[(1R)-1-hydroxyethyl]-7-oxo-1-azabicyclo[3.2.0]hept-2-ene-2-carboxylic acid was obtained in 56.0% yield in substantially the same manner as that of Example 12.

IR (Nujol): 1750, 1710 cm$^{-1}$.

NMR (D$_2$O, δ): 1.27 (3H, d, J=6 Hz), 1.80–2.37 2H, m), 2.69–3.01 (2H, m), 7.90 (1H, br s).

EXAMPLE 17-2)

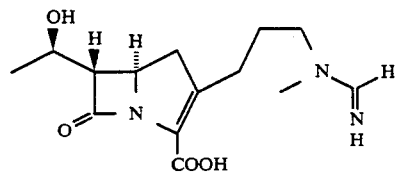

(5R,6S)-3-[(3R)-1-Formimidoylpyrrolidin-3-yl]-6-[(1R)-1-hydroxyethyl]-7-oxo-1-azabicyclo[3.2.0-hept-2-ene-2-carboxylic acid was obtained in 43.0% yield in substantially the same manner as that of Example 12.

IR (Nujol): 1750, 1710 cm$^{-1}$.

NMR (D$_2$O, δ): 1.27 (3H, d, J=6 Hz), 1.80–2.35 (2H, m), 2.72–3.00 (2H, m), 7.89 (1H, br s).

EXAMPLE 17-3)

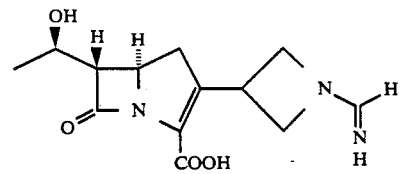

(5R,6S)-3-(1-Formimidoylazetidin-3-yl)-6-[(1R)-1-hydroxyethyl]-7-oxo-1-azabicyclo[3.2.0]hept-2-ene-2-carboxylic acid was obtained in 23.5% yield in substantially the same manner as that of Example 12.

IR (Nujol): 1750, 1710 cm$^{-1}$.

NMR (D$_2$O, δ): 1.28 (3H, d, J=6 Hz), 3.10 (2H, d, J=9 Hz), 3.30–3.50 (1H, m), 7.69 (1H, br s).

EXAMPLE 18

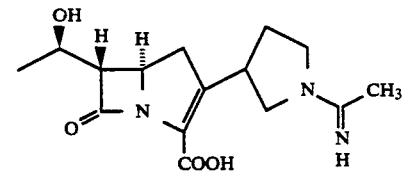

A solution of (5R,6S)-6-[(1R)-1-hydroxyethyl]-7-oxo-3-(pyrrolidin-3-yl)-1-azabicyclo[3.2.0]hept-2-ene-2-carboxylic acid (180 mg) in phosphate buffer solution (pH was adjusted to around pH 8.5 with 30% aqueous potassium carbonate at 0° C. To the solution was added four portions of ethyl acetimidate hydrochloride (835 mg), while adjusting pH to around 8.5 with j0% aqueous potassium carbonate. After stirring for 10 minutes at 0° C., the solution was adjusted to around pH 7.0 with 1N hydrochloric acid. After the mixture was washed with a mixture of ethyl acetate (270 ml) and tetrahydrofuran (30 ml), the aqueous layer was concentrated. The resulting solution was chromatographed on nonionic adsorption resin "Diaion HP-20" (40 ml) eluting with a mixture of acetonitrile and water (2:98, V/V). The fractions containing the object compound were collected and freeze-dried to give (5R,6S)-3-(1-acetimidoylpyrrolidin-3-yl)-6-[(1R)-1-hydroxyethyl]-7-oxo-1-azabicyclo[3.2.0-]hept-2-ene-2-carboxylic acid (80 mg).

IR (Nujol): 3350, 1760 cm$^{-1}$.

NMR (D$_2$O, δ): 1.27 (3H, d, J=7.2 Hz), 1.8–2.3 (2H, m), 2.25 (3H, s), 2.90 (2H, d-like, J=9.0 Hz), 3.3–4.2 (8H, m).

EXAMPLE 19-1)

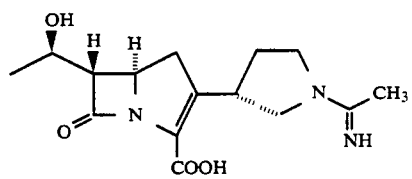

To a solution of (5R,6S)-6-[(1R)-1-hydroxyethyl]-7-oxo-3-[(3S)-pyrrolidin-3-yl]-1-azabicyclo[3.2.0]hept-2-ene-2-carboxylic acid (1.0 g) in water (30 ml) was added ethyl acetimidate hydrochloride (2.8 g) at 0° C while adjusting pH to 8.5 with 30% sodium hydroxide solution. After stirring for 30 minutes at the same temperature, the solution was adjusted to pH 6.5 with 1N-hydrochloric.acid, washed with ethyl acetate, and then concentrated in vacuo. The residue was chromatographed on nonionic adsorption resin "Diaion HP-20" eluting with aqueous isopropyl alcohol (3%). The farctions containing the desired compound were collected and lyophilized to give (5R,6S)-3-[(3S)-1-acetimidoyl-pyrrolidin-3-yl]-6-[(1R)-1-hydroxyethyl]-7-oxo-1-azabicyclo[3.2.0]hept-2-ene-2-carboxylic acid (550 mg).

IR (Nujol): 1750 cm$^{-1}$.

NMR (D$_2$O, δ): 1.28 (3H, d, J=6 Hz), 2.27 (3H, s), 1.8–2.4 (2H, m), 2.78–3.07 (2H, m).

EXAMPLE 19-2)

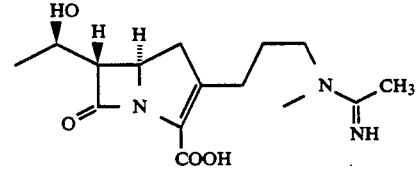

(5R,6S)-3-[(3R)-1-Acetimidoylpyrrolidin-3-yl]-6-[(1R)-hydroxyethyl]-7-oxo-1-azabicyclo[3.2.0]hept-2-ene-2-carboxylic acid was obtained in 22.5% yield in substantially the same manner as that of Example 19-1).

IR (Nujol): 1750 cm$^{-1}$.

NMR (D$_2$O, δ): 1.28 (3H, d, J=6 Hz), 2.27 (3H, s), 1.70–2.42 (2H, m), 2.75–3.05 (2H, m).

EXAMPLE 19-3)

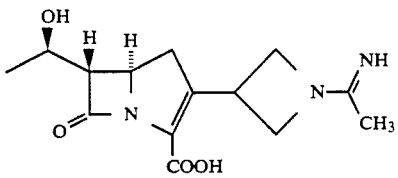

(5R,6S)-3-(1-Acetimidoylazetidin-3-yl)-6-[(1R)-1-hydroxyethyl]-7-oxo-1-azabicyclo[3.2.0]hept-2-ene-2-carboxylic acid was obtained in 29.5% yield in substantially the same manner as that of Example 19-1).

IR (Nujol): 1750 cm$^{-1}$.

NMR (D$_2$O, δ): 1.28 (3H, d, J=6 Hz), 2.08 (3H, s), 3.02–3.22 (2H, m).

EXAMPLE 20-1)

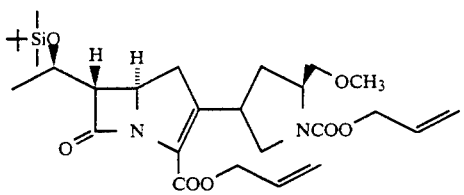

Allyl (5R,6S)-3-[(2S)-1-allyloxycarbonyl-2-methoxymethylpyrrolidin-4-yl]-6-[(1R)-1-tert-butyldimethylsilyloxyethyl]-7-oxo-1-azabicyclo[3.2.0]hept-2-ene-2-carboxylate was obtained in 62.8% yield in substantially the same manner as that of Example 6.

IR (Nujol): 1710, 1780 cm$^{-1}$.

NMR (CDCl$_3$, δ): 0.07 (6H, s), 0.88 (9H, s), 1.24 (3H, d, J=7 Hz), 3.33 (3H, s), 4.08–4.40 (4H, m), 4.59–4.83 (4H, m), 5.19–5.47 (4H, m), 5.87–6.04 (2H, m).

EXAMPLE 20-2)

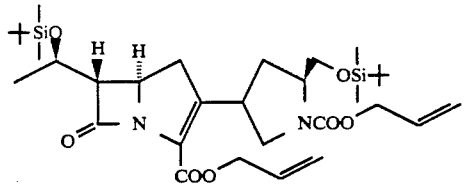

Allyl (5R,6S)-3-[(2S)-1-allyloxycarbonyl-2-tert-butyldimethylsilyloxymethylpyrrolidin-4-yl]-6-[(1R)-1-tert-butyldimethylsilyloxyethyl]-7-oxo-1-azabicyclo[3.2.0]hept-2-ene-2-carboxylate was obtained in 62.8% yield in substantially the same manner as that of Example 6.

IR (Nujol): 1710, 1750, 1790 cm$^{-1}$.

NMR (CDCl$_3$, δ): 0.08 (12H, s), 0.88 (18H, s), 1.23 (3H, d, J=7 Hz), 1.90–2.22 (2H, m), 2.72–4.24 (11H, m), 4.50–4.70 (4H, m), 5.11–5.47 (4H, m), 5.68–6.03 (2H, m).

EXAMPLE 20-3)

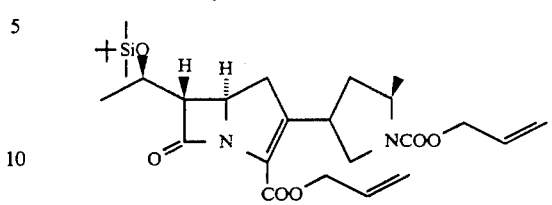

Allyl (5R,6S)-3-[(2R)-1-allyloxycarbonyl-2-methylpyrrolidin-4-yl]-6-[(1R)-1-tert-butyldimethylsilyloxyethyl]-7-oxo-1-azabicyclo[3.2.0]hept-2-ene-2-carboxylate was obtained in 72.3% yield in substantially the same manner as that of Example 6.

IR (Nujol): 1710, 1780 cm$^{-1}$.

NMR (CDCl$_3$, δ): 0.07 (6H, s), 0.88 (9H, s), 1.24 (6H, d, J=7 Hz), 4.50–4.82 (4H, m), 5.17–5.50 (4H, m), 5.87–6.03 (2H, m).

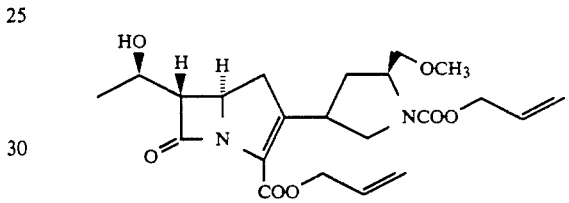

Allyl (5R,6S)-3-[(2S)-1-allyloxycarbonyl-2-methoxymethylpyrrolidin-4-yl]-6-[(1R)-1-hydroxyethyl]-7-oxo-1-azabicyclo[3.2.0]hept-2-ene-2-carboxylate was obtained in 64.3% yield in substantially the same manner as that of Example 7.

IR (Nujol): 1705, 1780 cm$^{-1}$.

NMR (CDCl$_3$, δ): 1.26 (3H, m), 3.33 (3H, s), 4.50–4.80 (4H, m), 5.21–5.36 (4H, m), 5.84–6.02 (2H, m).

EXAMPLE 21-2)

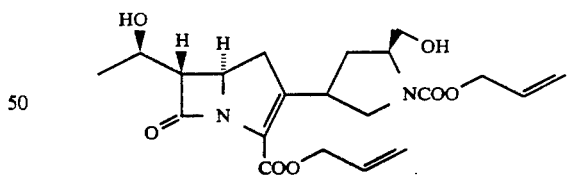

Allyl (5R,6S)-3-[(2S)-1-allyloxycarbonyl-2-hydroxymethylpyrrolidin-4-yl]-6-[(1R)-1-hydroxyethyl]-7-oxo-1-azabicyclo[3.2.0]hept-2-ene-2-carboxylate was obtained in 52.6% yield from allyl (5R,6S)-3-[(2S)-1-allyloxycarbonyl-2-tert-butyldimethylsilyloxymethylpyrrolidin-4-yl]-6-[(1R)-1-tert-butyldimethylsilyloxyethyl]-7-oxo-1-azabicyclo[3.2.0]hept-2-ene-2-carboxylate in substantially the same manner as that of Example 7.

IR (Nujol): 1695, 1770, 3400 cm$^{-1}$.

NMR (CDCl$_3$, δ): 1.28 (3H, d, J=7 Hz), 1.50–1.73 (2H, m), 4.52–4.73 (4H, m), 5.16–5.45 (4H, m), 5.70–6.12 (2H, m).

EXAMPLE 31-3)

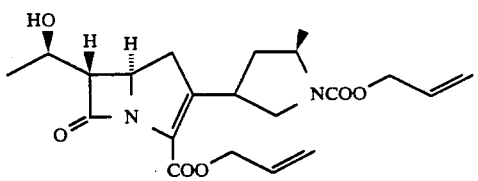

Allyl (5R,6S)-3-[(2R)-1-allyloxycarbonyl-2-methylpyrrolidin-4-yl]-6-[(1R)-1-hydroxyethyl]-7-oxo-1-azabicyclo[3.2.0]hept-2-ene-2-carboxylate was obtained in 93.6% yield in substantially the same manner as that of Example 7.

IR (Nujol): 1700, 1785, 3400 cm$^{-1}$.
NMR (CDCl$_3$, δ): 1.20–1.40 (6H, m), 4.58–4.78 (4H, m), 5.17–5.35 (4H, m), 5.82–6.05 (2H, m).

EXAMPLE 22-1)

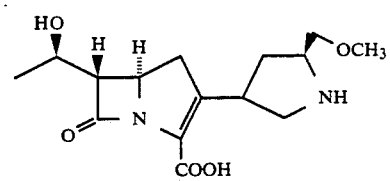

(5R,6S)-6-[(1R)-1-Hyrdoxyethyl]-3-[(2S)-2-methoxymethylpyrrolidin-4-yl]-7-oxo-1-azabicyclo[3.2.0]hept-2-ene-2-carboxylic acid was obtained in 98.0% yield in substantially the same manner as that of Example 9.

IR (Nujol): 1750 cm$^{-1}$.
NMR (D$_2$O, δ): 1.20–1.27 (3H, m), 1.91–2.13 (2H, m), 3.35 (3H, s).

EXAMPLE 22-2)

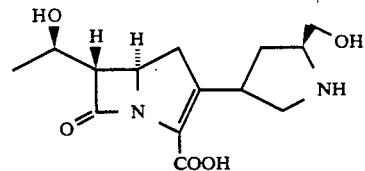

(5R,6S)-6-[[1R)-1-Hydroxyethyl]-3-[(2S)-2-hydroxymethylpyrrolidin-4-yl]-7-oxo-1-azabicyclo[3.2.0]hept-2-ene-2-carboxylic acid was obtained in 72.3% yield in substantially the same manner as that of Example 9.

IR (Nujol): 1750 cm$^{-1}$.
NMR (D$_2$O, δ): 1.24 (3H, d, J=7 Hz), 1.60–2.31 (2H, m), 2.87–4.28 (11H, m).

EXAMPLE 22-3)

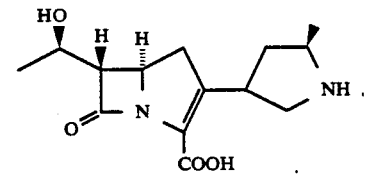

(5R,6S)-6-[(1R)-1-Hydroxyethyl]-3-[(2R)-2-methylpyrrolidin-4-yl]-7-oxo-1-azabicyclo[3.2.0]hept-2-ene-2-carboxylic acid was obtained in 64.4% yield in substantially the same manner as that of Example 9.

IR (Nujol): 1760 cm$^{-1}$.
D$_2$O, δ): 1.21 (3H, d, J=7 Hz), 1.33 (3H, d, J=7 Hz).

EXAMPLE 23-1)

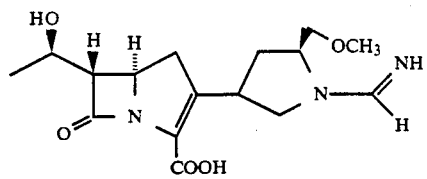

(5R,6S)-3-[(2S)-1-Formimidoyl-2-methoxymethylpyrrolidin-4-yl]-6-[(1R)-1-hydroxyethyl]-7-oxo-1-azabicyclo[3.2.0]hept-2-ene-2-carboxylic acid was obtained in 11% yield in substantially the same manner as that of Example 12.

IR (Nujol): 1750 cm$^{-1}$.
NMR (D$_2$O, δ): 1.24 (3H, d, J=7 Hz), 1.94–2.10 (2H, m), 3.36 (3H, s), 7.78–7.93 (1H, m).

EXAMPLE 23-2)

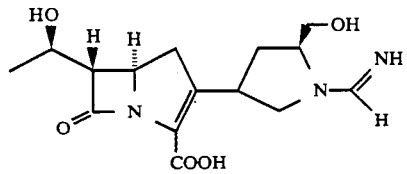

(5R,6S)-3-[(2S)-1-Formimidoyl-2-hydroxymethylpyrrolidin-4-yl]-6-[(1R)-1-hydroxyethyl]-7-oxo-1-azabicyclo[3.2.0]hept-2-ene-2-carboxylic acid was obtained yield in substantially the same manner as that of Example 12.

IR (Nujol): 1750 cm$^{-1}$.
NMR (D$_2$O, δ): 1.24 (3H, d, J=7 Hz), 7.97 (1H, br s).

EXAMPLE 23-3)

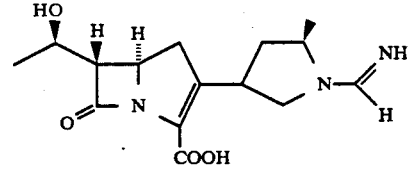

(5R,6S)-3-[(2R)-1-Formimidoyl-2-methylpyrrolidin-4-yl]-6-[(1R)-1-hydroxyethyl]-7-oxo-1-azabicyclo[3.2.0-]hept-2-ene-2-carboxylic acid was obtained in 47.9% yield in substantially the same manner as that of Example 12.

IR (Nujol): 1755 cm$^{-1}$.
NMR (D$_2$O, δ): 1.24 (6H, d, J=7 Hz), 7.76–7.93 (1H, m).

The following compounds were obtained in substantially the same manner as that of Example 4.

EXAMPLE 24-1)

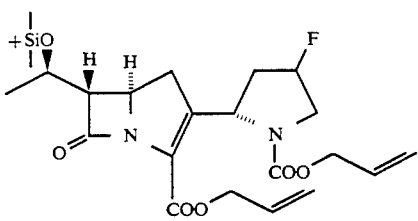

Allyl (5R,6S)-3-[(2S)-1-allyloxycarbonyl-4-fluoropyrrolidin-2-yl]-6-[(1R)-1-t-butyldimethylsilyloxyethyl]-7-oxo-1-azabicyclo[3.2.0]hept-2-ene-2-carboxylate.

IR (CH$_2$Cl$_2$): 1770, 1700 cm$^{-1}$.

NMR (CDCl$_3$, δ): 0.06 (6H, s), 0.90 (9H, s), 2.7–3.2 (3H, m), 4.3–4.8 (4H, m), 5.0–5.6 (5H, m), 5.8–6.1 (2H, m).

EXAMPLE 24-2)

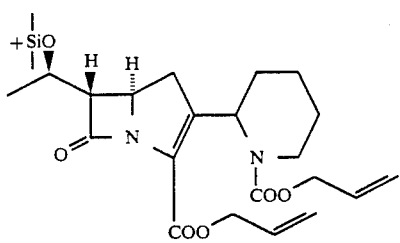

Allyl (5R,6S)-3-(1-allyloxycarbonylpiperidin-2-yl)-6-[(1R)-1-t-butyldimethylsilyloxyethyl]-7-oxo-1-azabicyclo[3.2.0]hept-2-ene-2-carboxylate.

IR (Neat): 1780, 1700 cm$^{-1}$.

NMR (CDCl$_3$, δ): 0.03 (6H, s), 0.90 (9H, s), 2.5–3.0 (3H, m), 4.5–4.8 (4H, m), 5.1–5.4 (4H, m), 5.8–6.1 (2H, m).

EXAMPLE 24-3)

(Isomer A)

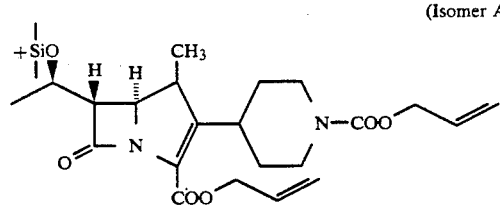

Isomer A of allyl (5R,6S)-3-(1-allyloxycarbonylpiperidin-4-yl)-6-[(1R)-1-t-butyldimethylsilyloxyethyl]-4-methyl-7-oxo-1-azabicyclo[3.2.0]hept-2-ene-2-carboxylate (from Isomer A of (3S,4R)-4-[2-(1-allyloxycarbonylpiperidin-4-yl)-1-methyl-2-oxoethyl]-3-[(1R)-1-t-butyldimethylsilyloxyethyl]-2-oxoazetidine).

IR (Neat): 1780, 1700 cm$^{-1}$.

NMR (CDCl$_3$, δ): 0.06 (3H, s), 0.92 (9H, s), 1.2–1.4 (6H, m), 1.5–1.8 (4H, m), 4.5–5.0 (4H, m), 5.1–5.6 (4H, m), 5.8–6.0 (2H, m).

EXAMPLE 24-4)

(Isomer B)

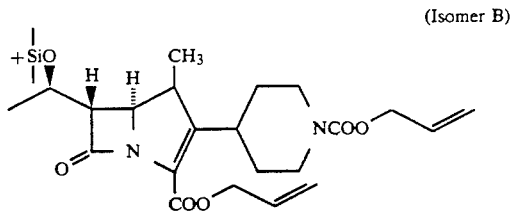

Isomer B of allyl (5R,6S)-3-(1-allyloxycarbonylpiperidin-4-yl)-6-[(1R)-1-t-butyldimethylsilyloxyethyl]-4-methyl-7-oxo-1-azabicyclo[3.2.0]hept-2-ene-2-carboxylate (from Isomer B of (3S,4R)-4-[2-(1-allyloxycarbonylpiperidin-4-yl)-1-methyl-2-oxoethyl]-3-[(1R)-1-t-butyldimethylsilyloxyethyl]-2-oxoazetidine).

IR (Neat): 1780, 1700 cm$^{-1}$.

NMR (CDCl$_3$, δ): 0.06 (3H, s), 0.90 (9H, s), 4.5–4.9 (4H, m), 5.2–5.6 (4H, m), 5.8–6.0 (2H, m).

The following compounds were obtained in substantially the same manner as that of Example 6.

EXAMPLE 24-5)

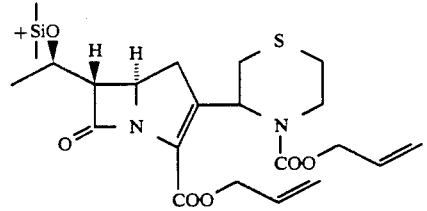

Allyl (5R,6S)-3-[4-(allyloxycarbonyl)thiomorpholin-3-yl]-6-[(1R)-1-tert-butyldimethylsilyloxyethyl]-7-oxo-1-azabicyclo[3.2.0]hept-2-ene-2-carboxylate.

IR (Neat): 1780, 1710–1700 cm$^{-1}$.

EXAMPLE 24-6)

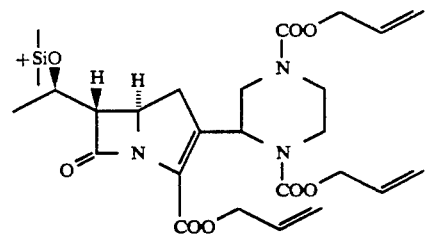

Allyl (5R,6S)-3-[1,4-bis(allyloxycarbonyl)piperazin-2-yl]-6-[(1R)-1-tert-butyldimethylsilyloxyethyl]-7-oxo-1-azabicyclo[3.2.0]hept-2-ene-2-carboxylate.

IR (Neat): 1780, 1720–1690 cm$^{-1}$.

EXAMPLE 24-7)

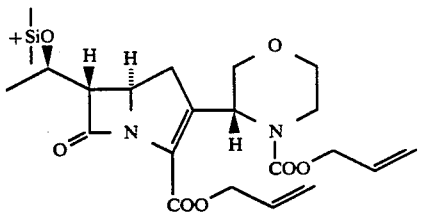

Allyl (5R,6S)-3-[(3R)-4-allyloxycarbonylmorpholin-3-yl]-6-[(1R)-1-tert-butyldimethylsilyloxyethyl]-7-oxo-1-azabicyclo[3.2.0]hept-2-ene-2-carboxylate.
IR (Neat): 1785, 1705 cm$^{-1}$.
NMR (CDCl$_3$, δ): 0.08 (6H, s), 0.89 (9H, s).

EXAMPLE 24-8)

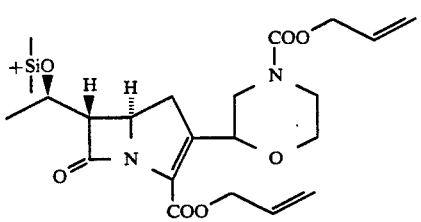

Allyl (5R,6S)-3-[4-allyloxycarbonylmorpholin-2-yl]-6-[(1R)-1-tert-butyldimethylsilyloxyethyl]-7-oxo-1-azabicyclo[3.2.0]hept-2-ene-2-carboxylate.
IR (Neat): 1780, 1710–1700 cm$^{-1}$.

EXAMPLE 24-9)

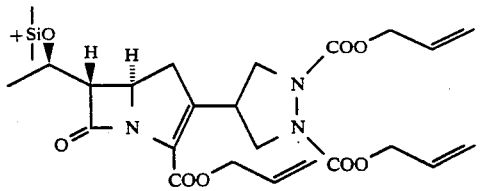

Allyl (5R,6S)-3-[1,2-bis(allyloxycarbonylpyrazolidin-4-yl]-6-[(1R)-1-tert-butyldimethylsilyloxyethyl]-7-oxo-1-azabicyclo[3.2.0]hept-2-ene-2-carboxylate.
IR (Nujol): 1710, 1780 cm$^{-1}$.
NMR (CDCl$_3$, δ): 0.08 (6H, s), 0.88 (9H, s), 1.23 (3H, d, J=6 Hz), 2.73–2.80 (2H, m), 3.06–3.11 (2H, m), 3.50–3.92 (2H, m), 4.04–4.62 (4H, m), 4.58–4.81 (6H, m), 5.20–5.47 (6H, m), 5.80–6.02 (3H, m).

EXAMPLE 24-10)

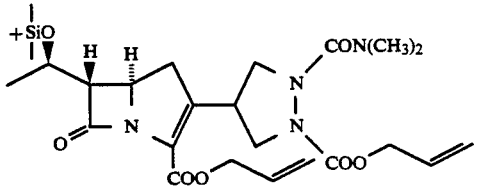

Allyl (5R,6S)-3-[2-allyloxycarbonyl-1-(dimethylcarbamoyl)pyrazolidin-4-yl]-6[(1R)-1-tert-butyldimethylsilyloxyethyl]-7-oxo-1-azabicyclo[3.2.0]hept-2-ene-2-carboxylate.
IR (Nujol): 1695, 1775 cm$^{-1}$.
NMR (CDCl$_3$, δ): 0.07 (6H, s), 0.88 (9H, s), 1.25 (3H, d, J=6 Hz), 2.99 (6H, s), 4.61–4.78 (4H, m), 5.19–5.48 (4H, m), 5.83–6.05 (2H, m).

EXAMPLE 24-11)

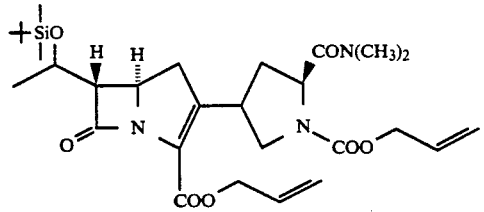

Allyl (5R,6S)-3-[(2S)-1-allyloxycarbonyl-2-dimethylcarbamoylpyrrolidin-4-yl]-6-[(1R)-1-tert-butyldimethylsilyloxyethyl]-7-oxo-1-azabicyclo[3.2.0]hept-2-ene-2-carboxylate.
IR (Nujol): 1655, 1710, 1780 cm$^{-1}$.
NMR (CDCl$_3$, δ): 0.08 (6H, s), 0.87 (9H, s), 1.23 (3H, d, J=7 Hz), 2.04–2.10 (2H, m), 2.98 (3H, s), 3.08 (3H, s), 4.57–4.82 (5H, m), 5.19–5.50 (4H, m), 5.80–6.05 (2H, m).

The following compounds were obtained in substantially the same manner as that of Example 4.

EXAMPLE 24-12)

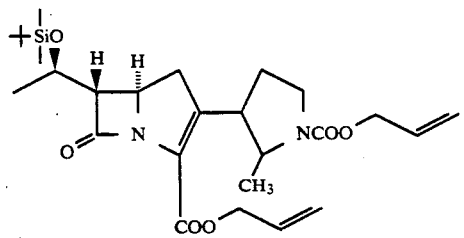

Allyl (5R,6S)-3-(1-allyloxycarbonyl-2-methylpyrrolidin-3-yl)-6-[(1R)-1-t-butyldimethylsilyloxyethyl]-7-oxo-1-azabicyclo[3.2.0]hept-2-ene-2-carboxylate.
IR (Neat): 1775, 1705 cm$^{-1}$.
NMR (CDCl$_3$, δ): 0.08 (6H, s), 0.91 (9H, s), 1.1–1.4 (6H, m), 2.76–2.83 (2H, m), 3.06–3.10 (1H, m), 4.5–4.8 (4H, m), 5.2–4.4 (4H, m), 5.8–6.0 (2H, m).

EXAMPLE 24-13)

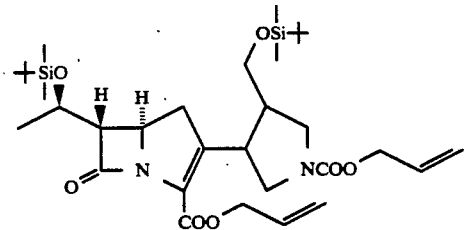

Allyl (5R,6S)-3-[1-allyloxycarbonyl-(4-t-butyldimethylsilyloxymethyl)pyrrolidin-3-yl]-6-[(1R)-1-t-butyldimethylsilyloxyethyl]-7-oxo-1-azabicyclo[3.2.0]hept-2-ene-2-carboxylate.
IR (Neat): 1780, 1705 cm$^{-1}$.

NMR (CDCl$_3$, δ): 0.090, 0.075 (6H, each s), 0.88, 0.91 (9H, each s), 1.22 (3H, d, J=7 Hz), 2.8–3.4 (5H, m), 3.5–3.8 (4H, m), 4.5–4.9 (4H, m), 5.2–5.6 (4H, m), 5.8–6.0 (2H, m).

EXAMPLE 24-14)

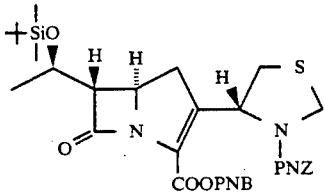

4-Nitrobenzyl (5R,6S)-6-[(1R)-1-tert-butyldimethyl-silyloxyethyl]-3-[(4R)-3-(4-nitrobenzyloxycarbonyl)-thiazolidin-4-yl]-7-oxo-1-azabicyclo[3.2.0]hept-2-ene-2-carboxylate was obtained in 44.0% yield in substantially the same manner as that of Example 6.

IR (Neat): 1775, 1720, 1705 cm$^{-1}$.

The following compounds were obtained in substantially the same manner as that of Example 7.

EXAMPLE 25-1)

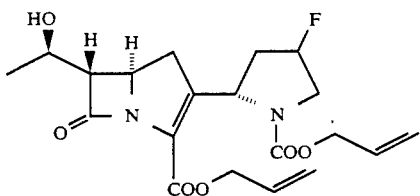

Allyl (5R,6S)-3-[(2S)-1-allyloxycarbonyl-4-fluoropyrrolidin-2-yl]-6-[(1R)-1-hydroxyethyl]-7-oxo-1azabicyclo[3.2.0]hept-2-ene-2-carboxylate.

IR (Neat): 3350, 1770, 1700 cm$^{-1}$.

NMR (CDCl$_3$, δ): 2.7–3.2 (3H, m), 4.4–4.8 (4H, m), 5.0–5.6 (5H, m), 5.8–6.1 (2H, m).

EXAMPLE 25-2)

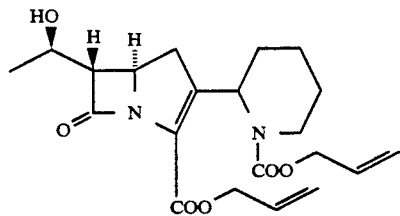

Allyl (5R,6S)-3-(1-allyloxycarbonylpiperidin-2-yl)-6-[(1R)-1-hydroxyethyl]-7-oxo-1-azabicyclo[3.2.0]hept-2-ene-2-carboxylate.

IR (CH$_2$Cl$_2$): 3400, 1780, 1700 cm$^{-1}$.

NMR (CDCl$_3$, δ): 2.7–3.3 (3H, m), 4.5–4.9 (4H, m), 5.1–5.4 (4H, m), 5.8–6.1 (2H, m).

EXAMPLE 25-3)

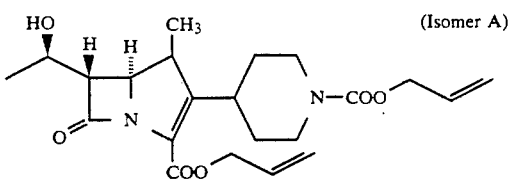
(Isomer A)

Isomer A of allyl (5R,6S)-3-(1-allyloxycarbonyl-piperidin-4-yl)-6-[(1R)-1-hydroxyethyl]-4-methyl-7-oxo-1-azabicyclo[3.2.0]hept-2-ene-2-carboxylate (from Isomer A of allyl (5R,6S)-3-(1-allyloxycarbonylpiperidin-4-yl)-6-[(1R)-1-t-butyldimethylsilyloxyethyl]-4-methyl-7-oxo-1-azabicyclo[3.2.0]hept-2-ene-2-carboxylate.

IR (Neat): 1760, 1700 cm$^{-1}$.

EXAMPLE 25-4)

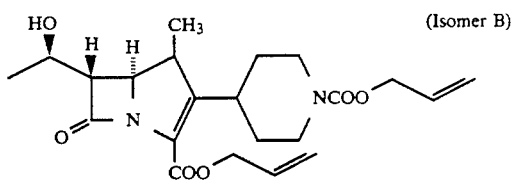
(Isomer B)

Isomer B of allyl (5R,6S)-3-(1-allyloxycarbonyl-piperidin-4-yl)-6-[(1R)-1-hydroxyethyl]-4-methyl-7-oxo-1-azabicyclo[3.2.0]hept-2ene-2-carboxylate (from Isomer B of allyl (5R,6S)-3-(1-allyloxycarbonylpiperidin-4-yl)-6-[(1R)-1-t-butyldimethylsilyloxyethyl]-4-methyl-7-oxo-1-azabicyclo[3.2.0]hept-2-ene-2-carboxylate.

IR (Neat): 1760, 1680 cm$^{-1}$.

NMR (CDCl$_3$, δ): 2.8–3.0 (2H, m), 3.0–3.6 (2H, m), 4.5–4.9 (4H, m), 5.2–5.5 (4H, m), 5.8–6.1 (2H, m).

EXAMPLE 25-5)

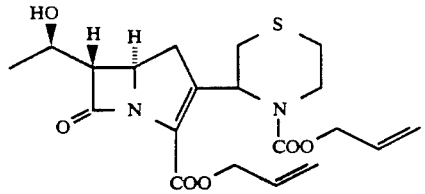

Allyl (5R,6S)-3-[4-(allyloxycarbonyl)thiomorpholin-3-yl]-6-[(1R)-1-hydroxyethyl]-7-oxo-1-azabicyclo[3.2.0-]hept-2-ene-2-carboxylate.

IR (Neat): 3500–3350, 1780, 1710–1690 cm$^{-1}$.

EXAMPLE 25-6)

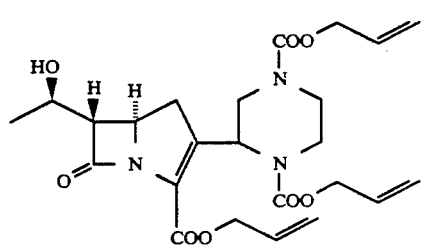

Allyl (5R,6S)-3-[1,4-bis(allyloxycarbonyl)piperazin-2-yl]-6-[(1R)-1-hydroxyethyl]-7-oxo-1-azabicyclo[3.2.0-]hept-2-ene-2-carboxylate.

IR (Neat): 3500–3400, 1775, 1710–1690 cm⁻¹.

EXAMPLE 25-7)

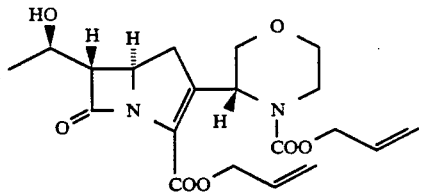

Allyl (5R,6S)-3-[(3R)-4-allyloxycarbonylmorpholin-3-yl]-6-]-(1R)-1-hydroxyethyl]-7-oxo-1-azabicyclo[3.2.0-hept-2-ene-2-carboxylate.

IR (Neat): 3500–3350, 1780, 1705 cm⁻¹.

EXAMPLE 25-8)

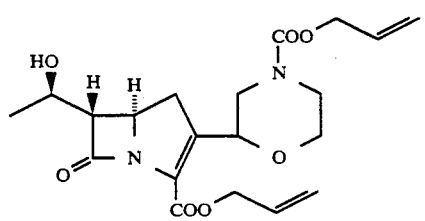

Allyl (5R,6S)-3-[4-allyloxycarbonylmorpholin-2-yl]-6-[(1R)-1-hydroxyethyl]-7-oxo-1-azabicyclo[3.2.0]hept-2-ene-2-carboxylate.

IR (Neat): 3400–3200, 1775, 1710–1690 cm⁻¹.

EXAMPLE 25-9)

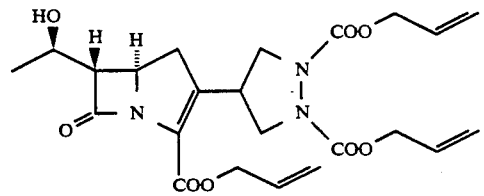

Allyl (5R,6S)-3-[1,2-bis(allyloxycarbonyl)pyrazolidin-4-yl]-6-[(1R)-1-hydroxyethyl]-7-oxo-1-azabicyclo[3.2.0]hept-2-ene-2-carboxylate.

IR (Nujol): 1710, 1780, 3450 cm⁻¹.

CDCl₃, δ): 1.24 (3H, d, J=6 Hz), 2.74–2.86 (2H, m), 3.06–3.18 (2H, m), 3.50–3.90 (2H, m), 4.06–4.50 (4H, m), 4.60–4.80 (6H, m), 5.20–5.50 (6H, m), 5.80–6.00 (3H, m).

EXAMPLE 25-10)

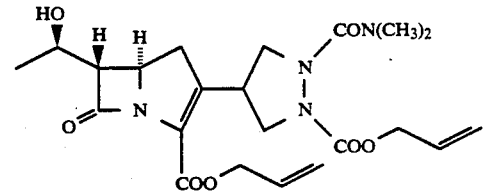

Allyl (5R,6S)-3-[2-allyloxycarbonyl-1-(dimethylcarbamoyl)pyrazolidin-4-yl]-6-[(1R)-1-hydroxyethyl]-7-oxo-1-azabicyclo[3.2.0]hept-2-ene-2-carboxylate.

IR (Nujol): 1690, 1770 cm⁻¹.

NMR (CDCl₃, δ): 1.33 (3H, d, J=6 Hz), 2.84–2.95 (2H, m), 3.00 (6H, s), 3.12–3.31 (2H, m), 3.44–3.73 (2H, m), 3.80–3.98 (1H, m), 4.10–4.47 (3H, m), 4.61–4.87 (4H, m), 5.20–5.47 (4H, m), 5.82–6.07 (2H, m).

EXAMPLE 25-11)

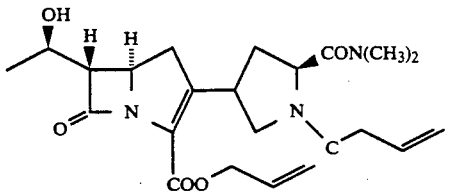

Allyl (5R,6S)-3-[(2S)-1-allyloxycarbonyl-2-dimethylcarbamoylpyrrolidin-4-yl]-6-[(1R)-1-hydroxyethyl]-7-oxo-1-azabicyclo[3.2.0]hept-2-ene-2-carboxylate.

IR (Nujol): 1640, 1700, 1775, 3350–3400 cm⁻¹.

NMR (CDCl₃, δ): 1.34 (3H, d, J=7 Hz), 2.05–2.10 (3H, m), 2.98 (3H, s), 3.09 (3H, s), 2.87–3.15 (2H, m), 3.30–3.50 (1H, m), 3.82–3.94 (1H, m), 4.08–4.40 (4H, m), 4.56–4.82 (5H, m), 5.15–5.50 (4H, m), 5.84–6.72 (2H m).

EXAMPLE 25-12)

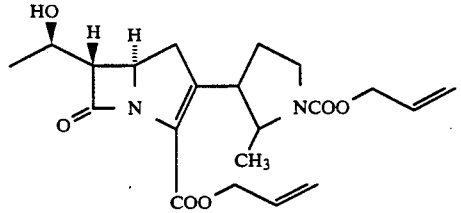

Allyl (5R,6S)-3-(1-allyloxycarbonyl-2-methylpyrrolidin-3-yl)-6-[(1R)-1-hydroxyethyl]-7-oxo-1-azabicyclo[3.2.0]hept-2-ene-2-carboxylate.

IR (Neat): 3400, 1750, 1680–1700 cm⁻¹.

NMR (D₂O, δ): 1.1–1.4 (6H, m), 2.75–2.90 (2H, m), 3.11–3.20 (1H, m), 4.5–4.9 (4H, m), 5.1–5.5 (4H, m), 5.8–6.8 (2H, m).

EXAMPLE 25-13)

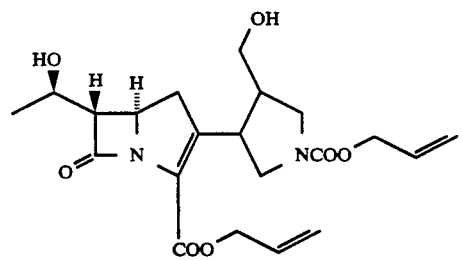

Allyl (5R,6S)-3-[1-allyloxycarbonyl-4-(hydroxymethyl)pyrrolidin-3-yl]-6-[(1R)-1-hydroxyethyl]-7-oxo-1-azabicyclo[3.2.0]hept-2-ene-2-carboxylate.

IR (Neat): 3400, 1770, 1680–1710 cm⁻¹.

NMR (CDCl₃, δ): 1.2–1.4 (3H, m), 4.5–4.9 (4H, m), 5.1–5.5 (4H, m), 5.8–6.0 (2H, m).

EXAMPLE 25-14)

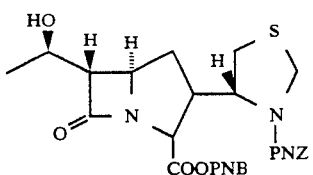

4-Nitrobenzyl (5R,6S)-6-[(1R)-1-hydroxyethyl]-3-[(4R)-3-(4-nitrobenzyloxycarbonyl)thiazolidin-4-yl]-7-oxo-1-azabicyclo[3.2.0]hept-2-ene-2-carboxylate.

IR (CHCl$_3$): 1770, 1720, 1705 cm$^{-1}$.

The following compounds were obtained in substantially the same manner as that of Example 9.

EXAMPLE 26-1)

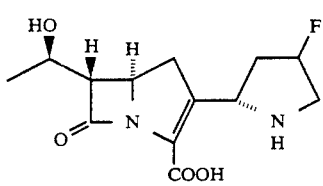

(5R,6S)-3-[(2S)-4-Fluoropyrrolidin-2-yl]-6-[(1R)-1-hydroxyethyl]-7-oxo-1-azabicyclo[3.2.0]hept-2-ene-2-carboxylic acid.

IR (Nujol): 1750 cm$^{-1}$.

D$_2$O, δ): 1.27 (3H, d, J=6 Hz), 3.02 (2H, d, J=9 Hz), 5.1–5.8 (1H, m).

EXAMPLE 26-2)

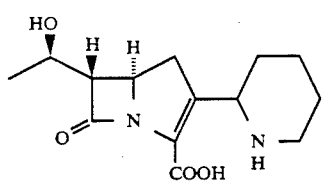

(5R,6S)-6-[(1R)-1-Hydroxyethyl]-7-oxo-3-(piperidin-2-yl)-1-azabicyclo[3.2.0]hept-2-ene-2-carboxylic acid.

IR (Nujol): 1750 cm$^{-1}$.

NMR (D$_2$O, δ): 1.26 (3H, d, J=6 Hz), 1.2–2.1 (6H, m), 3.01 (2H, d, J=9 Hz).

EXAMPLE 26-3)

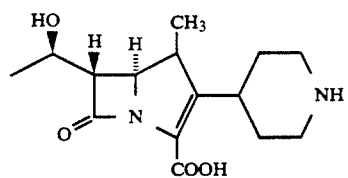

(Isomer A)

Isomer A of (5R,6S)-6-[(1R)-1-hydroxyethyl]-4-methyl-7-oxo-3-(piperidin-4-yl)-1-azabicyclo[3.2.0]hept-2-ene-2-carboxylic acid (from Isomer A of allyl (5R,6S)-3-(1-allyloxycarbonylpiperidin-4--Yl)-6-[(1R)-1-hydroxyethyl]-4-methyl-7-oxo-1-azabicyclo[3.2.0]hept-2-ene-2-carboxylate).

IR (Nujol) 1750 cm$^{-1}$.

NMR (D$_2$O, δ): 1.1–1.4 (6H, m), 1.4–2.2 (5H, m).

EXAMPLE 26-4)

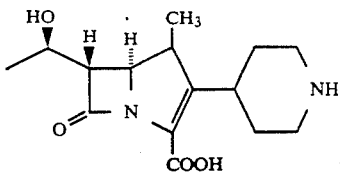

(Isomer B)

Isomer B of (5R,6S)-6-[(1R)-1-hydroxyethyl]-4-methyl-7-oxo-3-(piperidin-4-yl)-1-azabicyclo[3.2.0]hept-2-ene-2-carboxylic acid (from Isomer B of allyl (5R,6S)-3-(1-allyloxycarbonylpiperidin-4-yl)-6-[(1R)-1-hydroxyethyl]-4-methyl-7-oxo-1-azabicyclo[3.2.0]hept-2-ene-2-carboxylate).

IR (Nujol): 1740 cm$^{-1}$.

NMR (D$_2$O, δ): 1.15 (3H, d, J=7 Hz), 1.29 (3H, d, J=6 Hz), 1.7–2.2 (4H, m), 3.0–3.6 (7H, m), 4.0–4.4 (2H, m).

EXAMPLE 26-5)

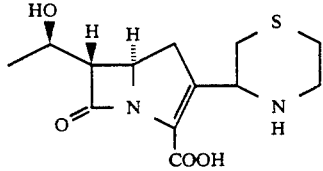

(5R),6S)-6-[(1R)-1-Hydroxyethyl]-3-(thiomorpholin-3-yl)-7-oxo-1-azabicyclo[3.2.0]hept-2-ene-2-carboxylic acid.

IR (KBr): 1760–1750 cm$^{-1}$.

NMR (D$_2$O, δ): 1.27 (3H, d, J=8 Hz). FAB-MS : 299 (M$^+$+1).

EXAMPLE 26-6)

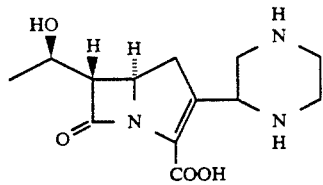

(5R,6S)-6-[(1R)-1-Hydroxyethyl]-3-(piperazin-2-yl)-7-oxo-1-azabicyclo[3.2.0]hept-2-ene-2-carboxylic acid.

IR (EtOH): 1760–1750 cm$^{-1}$.

FAB-MS: 282 (M$^+$+1).

EXAMPLE 26-7)

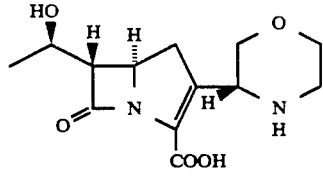

(5R,6S)-6-[(1R)-1-Hydroxyethyl]-3-[(3R)-morpholin-3-yl]-7-oxo-1-azabicyclo[3.2.0]hept-2-ene-2-carboxylic acid.

IR (KBr): 1760–1735 cm$^{-1}$.

NME (D$_2$O, δ): 1.28 (3H, d, J=8 Hz).

EXAMPLE 26-8)

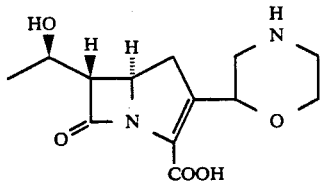

(5R,6S)-6-[(1R)-1-Hydroxyethyl]-3-(morpholin-2-yl)-
-7-oxo-1-azabicyclo[3.2.0]hept-2-ene-2-carboxylic acid.
IR (Nujol): 1760–1750 cm$^{-1}$.
FAB-MS: 283 (M$^+$+1).

EXAMPLE 26-9)

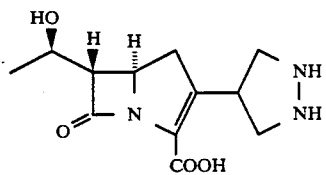

(5R,6S)-6-[(1R)-1-Hydroxyethyl]-3-[pyrazolidin-4-yl)-7-oxo-1-azabicyclo[3.2.0]hept-2-ene-2-carboxylic acid.
IR (Nujol): 1750 cm$^{-1}$.
NMR (D$_2$O, δ): 1.28 (3H, d, J=6 Hz), 2.6–4.35 (14H, m).

EXAMPLE 26-10)

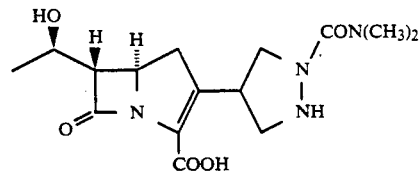

(5R,6S)-3-[1-(Dimethylcarbamoyl)pyrazolidin-4-yl)-6-[(1R)-1-hydroxyethyl]-7-oxo-1-azabicyclo[3.2.0]hept-2-ene-2-carboxylic acid.
IR (Nujol): 1760 cm$^{-1}$.
NMR (D$_2$O, δ): 1.27 (3H, d, J=6 Hz), 2.90 (6H, s).

EXAMPLE 26-11)

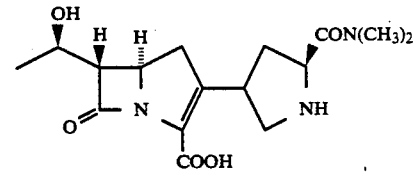

(5R,6S)-3-[(2S)-2-Dimethylcarbamoylpyrrolidin-4-yl]-6-[(1R)-1-hydroxyethyl]-7-oxo-1-azabicyclo[3.2.0-]hept-2-ene-2-carboxylic acid.
IR (Nujol): 1755 cm$^{-1}$.
NMR (D$_2$O, δ): 1.28 (3H, d, J=7 Hz), 2.99 (3H, s), 3.05 (3H, s).

EXAMPLE 26-12)

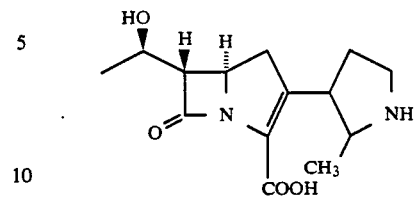

(5R,6S)-6-[(1R)-1-Hydroxyethyl]-3-(2-methylpyrrolidin-3-yl)-7-oxo-1-azabicyclo[3.2.0]hept-2-ene-2-carboxylic acid.
IR (Nujol): 1755 cm$^{-1}$.
NMR (D$_2$O, δ): 1.1–1.4 (6H, m), 1.8–2.4 (2H, m), 2.7–3.0 (2H, m).

EXAMPLE 26-13)

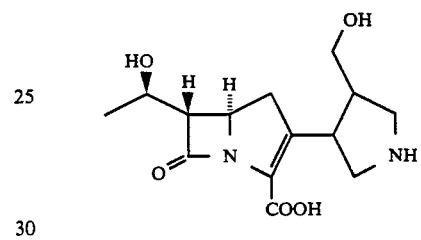

(5R,6S)-6-[(1R)-1-Hydroxyethyl]-3-[4-(hydroxymethyl)pyrrolidin-3-yl]-7-oxo-1-azabicyclo[3.2.0]hept-2-ene-2-carboxylic acid.
IR (Nujol): 1750 cm$^{-1}$.
NMR (D$_2$O, δ): 1.2–1.3 (3H, m), 2.1–2.8 (2H, m).

EXAMPLE 26-14)

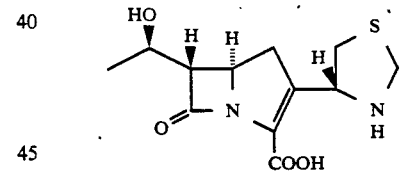

A solution of 4-nitrobenzyl (5R,6S)-6-[(1R)-1-hydroxyethyl]-3-[(4R)-3-(4-nitrobenzyloxycarbonyl)-thiazolidin-4-yl]-7-oxo-1-azabicyclo[3.2.0]hept-2-ene-2-carboxylate (2.00 g) in a mixture of tetrahydrofuran (30 ml) and phosphate buffer (pH 6.5) (30 ml) was hydrogenated under atmospheric pressure of hydrogen over palladium hydroxide on carbon (20%, 0.6 g) for 3 hours at ambient temperature. The catalyst was filtered off and the filtrate was concentrated under reduced pressure to give an aqueous solution. The solution was washed with ethyl acetate, subjected to a column chromatography on silica gel (75 g), and eluted with a mixture of acetonitrile and 75:25, V/V). The fractions containing the object compound were collected and lyophilized to give (5R,6S)-6-[(1R)-1-hydroxyethyl]-3-[(4R)-thiazolidin-4-yl]-7-oxo-1-azabicyclo[3.2.0]hept-2-ene-2-carboxylic acid (0.06 g) as a solid.
IR (Nujol): 1750 cm$^{-1}$.
NMR (D$_2$O, δ): 1.28 (3H, d, J=6.7 Hz)
FAB-MS: 307 (M$^+$+Na).

EXAMPLE 27-1)

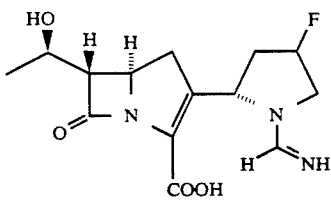

(5R,6S)-3-[(2S)-1-Formimidoyl-4-fluoropyrrolidin-2-yl]-6-[(1R)-1-hydroxyethyl]-7-oxo 1-azabicyclo[3.2.0-]hept-2-ene-2-carboxylic acid was obtained in 20.0% yield in substantially the same manner as that of Example 12.

IR (Nujol): 1750 cm$^{-1}$.

NMR (D$_2$O, δ): 1.27 (3H, d, J=6 Hz), 7.8–8.1 (1H, m).

EXAMPLE 27-2)

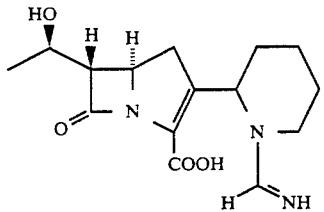

(5R,6S)-3-(1-Formimidoylpiperidin-2-yl)-6-[(1R)-1-hydroxyethyl]-7-oxo-1-azabicyclo[3.2.0]hept-2-ene-2-carboxylic acid was obtained in 53.7% yield in substantially the same manner as that of Example 12.

IR (Nujol): 1755 cm$^{-1}$.

NMR (D$_2$O, δ): 1.26 (3H, d, J=6 Hz), 1.2–2.2 (6H, m), 7.61, 7.72 (1H, each s).

EXAMPLE 27-3)

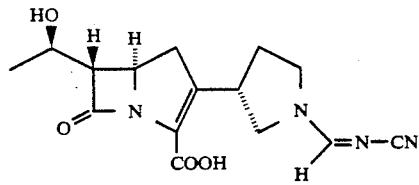

(5R,6S)-3-[(3S)-1-(N-Cyanoformimidoyl)pyrrolidin-3-yl]-6-[(1R)-1-hydroxyethyl]-7-oxo-1-azabicyclo[3.2.0-]hept-2-ene-2-carboxylic acid was obtained in 61.9% yield in substantially the same manner as that of Example 1 2by using ethyl N-cyanoformimidate hydrochloride instead of benzyl formimidate hydrochloride.

IR (Nujol): 1740–1750 cm$^{-1}$.

NMR (D$_2$O, δ): 1.28 (3H, d, J=6 Hz), 1.8–2.6 (2H, m), 2.90 (2H, d, J=7 Hz), 3.4–4.4 (8H, m), 8.34, 8.37 (1H, each s).

EXAMPLE 27-4)

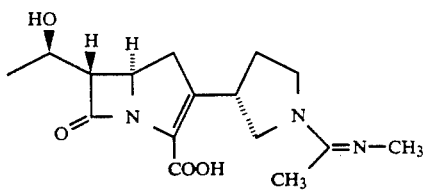

(5R,6S)-6-[(1R)-1-Hydroxyethyl]-3-[(3S)-1-(N-methylacetimidoyl)pyrrolidin-3-yl]-7-oxo-1-azabicyclo[3.2.0]hept-2-ene-2-carboxylic acid was obtained in 14.4% yield in substantially the same manner as that of Example 12 by using ethyl N-methylacetimidate hydrochloride instead.

IR (Nujol): 1740–1750 cm$^{-1}$.

NMR (D$_2$O, δ): 1.25 (3H, d, J=6 Hz), 2.22 (3H, s), 3.01 (3H, s).

EXAMPLE 27-5)

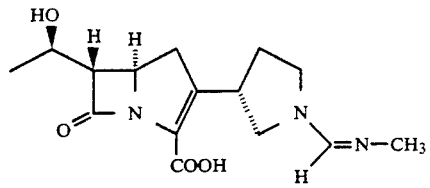

(5R,6S)-6-[(1R)-1-Hydroxyethyl]-3-[(3S)-1-(N-methylformimidoyl)pyrrolidin-3-yl]-7-oxo-1-azabicyclo[3.2.0]hept-2-ene-2carboxylic acid was obtained in 40.7% yield in substantially the same manner as that of Example 27-4).

IR (Nujol): 1750 cm$^{-1}$.

NMR (D$_2$O, δ): 1.25 (3H, d, J=6 Hz), 2.88 (2H, d, J=9 Hz), 3.09 (3H, s), 7.92 (1H, br s).

MS: 308 (M$^+$+1).

EXAMPLE 27-6)

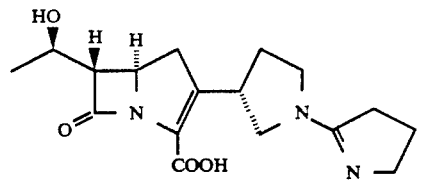

(5R,6S)-6-[(1R)-1-Hydroxyethyl]-7-oxo-3-[(3S)-1-(1-pyrrolin-2-yl)pyrrolidin-3-yl]-1-azabicyclo[3.2.0]hept-2-ene-2-carboxylic acid was obtained in 41.5% yield in substantially the same manner as that of Example 1 2by using 2-methoxy-1-pyrroline instead.

IR (Nujol): 1750 cm$^{-1}$.

NMR (D$_2$O, δ): 1.28 (3H, d, J=6Hz), 1.6–2.4 (4H, m), 2.7–3.1 (4H, m), 3.2–3.8 (7H, m), 3.8–4.3 (3H, m).

MS: 334 (M$^+$+1).

EXAMPLE 27-7)

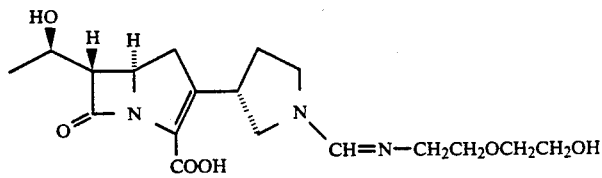

(Isomers A and B)

(5R,6S)-6-[(1R)-1-Hydroxyethyl]-3-[(3S)-1-[N-{2-(2-hydroxyethoxy)ethyl}formimidoyl]pyrrolidin-3-yl]-7-oxo-1-azabicyclo[3.2.0]hept-2-ene-2-carboxylic acid was obtained in substantially the same manner as that of Example 12 by using ethyl N-(hydroxyethoxyethyl)formimidate hydrochloride instead. Two ismers (Isomers A and B) were separated by chromatography on silica gel eluting with 30% water in acetonitrile to give Isomer A (100.0 mg).

IR (Nujol): 1750 cm$^{-1}$.
NMR (D$_2$O, δ): 1.28 (3H, d, J=6 Hz), 1.8–2.4 (2H, m), 2.80–3.00 (2H, m), 8.03 (1H, m).
Elution was continued to give Isomer B (330.0 mg).
IR (Nujol): 1750 cm$^{-1}$.
NMR (D$_2$O, δ): 1.28 (3H, d, J=6 Hz), 1.8–2.4 (2H, m), 2.8–3.0 (2H, m), 8.02, 8.05 (1H, each s).
MS: 382 (M$^+$+1).

EXAMPLE 27-8)

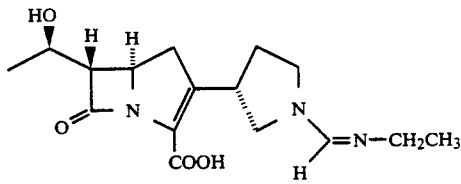

(5R,6S)-3-[(3S)-1-(N-Ethylformimidoyl)pyrrolidin-3-yl]-6-[(1R)-1-hydroxyethyl]-7-oxo-1-azabicyclo[3.2.0]hept-2-ene-2-carboxylic acid was obtained in 59.2% yield in substantially the same manner as that of Example 27-4).

IR (Nujol): 1740 cm$^{-1}$.
NMR (D$_2$O, δ): 1.28 (3H, d, J=6 Hz), 1.23 (3H, t, J=7 Hz), 1.8–2.4 (2H, m), 2.8–3.0 (2H, m), 7.98, 8.00 (1H, each s).
MS: 322 (M$^+$+1).

EXAMPLE 27-9)

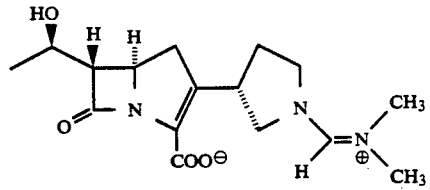

(5R,6S)-3-[(3S)-1-{(N,N-Dimethyliminio)methyl}pyrrolidin-3-yl]-6-[(1R)-1-hydroxyethyl]-7-oxo-1azabicyclo[3.2.0]hept-2-ene-2-carboxylate was obtained in b 45.0% yield in substantially the same manner as that of Example 12 by using a reaction mixture of N,N-dimethylformamide and dimethyl sulfate (1:1 equivalent) instead of benzyl formimidate hydrochloride.

IR (Nujol): 1740 cm$^{-1}$.
NMR (D$_2$O, δ): 1.25 (3H, d, J=6 Hz), 1.8–2.4 (2H, m), 3.20 (3H, s), 3.31(3H, s), 7.72 (1H, br s).
MS: 322 (M$^+$+1).

EXAMPLE 27-10)

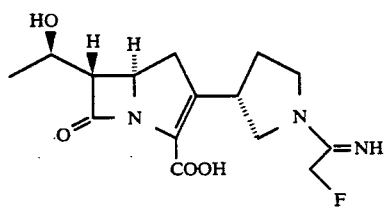

(5R,6S)-3-[(3S)-1-(2-Fluoroacetimidoyl)pyrrolidin-3-yl]-6-[(1R)-1-hydroxyethyl]-7-oxo-1-azabicyclo[3.2.0]hept-2-ene-2-carboxylic acid was obtained in 42.1% yield in substantially the same manner as that of Example 12 by using ethyl 2-fluoroacetimidate hydrochloride instead.

IR (Nujol): 1750 cm$^{-1}$.
NMR (D$_2$O, δ): 1.26 (3H, d, J=6 Hz), 1.7–2.4 (2H, m), 2.87 (2H, d, J=9 Hz).
MS: 326 (M$^+$+1).

EXAMPLE 27-11)

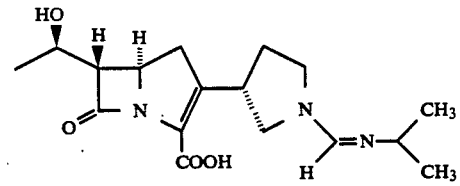

(5R,6S)-6-[(1R)-1-Hydroxyethyl](3S)-1-(N-isopropylformimidoyl)pyrrolidin-3-yl]-7-oxo-1-azabicyclo-[3.2.0]hept-2-ene-2-carboxylic acid was obtained in 28.6% yield in substantially the same manner as that of Example 27-4).

IR (Nujol): 1750 cm$^{-1}$.
NMR (D$_2$O, δ): 1.26 (3H, d, J=6 Hz), 1.27 (6H, d, J=6 Hz), 1.7–2.4 (2H, m), 2.88 (2H, d, J=9 Hz), 7.97 (1H, br s).
MS: 336 (M$^+$+1).

EXAMPLE 27-12)

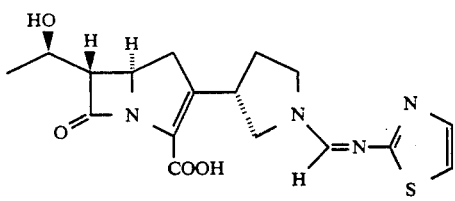

(5R,6S)-6-[(1R)-1-Hydroxyethyl]-7-oxo-3-[(3S)-1-{N-(thiazol-2-yl)formimidoyl}pyrrolidin-3-yl]-1-azabicyclo[3.2.0]hept-2-ene-2-carboxylic acid was obtained in 70.7% yield in substantially the same manner as that of Example 12 by using methyl N-(thiazol-2-yl) formimidate hydrochloride instead.

IR (Nujol): 1740 cm$^{-1}$.

NMR (D$_2$O, δ): 1.28 (3H, d, J=6 Hzz), 1.7-2.4 (2H, m), 2.88 (2H, d, J=9 Hz), 6.97 (1H, d, J=4 Hz), 7.30 (1H, d, J=4 Hz), 8.29 (1H, br s).

EXAMPLE 27-13)

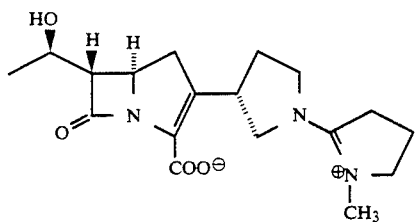

(5R,6S)-6-[(1R)-1-Hydroxyethyl]-3-[(3S)-1-{1-methyl-2-(1-pyrrolinio)}pyrrolidin-3-yl]-7-oxo-1-azabicyclo[3.2.0]hept-2-ene-2-carboxylate was obtained in 26.3% yield in substantially the same manner as that of Example 27-9) by using a reaction mixture of 1-methyl-2-pyrrolidinone and dimethyl sulfate (1:1 equivalent) instead.

IR (Nujol): 1750 cm$^{-1}$.

NMR (D$_2$O, δ): 1.28 (3H, d, J=6 Hz), 1.6-2.5 (5H, m), 3.29 (3H, s), 3.4-4.4 (8H, m).

MS: 348 (M$^+$+1).

EXAMPLE 27-14)

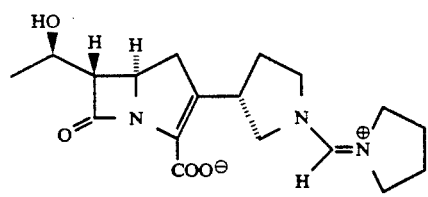

The above compound was obtained in 49.5% yield in substantially the same manner as that of Example 27-9) by using a reaction mixture of 1-formylpyrrolidine and dimethyl sulfate (1:1 equivalent) instead.

IR (Nujol): 1750 cm$^{-1}$.

NMR (D$_2$O, δ): 1.28 (3H, d, J=6 Hz), 1.5-2.5 (6H, m), 2.89 (2H, d, J=9 Hz), 7.92 (1H, br s).

MS: 348 (M$^+$+1).

EXAMPLE 27-15)

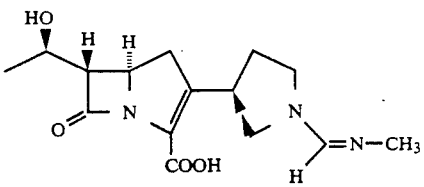

(5R,6S)-6-[(1R)-1-Hydroxyethyl]-3-[(3R)-1-(N-methylformimidoyl)pyrrolidin-3-yl]-7-oxo-1-azabicyclo[3.2.0]hept-2-ene-2-carboxylic acid was obtained in 13.0% yield in substantially the same manner as that of Example 12.

IR (Nujol): 1750, 1700 cm$^{-1}$.

NMR (D$_2$O, δ): 1.28 (3H, d, J=7.4 Hz), 1.9-2.3 (2H, m), 2.88 (2H, m), 3.10 (3H, s), 7.92 (1H, br s).

EXAMPLE 27-16)

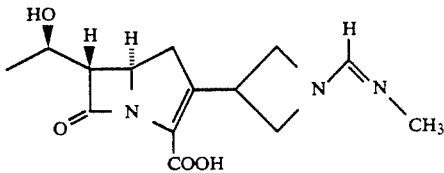

(5R,6S)-6-[(1R)-1-Hydroxyethyl]-3-[1-(N-methylformimidoyl)azetidin-3-yl]-7-oxo-1-azabicyclo[3.2.0]hept-2-ene-2-carboxylic acid was obtained in 25.7 % yield in substantially the same manner as that of Example 12.

IR (Nujol): 1755, 1700 cm$^{-1}$.

NMR (D$_2$O, δ): 1.28 (3H, d, J=6 Hz), 3.03 (3H, s), 3.07 (2H, d, J=9 Hz), 3.28-3.44 (1H, m), 7.66 (1H, br s).

EXAMPLE 27-17)

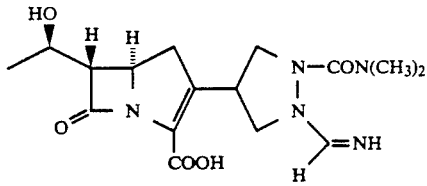

(5R,6S)-3-(1-Dimethylcarbamoyl-2-formimidoylpyrazolidin-4-yl)-6-[(1R)-1-hydroxyethyl]-7-oxo-1-azabicyclo[3.2.0]hept-2-ene-2-carboxylic acid was obtained in 32.4% yield in substantially the same manner as Example 12.

IR (Nujol): 1760 cm$^{-1}$.

NMR (D$_2$O, δ): 1.27 (3H, d, J=6 Hz), 3.0 (6H, s), 2.78-4.30 (10H, m), 8.13 (1H, s).

EXAMPLE 27-18)

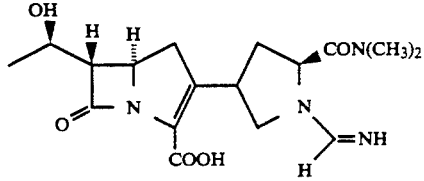

(5R,6S)-3-[(2S)-2-Dimethylcarbamoyl-1-for-mimidoylpyrrolidin-4-yl]-6-[(1R)-1-hydroxyethyl]-7-oxo-1-azabicyclo[3.2.0]hept-2-ene-2-carboxylic acid was obtained quantitatively in substantially the same manner as that of Example 12.

IR (Nujol): 1750 cm$^{-1}$.

NMR (D$_2$O, δ): 1.26 (3H, d, J=7 Hz), 2.99 (3H, s), 3.05 (3H, s), 7.92 (1H, m).

EXAMPLE 27-19)

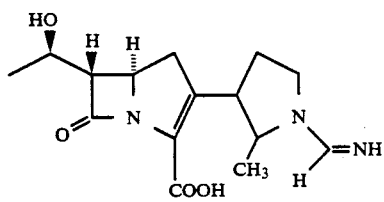

(5R,6S)-3-[1-Formimidoyl-2-methylpyrrolidin-3-yl]-6-[(1R)-1-hydroxyethyl]-7-oxo-1-azabicyclo[3.2.0]hept-2-ene-2-carboxylic acid was obtained in 28.3% yield in substantially the same manner a that of Example 12.

IR (Nujol): 1750, 1700 cm$^{-1}$.

NMR (D$_2$O, δ): 1.1–1.4 (6H, m), 1.8–2.4 (2H, m), 2.7–3.0 (2H, m), 7.82 (1H, br s).

EXAMPLE 27-20)

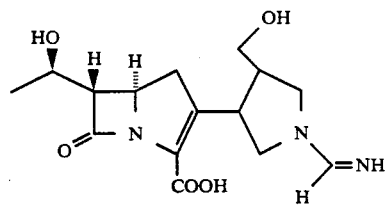

(5R,6S)-3-[1-Formimidoyl-4-(hydroxymethyl)pyrrolidin-3-yl]-6-[(1R)-1-hydroxyethyl]-7-oxo-1-azabicyclo[3.2.0]hept2-ene-2-carboxylic acid was obtained in 19.6% yield in substantially the same manner as that of Example 12.

IR (Nujol): 1750, 1705 cm$^{-1}$.

NMR (D$_2$O, δ): 1.2–1.3 (3H, m), 2.8–3.0 (2H, m), 7.97 (1H, br s).

EXAMPLE 27-21)

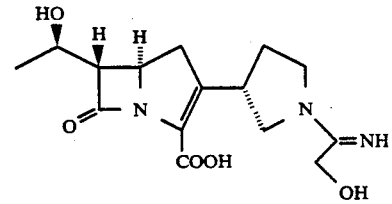

(5R,6S)-3-[(3S)-1-[2-Hydroxyacetimidoyl)pyrrolidin-3-yl]-6-[(1R)-1-hydroxyethyl]-7-oxo-1-azabicyclo[3.2.0]hept2-ene-2-carboxylic acid was obtained in 32.0% yield in substantially the same manner as that of Example 12 by using ethyl 2-hydroxyacetimidate hydrochloride instead.

IR (Nujol): 1750 cm$^{-1}$.

NMR (D$_2$O, δ): 1.25 (3H, d, J=6 Hz), 1.6–2.7 (2H, m), 2.8–3.0 (2H, m), 4.47 (2H, s).

EXAMPLE 27-22)

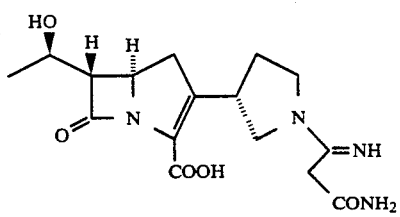

(5R,6R)-3[(3S)-1-(2-Carbamoylacetimidoyl)pyrrolidin-3-yl]-6-[(1R)-1-hydroxyethyl]-7-oxo-1-azabicyclo[3.2.0]hept2-ene-2-carboxylic acid was obtained in 31.6% yield in substantially the same manner as that of Example 12 by using ethyl 2-carbamoylacetimidate hydrochloride instead.

IR (Nujol): 1750, 1690 cm$^{-1}$.

NMR (D$_2$O, δ): 1.26 (3H, d, J=6 Hz), 1.5–2.6 (3H, m), 2.7–3.0 (2H, m), 3.0–4.4 (9H, m).

EXAMPLE 27-23)

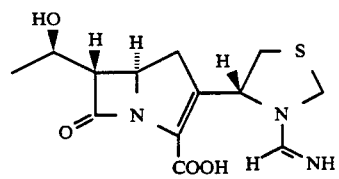

(5R,6S)-6-[(1R)-1-Hydroxyethyl]-3-[(4R)-3-formimidoylthiazolidin-4-yl]-7-oxo-1-azabicyclo[3.2.0]hept-2-ene-2-carboxylic acid was obtained in 72.7% yield in substantially the same manner as that of Example 12.

IR (Nujol): 1755–1735 cm$^{-1}$.

NMR (D$_2$O, δ): 1.28 (3H, d, J=6.2 Hz).

FAB-MS: 350 (M$^+$+K), 312 (M$^+$+1).

EXAMPLE 28

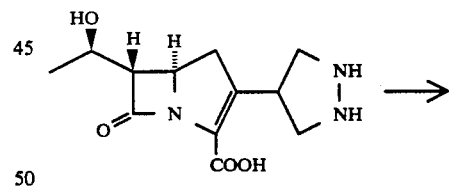

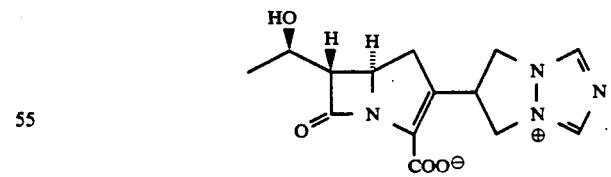

(5R,6S)-6-[(1R)-1-Hydroxyethyl]-3-(pyrazolidin-4-yl)-7-oxo-1-azabicyclo[3.2.0]hept-2-ene-2-carboxylic acid (100 mg) was dissolved in phosphate buffer (pH 4.0, 10 ml) and the pH of the solution was adjusted to pH 6.0 with 0.1N-aqueous hydrochloric acid at 0° C. The pH of the solution was adjusted to pH 7.0 with 0.1N-aqueous sodium hydroxide at 0° C. To this solution was added carefully ethyl formimidate hydrochloride (360 mg) by portions at 0° C., while adjusting the pH between 8.0 and 8.2 with 1N-solution sodium hydroxide. After the addition, the pH was adjusted to pH 6.8 with 0.1N-aqueous hydrochloric acid at 0° C. Concentration of the mixture in vacuo gave a residue, which was chromatographed on silica gel (30 ml) eluting with a mixture of acetonitrile and water (4:1, V/V) to give (5R,6S)-3-[6,7-dihydro-5H-pyrazolo[1,2-a][1,2,4]-6-(4-triazolio)]-6-[(1R)-1-hydroxyethyl]-7-oxo-1-azabicyclo[3.2.0]hept-2-ene-2-carboxylate (34.1 mg).

IR (Nujol): 1750 cm$^{-1}$.

NMR (D$_2$O, δ): 1.28 (3H, d, J=6 Hz), 2.6–4.33 (10H, m), 8.94 (1H, s).

EXAMPLE 29

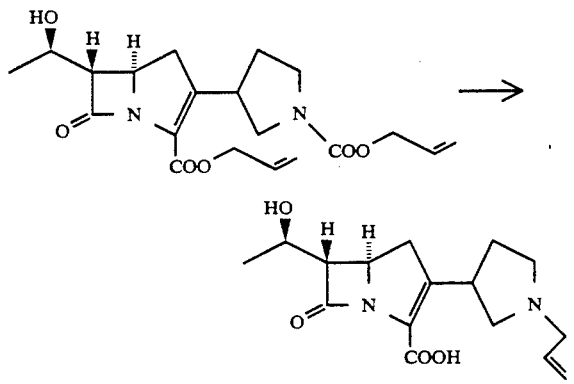

To a solution of allyl (5R,6S)-3-(1-allyloxycarbonyl-pyrrolidin-3-yl)-6-[(1R)-1-hydroxyethyl]-7-oxo-1-azabicyclo[3.2.0]hept-2-ene-2-carboxylate (1.24 g) in a mixture of tetrahydrofuran (20 ml) and ethanol (5 ml) were added triphenylphosphine (0.16 g), sodium 2-ethyl hexanoate (1.1 g), and tetrakis(triphenylphosphine)palladium(0) (0.37 g). After stirring at ambient temperature for 1 hour, the reaction mixture was washed with dichloromethane, and evaporated in vacuo. The residue was chromatographed on nonionic adsorption resin "Dialon HP-20" eluting with a mixture of water and acetonitrile (95:5, V/V). The fractions containing the desired compound were collected and lyophilized to give (5R,6S)-3-[1-allylpyrrolidin-3-yl)-6-[(1R)-1-hydroxyethyl]-7-oxo-1-azabicyclo[3.2.0]hept-2-ene-2-carboxylic acid (500 mg).

IR (Nujol): 1750.

NMR (D$_2$O, δ): 1.26 (3H, d, J=6 Hz), 1.7–2.4 (2H, m), 5.3–6.1 (3H, m).

EXAMPLE 30

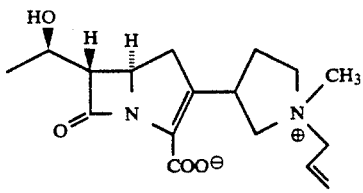

To a solution of (5R,6)-3-(1-allylpyrrolidin-3-yl)-6-[(1R)-1-hydroxyethyl]-7-oxo-1-azabicyclo[3.2.0]hept-2-ene-2-carboxylic acid (500 mg) in a mixture of water (2 ml), acetonitrile (30 ml) and methanol (10 ml) was added methyl iodide (15 ml). After stirring at 40° C. for 30 minutes, the solution was evaporated in vacuo. The residue was chromatographed on silica gel eluting with a mixture of acetonitrile and water (7:3, V/V). The fractions containing the desired compound were collected and lyophilized to give (5R,6S)-3-(1-allyl-1-methyl-3-pyrrolidinio)-6-[(1R)-1-hydroxyethyl]-7-oxo-1-azabicyclo[3.2.0]hept-2-ene-2-carboxylate (160 mg).

IR (Nujol): 1750 cm$^{-1}$.

NMR (D$_2$O, δ): 1.26 (3H, d, J=6 Hz), 1.82–2.6 (2H, m), 3.11 (3H, s), 5.5–6.2 (3H, m).

MS: 321 (M$^+$+1).

EXAMPLE 31-1)

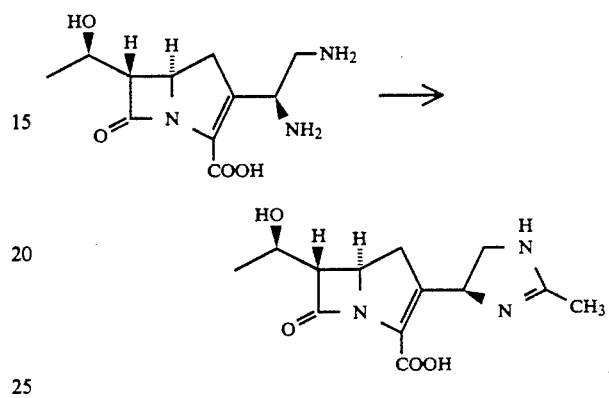

To a solution of (5R,6S)-3-[(1S)-1,2-diaminoethyl]-6-[(1R)-1-hydroxyethyl]-7-oxo-1-azabicyclo[3.2.0]hept-2-ene-2-carboxylic acid (1.00 g) in a mixture of water (100 ml) and tetrahydrofuran (100 ml) was added portionwise ethyl acetimidate hydrochloride (1.00 g) under ice-cooling with stirring, keeping the pH between 8.0 and 8.5 with saturated aqueous potassium carbonate. After stirring for 2 hours, the mixture was concentrated under reduced pressure to be about 10 ml-volume. The aqueous solution was subjected to a column chromatography on silica gel (100 g) and eluted with a mixture of water and acetonitrile (6:4, V/V). The fractions containing the object compound were collected, concentrated under reduced pressure, and lyophilized to give a solid. A solution of the solid in water (10 ml) was subjected to a column chromatography on "Diaion HP-20" and eluted with water. The fractions containing the objected compound were collected, concentrated under reduced pressure, and lyophilized to give (5R,6S)-6-[(1R)-1-hydroxyethyl]-3-[(4S)-2-methyl-2-imidazolin-4-yl]-7-oxo-1-azabicyclo[3.2.0]hept-2-ene-2-carboxylic acid (0.08 g) as a solid.

IR (KBr): 1755–1730 cm$^{-1}$.

NMR (D$_2$O, δ): 1.28 (3H, d, J=6.2 Hz), 2.22 (3H, s).

FAB-MS: 280 (M$^+$+1).

EXAMPLE 31-2)

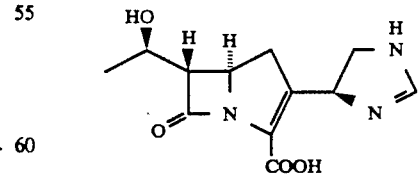

(5R,6)-6-[(1R)-1-Hydroxyethyl]-3-[(4S)-2-imidazolin-4-yl]-7-oxo-1-azabicyclo[3.2.0]hept-2-ene-2-carboxylic acid was obtained in 1.9% yield in substantially the same manner as that of Example 31-1).

NMR (D$_2$O, δ): 1.28 (3H, d, J=6.2 Hz), 8.18 (1H, s).

FAB-MS: 266 (M$^+$+1).

EXAMPLE 32-1)

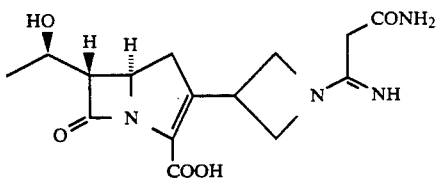

(5R,6S)-3-[1-(2-Carbamoylacetimidoyl)azetidin-3-yl]-6-[(1R)-1-hydroxyethyl]-7-oxo-1-azabicyclo[3.2.0]hept-2-ene-2-carboxylic acid was obtained in 25.1% yield in substantially the same manner as that of Example 27-22).

IR (Nujol): 1750, 1600 cm$^{-1}$.

NMR (D$_2$O, δ): 1.30 (3H, d, J=6 Hz), 2.95–3.45 (3H, m), 3.95–4.70 (9H, m).

EXAMPLE 32-2)

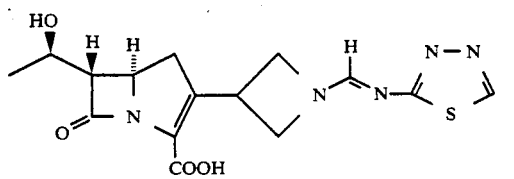

(5R,6S)-6-[(1R)-1-Hydroxyethyl]-7-oxo-3-[1-{N-(1,3,4-thiadiazol-2-yl)formimidoyl}azetidin-3-yl]-1-azabicyclo[3.2.0]hept-2-ene-2-carboxylic acid was obtained in 32.7% yield in substantially the same manner as that of Example 27-12).

IR (Nujol): 1750, 1600 cm$^{-1}$.

NMR (D$_2$O, δ): 1.30 (3H, d, J=6 Hz), 2.98–3.48 (3H, m), 3.94–4.70 (10H, m), 8.08 (1H, s), 8.85 (1H, s).

EXAMPLE 32-3)

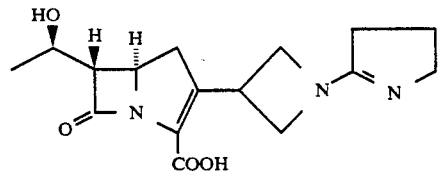

(5R,6S)-6-[(1R)-1-Hydroxyethyl]-7-oxo-3-[1-(1-pyrrolin-2-yl)azetidin-3-yl]-1-azabicyclo[3.2.0]hept-2-ene-2-carboxylic acid was obtained in 43.6% yield in substantially the same manner as that of Example 27-6).

IR (Nujol): 1750, 1680, 1580 cm$^{-1}$.

NMR (D$_2$O, δ): 1.28 (3H, d, J=6 Hz), 1.80–4.70 (16H, m).

What we claim is:

1. A compound of the formula:

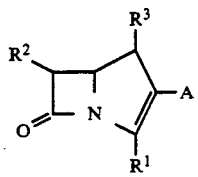

in which
R$^1$ is carboxy, protected carboxy or —COO$^{\ominus}$,

R$^2$ is hydroxy(lower)alkyl or protected hydroxy(lower)alkyl,
R$^3$ is hydrogen or lower alkyl,
A is a group of the formula:

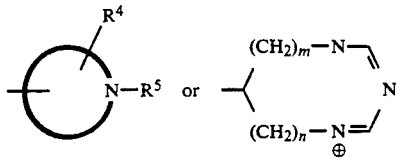

wherein

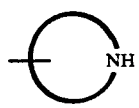

is N-containing aliphatic heterocyclic group optionally containing additional hetero atoms(s) selected from the group consisting of 2 to 6-membered heteromonocyclic group containing 1 to 4 nitrogen atom(s), which has nonconjugated double bond(s) only in its ring, saturated 4 to 6-membered heteromonocyclic group containing 1 to 4 nitrogen atom(s), saturated 4 to 6-membered heteromonocyclic group containing 1 to 2 oxygen atom(s) and 1 to 3 nitrogen atom(s), and saturated 4 to 6 membered heteromonocyclic group containing 1 to 2 sulfur atom(s) and 1 to 3 nitrogen atom(s), R$^4$ is hydrogen, hydroxy, protected hydroxy, hydroxy(lower)alkyl, protected hydroxy(lower)alkyl, lower alkyl, lower alkoxy(lower)alkyl, halogen, carbamoyl, mono- or di(lower)alkylcarbamoyl or imino-protective group, R$^5$ is hydrogen, lower alkenyl, carbamoyl, mono- or di(lower)alkylcarbamoyl, imino-protective group, or a group or the formula:

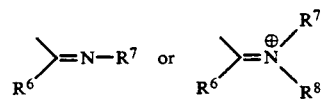

wherein
R$^6$ is hydrogen or lower alkyl optionally substituted by one to three substituent(s) selected from the group consisting of hydroxy, carbamoyl and halogen, R$^7$ is hydrogen, lower alkyl, cyano, hydroxy(lower)alkoxy(lower)alkyl or heterocyclic group selected from the group consisting of unsaturated 5 or 6-membered heteromonocyclic group containing 1 to 4 nitrogen atom(s), saturated 5 or 6-membered heteromonocyclic group containing 1 to 4 nitrogen atom(s), unsaturated condensed heterocyclic group containing 1 to 5 nitrogen atom(s), unsaturated 5 or 6-membered heteromonocyclic group containing 1 to 2 oxygen atom(s) and 1 to 3 nitrogen atom(s), saturated 5 or 6-membered heteromonocyclic group containing 1 to 2 oxygen atom(s) and 1 to 3 nitrogen atom(s), unsaturated condensed heterocyclic group containing 1 to 2 oxygen atom(s) and 1 to 3 nitrogen atom(s), unsaturated 5 or 6-membered heteromonocyclic group containing 1 to 2 sulfur atom(s) and 1 to 3 nitrogen atom(s), saturated 5 or 6-membered heteromonocyclic group containing 1 to 2 sulfur atom(s) and 1 to 3 nitrogen atom(s), unsaturated 5 or 6-membered heteromonocyclic group containing a sulfur atom, and unsaturated condensed, heterocyclic group containing 1 to 2 sulfur atom(s) and 1 to 3 nitrogen atom(s)

$R^8$ is lower alkyl, or $R^7$ is combined with $R^6$ or $R^8$ to form lower alkylene, and m and n are each an integer of 0 to 3, or pharmaceutically acceptable salt thereof.

2. The compound of claim 1, wherein
$R^1$ is carboxy, pharmaceutically acceptable esterified carboxy or $COO^\ominus$, $R^2$ is hydroxy(lower)alkyl, acyloxy(lower)alkyl, ar(lower)alkyloxy(lower)alkyl or trisubstituted silyloxy(lower)alkyl, $R^4$ is hydrogen, hydroxy, acyloxy, ar(lower)alkyloxy, trisubstituted silyloxy, hydroxy(lower)alkyl, acyloxy(lower)alkyl, ar(lower)alkyloxy(lower)alkyl, trisubstituted silyloxy(lower)alkyl, lower alkyl, lower alkoxy(lower)alkyl, halogen, carbamoyl, mono- or di(lower)alkylcarbamoyl or acyl, $R^5$ is hydrogen, lower alkenyl, carbamoyl, mono- or di(lower)alkylcarbamoyl, acyl, or a group of the formula:

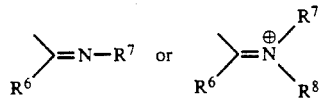

3. The compound of claim 2, wherein
$R^1$ is carboxy, lower alkenyloxycarbonyl, phenyl(or nitrophenyl)(lower)alkoxycarbonyl or $COO^\ominus$, $R^2$ is hydroxy(lower)alkyl, phenyl(or nitrophenyl)(lower)alkoxycarbonyloxy(lower)alkyl or tri(lower)alkylsilyloxy(lower)alkyl,
the formula:

is
saturated 4 to 6-membered heteromonocyclic group containing 1 to 4 nitrogen atom(s), saturated 4 to 6-membered heteromonocyclic group containing 1 to 2 oxygen atom(s) and 1 to 3 nitrogen atom(s), saturated 4 to 6-membered heteromonocyclic group containing 1 to 2 sulfur atom(s) and 1 to 3 nitrogen atom(s), or a heterocyclic group of the formula:

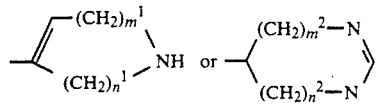

wherein
$m^1$ and $n^1$ are each an integer of 0 to 3, and
$m^2$ and $n^2$ are each as integer of 0 to 2, with a proviso that $1\leq m^1+n^1\leq 3$ and $0\leq m^2+n^2\leq 2$, $R^4$ is hydrogen, hydroxy, phenyl(or nitrophenyl)(lower)alkoxycarbonyloxy, tri(lower)alkylsilyloxy, hydroxy(lower)alkyl, phenyl(or nitrophenyl)(lower)alkoxycarbonyloxy(lower)alkyl, tri(lower)alkylsilyloxy(lower)alkyl, lower alkyl, lower alkoxy(lower)alkyl, halogen, carbamoyl, mono- or di(lower)alkylcarbamoyl, phenyl(or nitrophenyl)(lower)alkoxycarbonyl or lower alkenyloxycarbonyl, $R^5$ is hydrogen, lower alkenyl, carbamoyl, mono- or di(lower)alkylcarbamoyl, phenyl(or nitrophenyl)(lower)alkoxycarbonyl, lower alkenyloxycarbonyl, or a group of the formula:

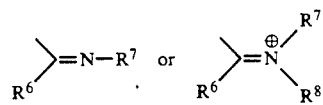

wherein
$R^6$ is hydrogen, lower alkyl, hydroxy(lower)alkyl, carbamoyl(lower)alkyl or halo(lower)alkyl, $R^7$ is hydrogen, lower alkyl, cyano, hydroxy(lower)alkoxy(lower)alkyl, pyrrolyl, pyrrolinyl, imidazolyl, pyrazolyl, pyridyl, and its N-oxide, pyrimidyl, pyrazinyl, pyridazinyl, triazolyl, tetrazolyl, dihydrotriazinyl, azetidinyl, pyrrolidinyl, imidazolidinyl, piperidinyl, pyrazolidinyl, piperazinyl, indolyl, isoindolyl, indolizinyl, benzimidazolyl, quinolyl, isoquinolyl, indazolyl, benzotriazolyl, tetrazolopyridyl, tetrazolopyridazinyl, dihydrotriazolopyridazinyl, oxazolyl, isoxazolyl, oxadiazolyl, morpholinyl, benzoxazolyl, benzoxadiazolyl, thiazolyl, thiazolinyl, thiadiazolyl, thiazolidinyl, thienyl, benzothiazolyl, benzothiadiazolyl, $R^8$ is lower alkyl, or $R^7$ is combined with $R^6$ or $R^8$ to form lower alkylene, and m and n are each an integer of 0 to 3.

4. The compound of claim 3, wherein $R^1$ is carboxy, $C_2$-$C_4$ alkenyloxycarbonyl, phenyl(or nitrophenyl)($C_1$-$C_4$)alkoxycarbonyl or $COO^\ominus$, $R^2$ is hydroxy($C_1$-$C_4$)alkyl, phenyl(or nitrophenyl)($C_1$-$C_4$)alkoxycarbonyloxy($C_1$-$C_4$)alkyl or tri($C_1$-$C_4$)alkylsilyloxy($C_1$-$C_4$)alkyl, $R^3$ is hydrogen or $C_1$-$C_4$ alkyl,
the formula:

is azetidinyl, pyrrolidinyl, imidazolidiny piperidinyl, pyrazolidinyl, piperazinyl, morpholinyl, thiazolidinyl, isothiazolidinyl, thiadiazolidinyl, thiomorpholinyl or a group of the formula:

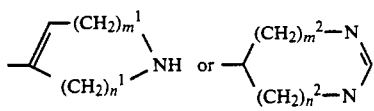

wherein
$m^1$ and $n^1$ are each an integer of 0 to 3, and
$m^2$ and $n^2$ are each an integer of 0 to 2, with a proviso that $1 \leq m^1 + n^1 \leq 3$ and $0 \leq m^2 + n^2 \leq 2$, $R^4$ is hydrogen, hydroxy, phenyl(or nitrophenyl)($C_1$-$C_4$)alkoxycarbonyloxy, tri($C_1$-$C_4$)alkylsilyloxy, hydroxy($C_1$-$C_4$)alkyl, phenyl(or nitrophenyl)($C_1$-$C_4$)alkoxycarbonyloxy($C_1$-$C_4$)alkyl, tri($C_1$-$C_4$)alkylsilyloxy($C_1$-$C_4$)alkyl, $C_1$-$C_4$ alkyl, $C_1$-$C_4$ alkoxy($C_1$-$C_4$)alkyl, halogen, carbamoyl, mono- or di($C_1$-$C_4$)alkylcarbamoyl, phenyl(or nitrophenyl)($C_1$-$C_4$)alkoxycarbonyl or $C_2$-$C_4$ alkenyloxycarbonyl, $R^5$ is hydrogen, $C_2$-$C_4$ alkenyl, carbamoyl, mono- or di($C_1$-$C_4$)alkylcarbamoyl, phenyl(or nitrophenyl)($C_1$-$C_4$)alkoxycarbonyl, $C_2$-$C_4$ alkenyloxycarbonyl or a group of the formula:

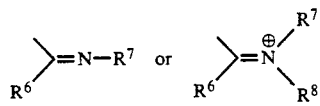

wherein
$R^6$ is hydrogen, $C_1$-$C_4$ alkyl hydroxy($C_1$-$C_4$)alkyl, carbamoyl($C_1$-$C_4$)alkyl or halo($C_1$-$C_4$)alkyl,
$R^7$ is hydrogen, $C_1$-$C_4$ alkyl, cyano, hydroxy($C_1$-$C_4$)alkoxy($C_1$-$C_4$)alkyl, thiazolyl, thiazolinyl, thiadiazolyl, thiazolidinyl, isothiazolidinyl or thiadiazolidinyl,
$R^8$ is $C_1$-$C_4$ alkyl, or
$R^7$ is combined with $R^6$ or $R^8$ to form $C_1$-$C_4$ alkylene, and
m and n are each an integer of 0 to 3.

5. A compound of claim 4, wherein the formula:

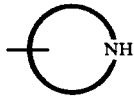

is pyrrolinyl, imidazolinyl, tetrahydropyridyl, azetidinyl, pyrrolidinyl, piperidinyl, pyrazolidinyl, piperazinyl, morpholinyl, thiazolidinyl or thiomorpholinyl, and $R^5$ is hydrogen, $C_2$-$C_4$ alkenyl, $C_2$-$C_4$ alkenyloxycarbonyl, phenyl(or nitrophenyl)($C_1$-$C_4$)alkoxycarbonyl, di($C_1$-$C_4$)alkylcarbamoyl, ($C_1$-$C_4$)alkanimidoyl, N-($C_1$-$C_6$)alkyl($C_1$-$C_4$)alkanimidoyl, N-[hydroxy($C_1$-$C_4$)alkoxy($C_1$-$C_4$)alkyl]($C_1$-$C_4$)alkanimidoyl, N-cyano($C_1$-$C_4$)alkanimidoyl, thiazolidinyl or isothiazolidinyl or thiadiazolidinyl)($C_1$-$C_4$)alkanimidoyl, C-hydroxy(or halo or carbamoyl)($C_1$-$C_4$)alkanimidoyl, N,N-di($C_1$-$C_4$)alkylimino($C_1$-$C_4$)alkyl, and a compound of the formula:

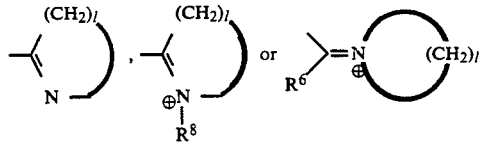

wherein
$R^6$ is hydrogen or $C_1$-$C_4$ alkyl, $R^8$ is $C_1$-$C_4$ alkyl, and l is an integer of 3 to 5 to from 5 to 6-membered N-containing heterocyclic ring respectively.

6. The compound of claim 5, wherein
$R^1$ is carboxy or COO$^\ominus$,
$R^2$ is hydroxy($C_1$-$C_4$)alkyl, and
$R^4$ is hydrogen, hydroxy, hydroxy($C_1$-$C_4$)alkyl, $C_1$-$C_4$ alkyl, $C_1$-$C_4$ alkoxy($C_1$-$C_4$)alkyl, halogen or di($C_1$-$C_4$)alkylcarbamoyl.

7. The compound of claim 6, wherein
$R^2$ is 1-hydroxyethyl,
$R^3$ is hydrogen or methyl,
$R^4$ is hydrogen, hydroxy, hydroxymethyl, methyl, methoxymethyl, fluoro or dimethylcarbamoyl, and
$R^5$ is hydrogen, allyl, allyloxycarbonyl, benzyloxycarbonyl, dimethylcarbamoyl, formimidoyl, acetimidoyl, N-methyl(or ethyl or isopropyl)formimidoyl, N-methylacetimidoyl, N-[2-(2-hydroxyethoxy)ethyl]formimidoyl, N-cyanoformimidoyl, N-(thiazol-2-yl)formimidoyl, N-(1,3,4-thiadiazol-2-yl)formimidoyl, 2-hydroxy(or fluoro or carbamoyl)acetimidoyl, N,N-dimethyliminiomethyl, 1-pyrrolin-2-yl, 1-methyl-2-(1-pyrrolinio), or a compound of the formula:

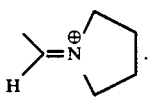

8. A pharmaceutical composition which comprises a compound of claim 1 or pharmaceutically acceptable salts thereof and a pharmaceutically acceptable carrier or excipient.

9. A method for treating infectious diseases caused by bacteria which comprises administering an effective amount of a compound of claim 1 or a pharmaceutically acceptable salt thereof to a human or animal.

* * * * *

UNITED STATES PATENT AND TRADEMARK OFFICE
CERTIFICATE OF CORRECTION

PATENT NO. : 5,102,877

DATED : April 7, 1992

INVENTOR(S) : Masayoshi MURATA, et al.

It is certified that error appears in the above-identified patent and that said Letters Patent is hereby corrected as shown below:

Column 3, lines 38-47;

"  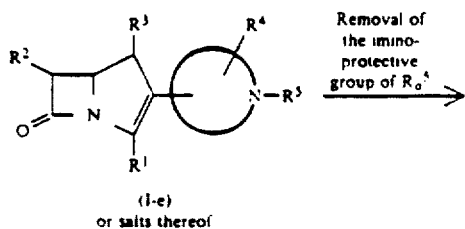  "

Should read;

--  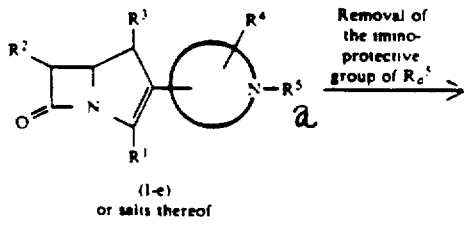  --.

UNITED STATES PATENT AND TRADEMARK OFFICE
CERTIFICATE OF CORRECTION

PATENT NO. : 5,102,877

DATED : April 7, 1992

INVENTOR(S) : Masayoshi MURATA, et al.

It is certified that error appears in the above-identified patent and that said Letters Patent is hereby corrected as shown below:

Column 3, lines 49-57;

" 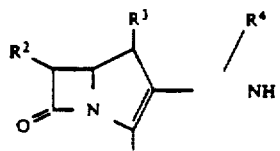 ",

Should read;

-- 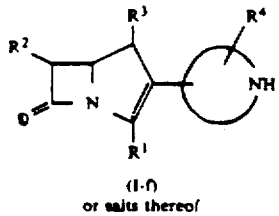 --.

UNITED STATES PATENT AND TRADEMARK OFFICE
CERTIFICATE OF CORRECTION

PATENT NO. : 5,102,877

DATED : April 7, 1992

INVENTOR(S) : Masayoshi MURATA, et al.

It is certified that error appears in the above-identified patent and that said Letters Patent is hereby corrected as shown below:

Column 78, Example 14-2), lines 51-63

EXAMPLE 14-2)

" 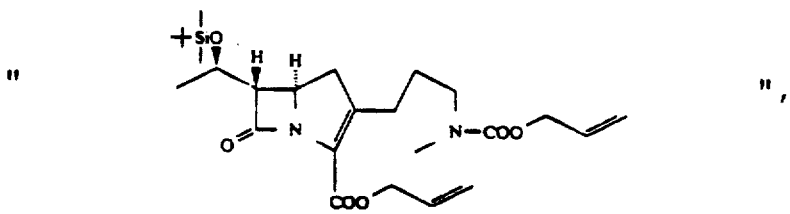 ",

Should read;

EXAMPLE 14-2)

-- 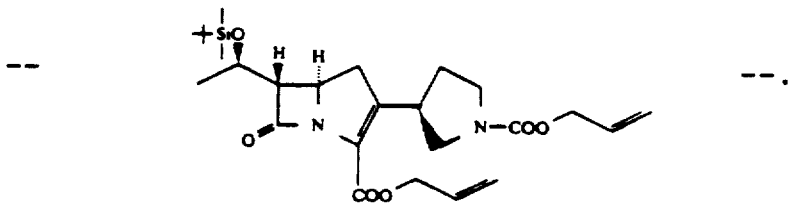 --.

UNITED STATES PATENT AND TRADEMARK OFFICE
CERTIFICATE OF CORRECTION

PATENT NO. : 5,102,877
DATED : April 7, 1992
INVENTOR(S) : Masayoshi MURATA, et al.

It is certified that error appears in the above-identified patent and that said Letters Patent is hereby corrected as shown below:

Column 79, Example 15-2), lines 51-58.

EXAMPLE 15-2)

" 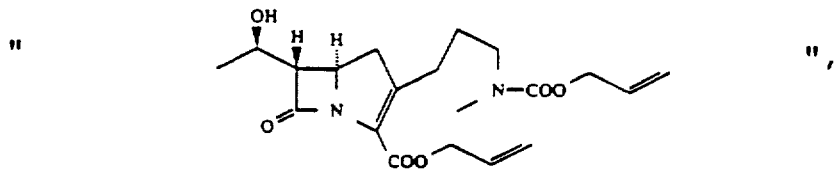 ",

Should read;

EXAMPLE 15-2)

-- 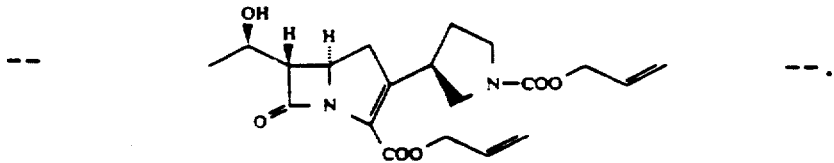 --.

UNITED STATES PATENT AND TRADEMARK OFFICE
CERTIFICATE OF CORRECTION

PATENT NO. : 5,102,877

DATED : April 7, 1992

INVENTOR(S) : Masayoshi MURATA, et al.

It is certified that error appears in the above-identified patent and that said Letters Patent is hereby corrected as shown below:

Column 80, Example 16-2), lines 36-45.

EXAMPLE 16-2)

" 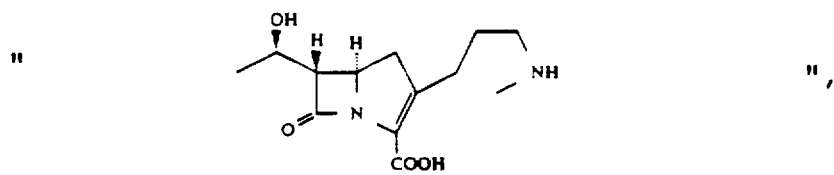 ",

Should read;

EXAMPLE 16-2)

-- 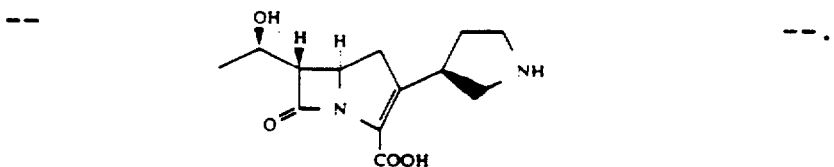 --.

UNITED STATES PATENT AND TRADEMARK OFFICE
CERTIFICATE OF CORRECTION

PATENT NO. : 5,102,877

DATED : April 7, 1992

INVENTOR(S) : Masayoshi MURATA, et al.

It is certified that error appears in the above-identified patent and that said Letters Patent is hereby corrected as shown below:

Column 94, Example 25-11), lines 10-19.

EXAMPLE 25-11)

" 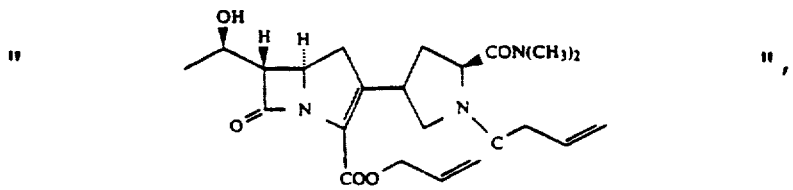 " ,

Should read;

EXAMPLE 25-11)

-- 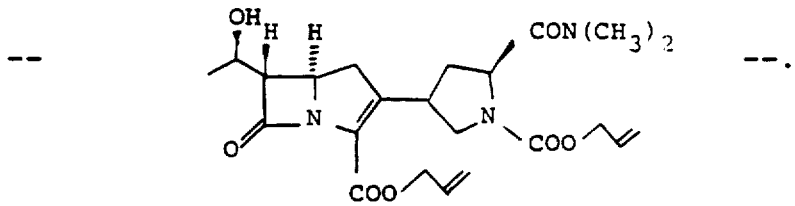 --.

UNITED STATES PATENT AND TRADEMARK OFFICE
CERTIFICATE OF CORRECTION

PATENT NO. : 5,102,877

DATED : April 7, 1992

INVENTOR(S) : Masayoshi MURATA, et al.

It is certified that error appears in the above-identified patent and that said Letters Patent is hereby corrected as shown below:

Column 110, lines 7-19

A is a group of the formula:

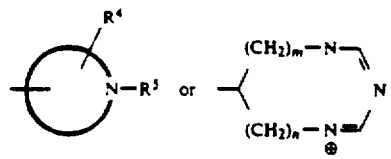

" ";

wherein

Should read;

A is a group of the formula:

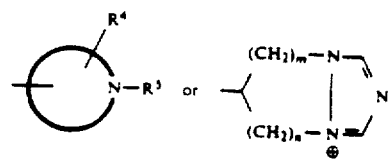

-- --.

wherein

UNITED STATES PATENT AND TRADEMARK OFFICE
CERTIFICATE OF CORRECTION

PATENT NO. : 5,102,877
DATED : April 7, 1992
INVENTOR(S) : Masayoshi MURATA, et al.

It is certified that error appears in the above-identified patent and that said Letters Patent is hereby corrected as shown below:

Column 110, line 25,
 "2 to 6-membered";

Should read;
 --4 to 6-membered--.

Column 113, lines 3-8,

"  ",

Should read;

-- 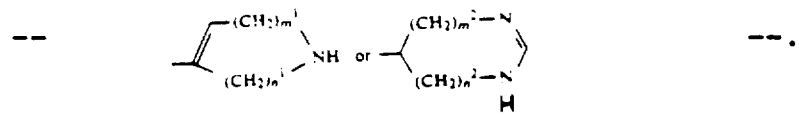 --.

UNITED STATES PATENT AND TRADEMARK OFFICE
CERTIFICATE OF CORRECTION

PATENT NO. : 5,102,877

DATED : April 7, 1992

INVENTOR(S) : Masayoshi MURATA, et al.

It is certified that error appears in the above-identified patent and that said Letters Patent is hereby corrected as shown below:

Column 114, line 3,
"alkanimidoyl, thiazolidinyl",
Should read;
--alkanimidoyl N-thiazolyl (or thiazolinyl or thiadiazolyl or thiazolidinyl--.

Signed and Sealed this

Nineteenth Day of October, 1993

Attest:

BRUCE LEHMAN

*Attesting Officer*     *Commissioner of Patents and Trademarks*